US009642669B2

(12) United States Patent
Takashino et al.

(10) Patent No.: US 9,642,669 B2
(45) Date of Patent: May 9, 2017

(54) TREATMENT SYSTEM, AND TREATMENT METHOD FOR LIVING TISSUE USING ENERGY

(75) Inventors: Tomoyuki Takashino, Hino (JP); Kenichi Kimura, Hachioji (JP)

(73) Assignee: OLYMPUS CORPORATION (JP)

( * ) Notice: Subject to any disclaimer, the term of this patent is extended or adjusted under 35 U.S.C. 154(b) by 1162 days.

(21) Appl. No.: 12/060,359

(22) Filed: Apr. 1, 2008

(65) Prior Publication Data

US 2009/0248002 A1 Oct. 1, 2009

(51) Int. Cl.
*A61B 18/14* (2006.01)
*A61B 18/08* (2006.01)
(Continued)

(52) U.S. Cl.
CPC ........ *A61B 18/085* (2013.01); *A61B 18/1442* (2013.01); *A61B 18/1447* (2013.01);
(Continued)

(58) Field of Classification Search
CPC ....... A61B 18/08; A61B 18/082; A61B 18/10; A61B 18/14; A61B 18/1442; A61B 18/1445; A61B 18/1449; A61B 18/1492; A61B 2018/00791; A61B 2018/00875; A61B 2018/00702; A61B 2018/00577; A61B 2018/00646; A61B 2018/0063;
(Continued)

(56) References Cited

U.S. PATENT DOCUMENTS 5,540,684 A * 7/1996 Hassler, Jr. .................... 606/40
5,647,871 A 7/1997 Levine et al.
(Continued)

FOREIGN PATENT DOCUMENTS

JP 62-204739 9/1987
JP 62-211057 9/1987
(Continued)

OTHER PUBLICATIONS

US 6,663,629, 12/2003, Buysse et al. (withdrawn)
(Continued)

*Primary Examiner* — Michael Peffley
*Assistant Examiner* — Khadijeh Vahdat
(74) *Attorney, Agent, or Firm* — Ostrolenk Faber LLP

(57) ABSTRACT

A treatment system includes a pair of holding members, a high-frequency energy output section, a heat generating section and a control section. At least one of the pair of holding members moves to the other holding member. The high-frequency energy output section and the heat generating section are provided on at least one of the holding members. The high-frequency energy output section exerts high-frequency energy to a living tissue to denature the living tissue, and collects the biological information of the living tissue. The heat generating section applies heat to it held between the holding members, generates the heat owing to the supply of the energy, and conducts the heat therefrom to denature the living tissue. The control section controls the output of the energy to the high-frequency energy output section and the heat generating section based on the biological information collected by the high-frequency energy output section.

12 Claims, 26 Drawing Sheets

(51) Int. Cl.
*A61B 17/00* (2006.01)
*A61B 18/00* (2006.01)

(52) U.S. Cl.
CPC ............... *A61B 2017/00084* (2013.01); *A61B 2018/0063* (2013.01); *A61B 2018/00666* (2013.01); *A61B 2018/00678* (2013.01); *A61B 2018/00702* (2013.01); *A61B 2018/00761* (2013.01); *A61B 2018/00791* (2013.01); *A61B 2018/00875* (2013.01); *A61B 2018/00994* (2013.01)

(58) Field of Classification Search
CPC  A61B 2018/00797; A61B 2018/00601; A61B 2018/00619; A61B 2018/00351; A61B 2018/00589; A61B 2018/00595; A61B 2018/00821; A61B 2018/00827; A61B 2018/00892; A61B 2018/00714; A61B 2018/00767
USPC ................................................ 606/28, 45–52
See application file for complete search history.

(56) References Cited

U.S. PATENT DOCUMENTS

| | | | |
|---|---|---|---|
| 5,951,546 | A | 9/1999 | Lorentzen |
| 6,228,080 | B1 | 5/2001 | Gines |
| 6,500,176 | B1 | 12/2002 | Truckai et al. |
| 6,740,085 | B2 * | 5/2004 | Hareyama et al. ............ 606/51 |
| 6,926,716 | B2 | 8/2005 | Baker et al. |
| 6,953,461 | B2 | 10/2005 | McClurken et al. |
| 7,160,299 | B2 | 1/2007 | Baily |
| 2002/0013583 | A1 * | 1/2002 | Camran et al. ................ 606/48 |
| 2002/0082593 | A1 | 6/2002 | Hareyama et al. |
| 2003/0073987 | A1 * | 4/2003 | Sakurai et al. ................ 606/28 |
| 2003/0078577 | A1 * | 4/2003 | Truckai et al. ................ 606/51 |
| 2004/0015163 | A1 * | 1/2004 | Buysse et al. ................ 606/34 |
| 2005/0101945 | A1 | 5/2005 | Sakurai et al. |
| 2005/0113828 | A1 | 5/2005 | Shields et al. |
| 2006/0064086 | A1 | 3/2006 | Odom |
| 2006/0069388 | A1 | 3/2006 | Truckai et al. |
| 2006/0217706 | A1 | 9/2006 | Lau et al. |
| 2006/0271041 | A1 * | 11/2006 | Eder et al. ..................... 606/50 |
| 2008/0015575 | A1 * | 1/2008 | Odom et al. ................... 606/51 |
| 2009/0076506 | A1 | 3/2009 | Baker |

FOREIGN PATENT DOCUMENTS

| | | |
|---|---|---|
| JP | 08-098845 | 4/1996 |
| JP | 2000-271145 | 10/2000 |
| JP | 2001-190561 | 7/2001 |
| JP | 2005-000224 | 1/2005 |
| JP | 2007-037568 | 2/2007 |
| JP | 2008-023335 | 2/2008 |
| JP | 2008-055151 | 3/2008 |
| WO | WO 99/40857 | 8/1999 |
| WO | WO 02/058544 | 8/2002 |
| WO | WO 02/080784 | 10/2002 |

OTHER PUBLICATIONS

Extended European Search Report dated Jul. 27, 2009 in corresponding European Patent Application No. EP 09 00 4843 (English language).

Letter from German associate dated Jul. 29, 2009 forwarding the Extended European Search Report dated Jul. 27, 2009 to Japanese associate, including discussion of relevancy thereof. German associate's letter dated Jul. 29, 2009 was date stamped received by Japanese associate on Aug. 3, 2009 (English language).

Office Action issued by the Japanese Patent Office on Mar. 21, 2012 in connection with corresponding Japanese Patent Application No. 2009-083481.

Translation of Office Action issued by the Japanese Patent Office on Mar. 21, 2012 in connection with corresponding Japanese Patent Application No. 2009-083481.

* cited by examiner

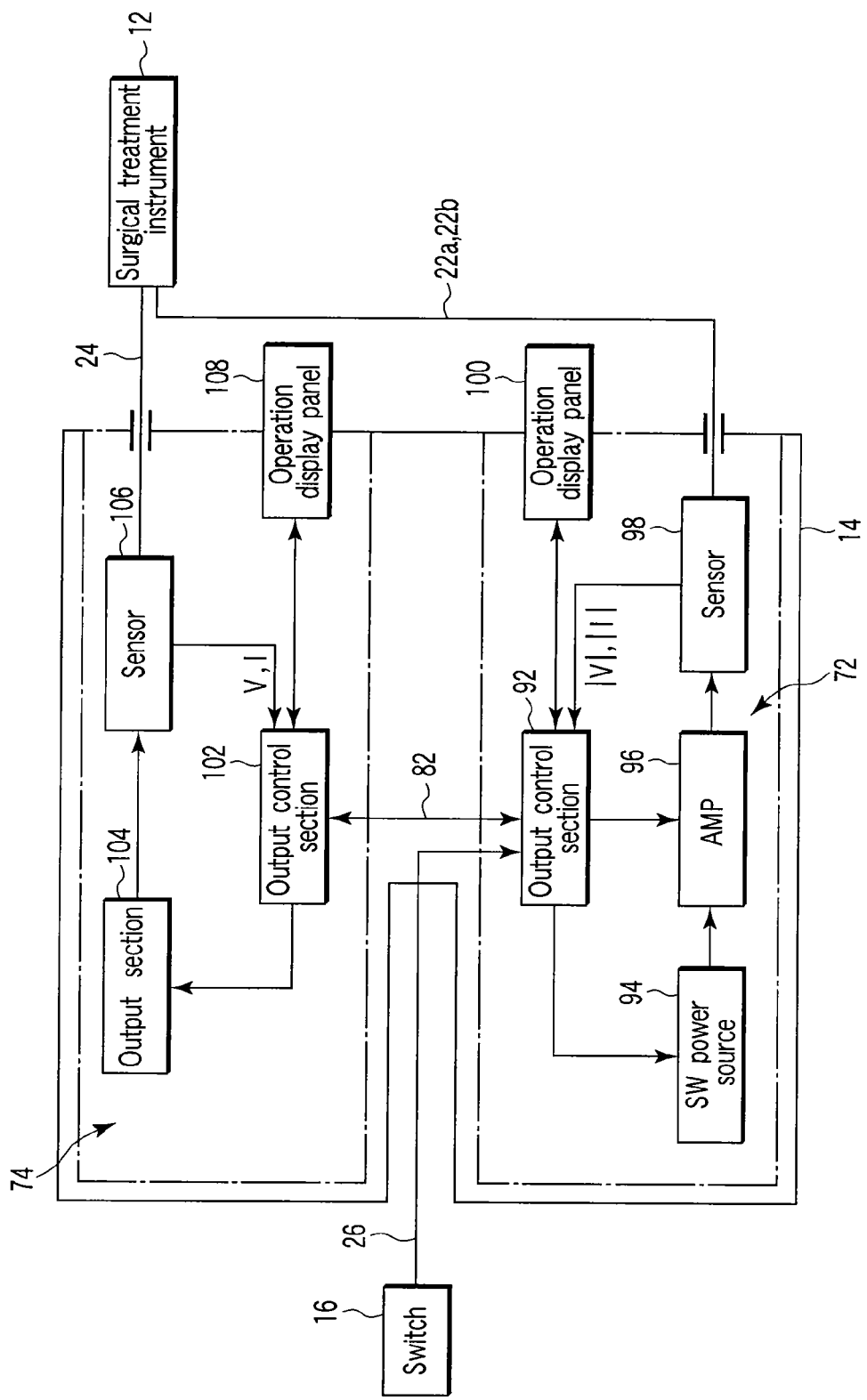
F I G. 2

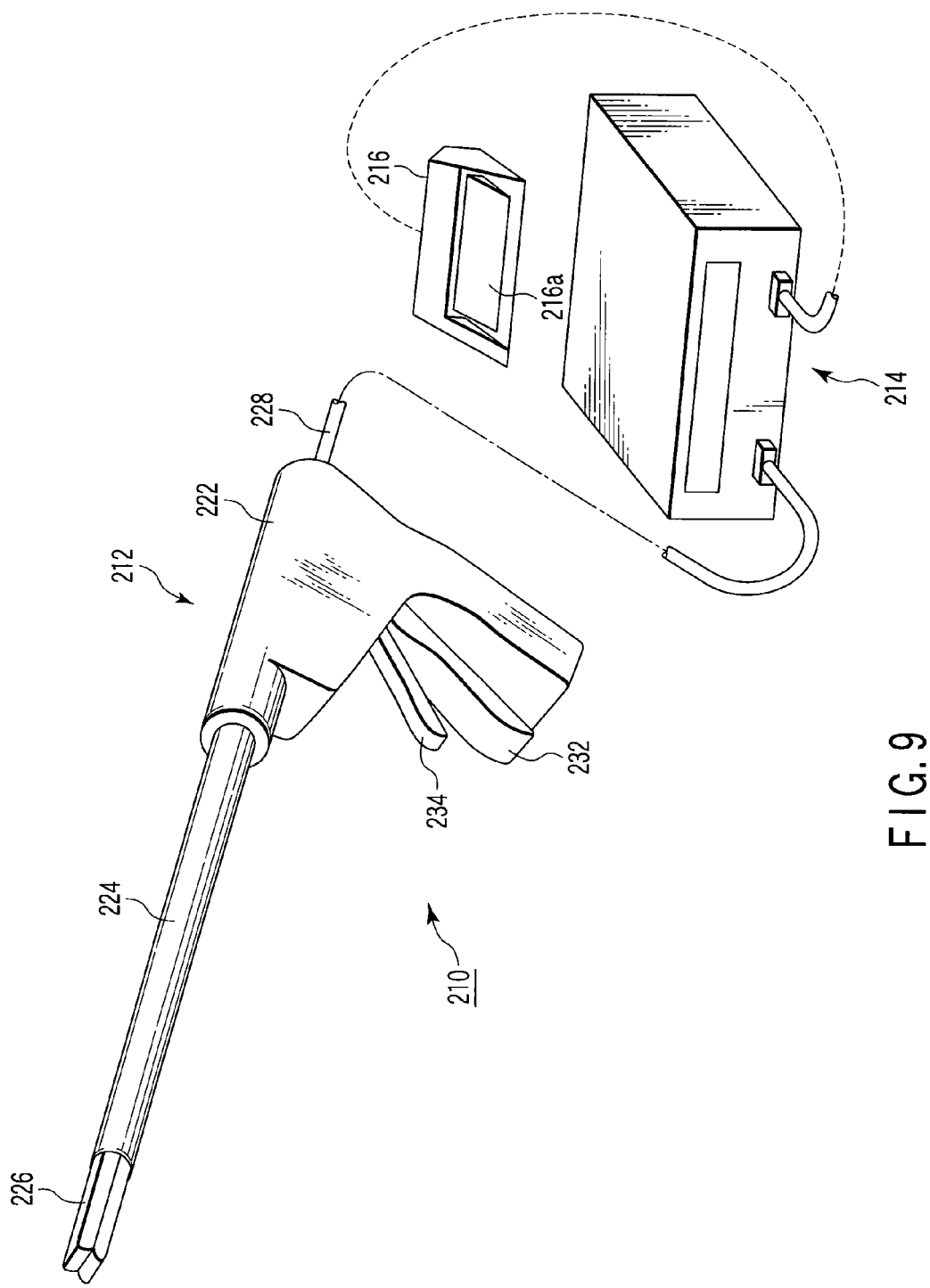
F I G. 9

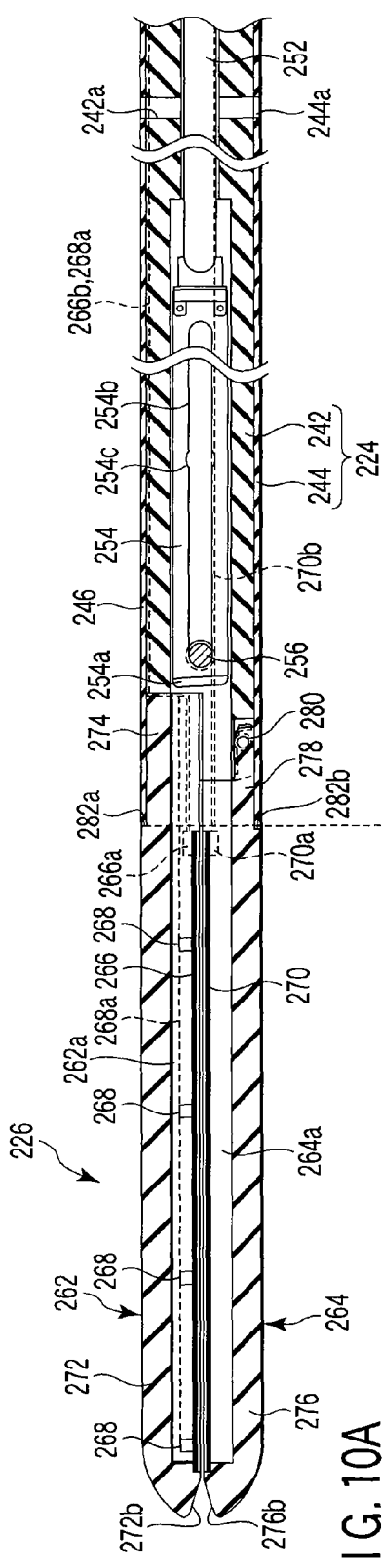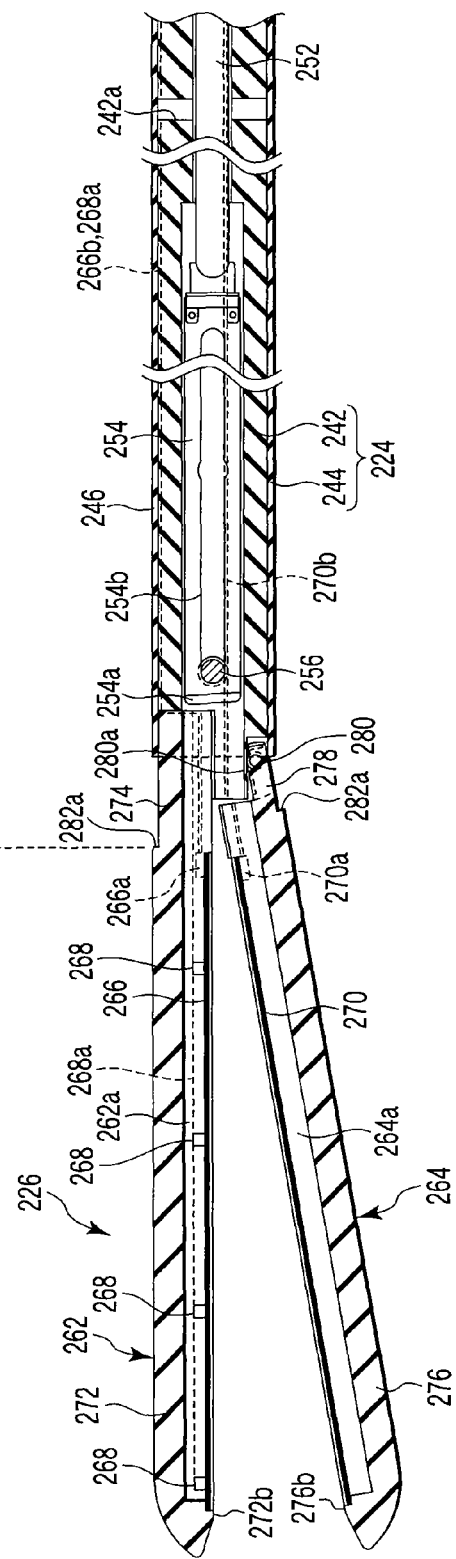
FIG. 10A
FIG. 10B

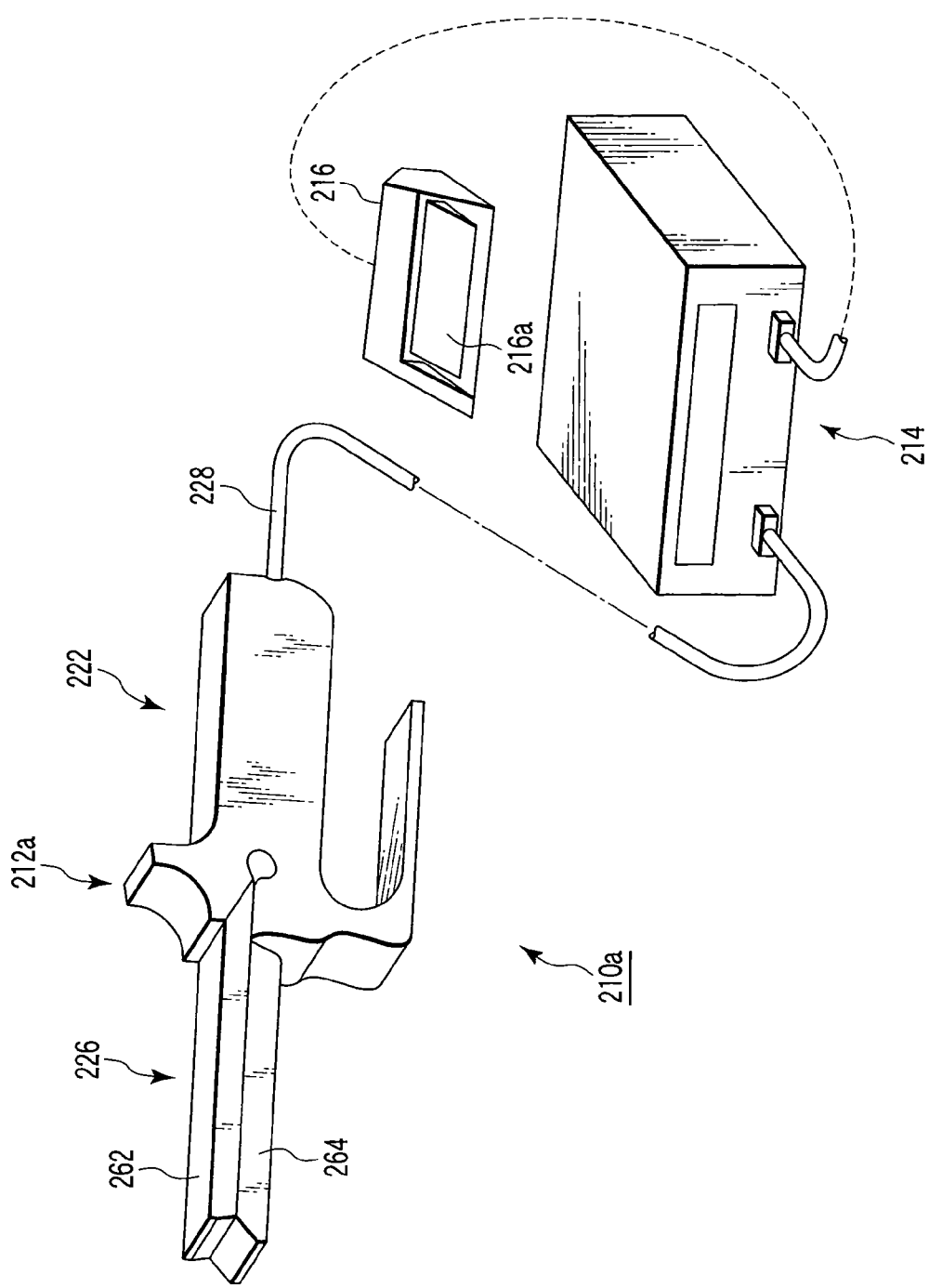
F I G. 16

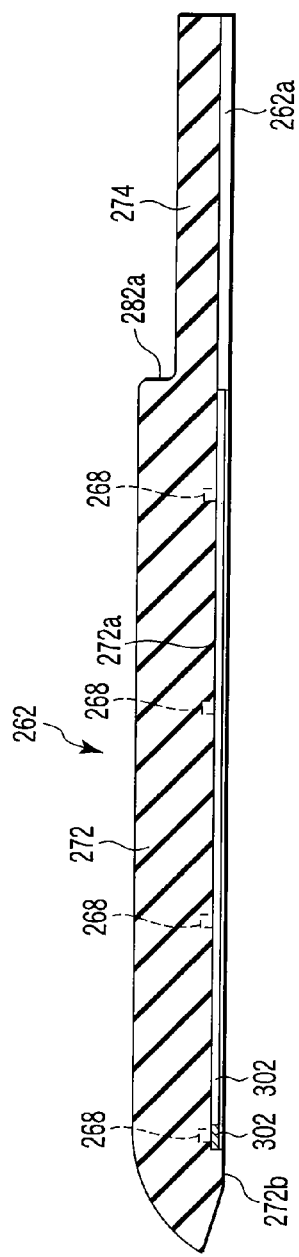
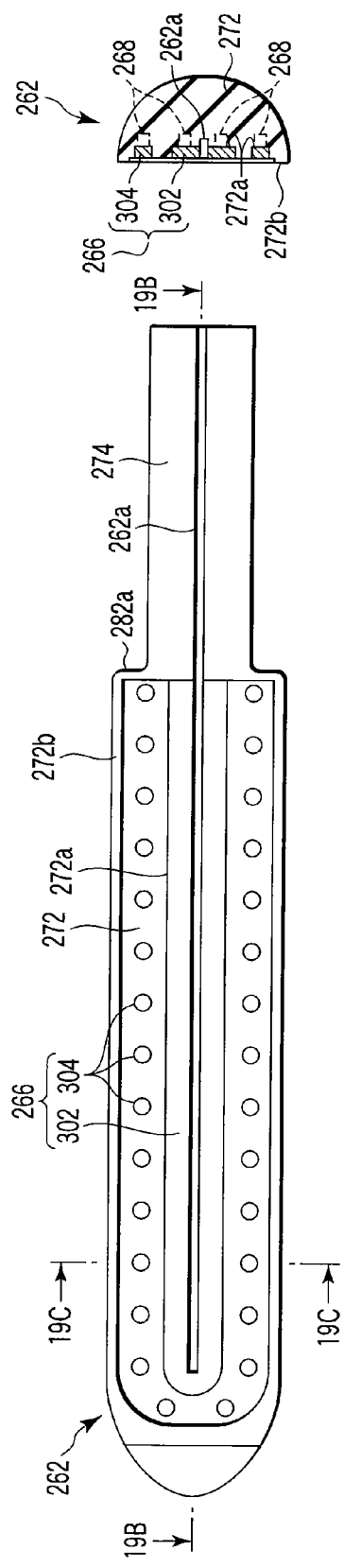

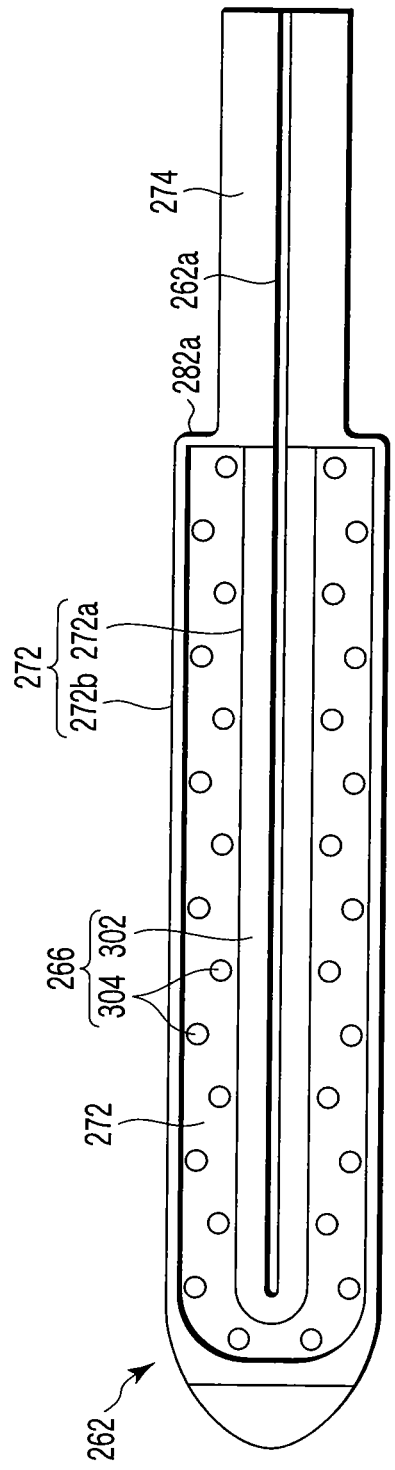
F I G. 19D

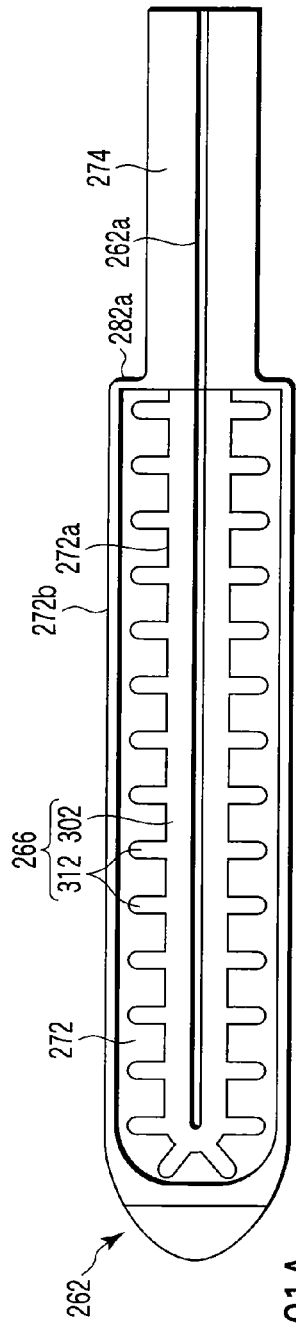 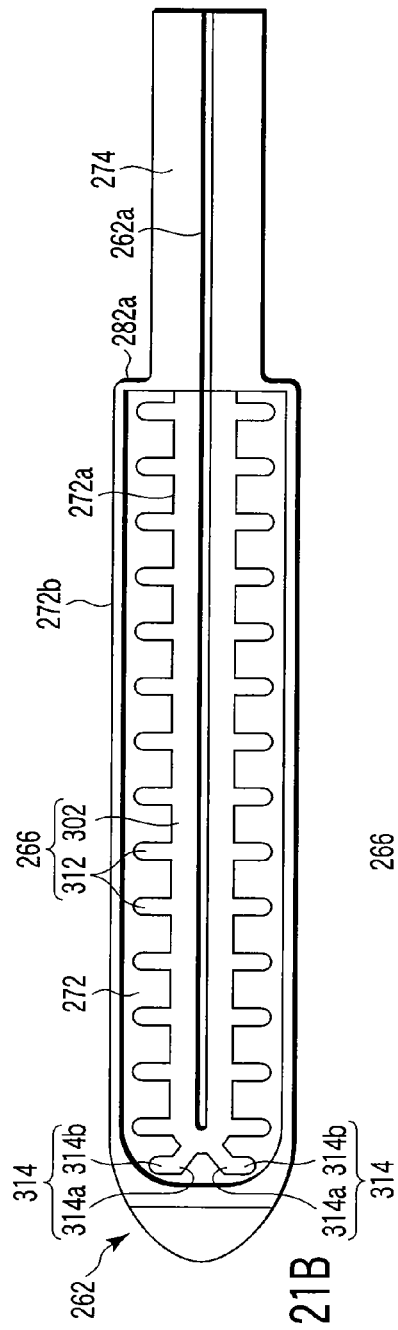 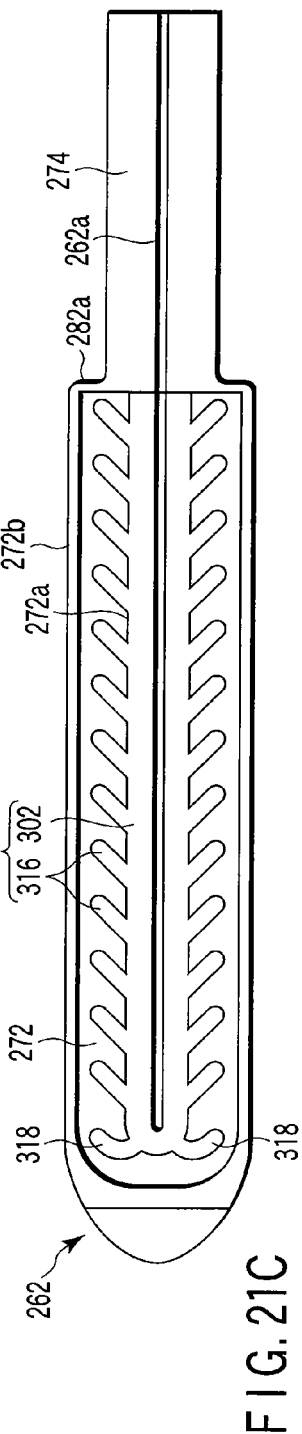
F I G. 21A    F I G. 21B    F I G. 21C

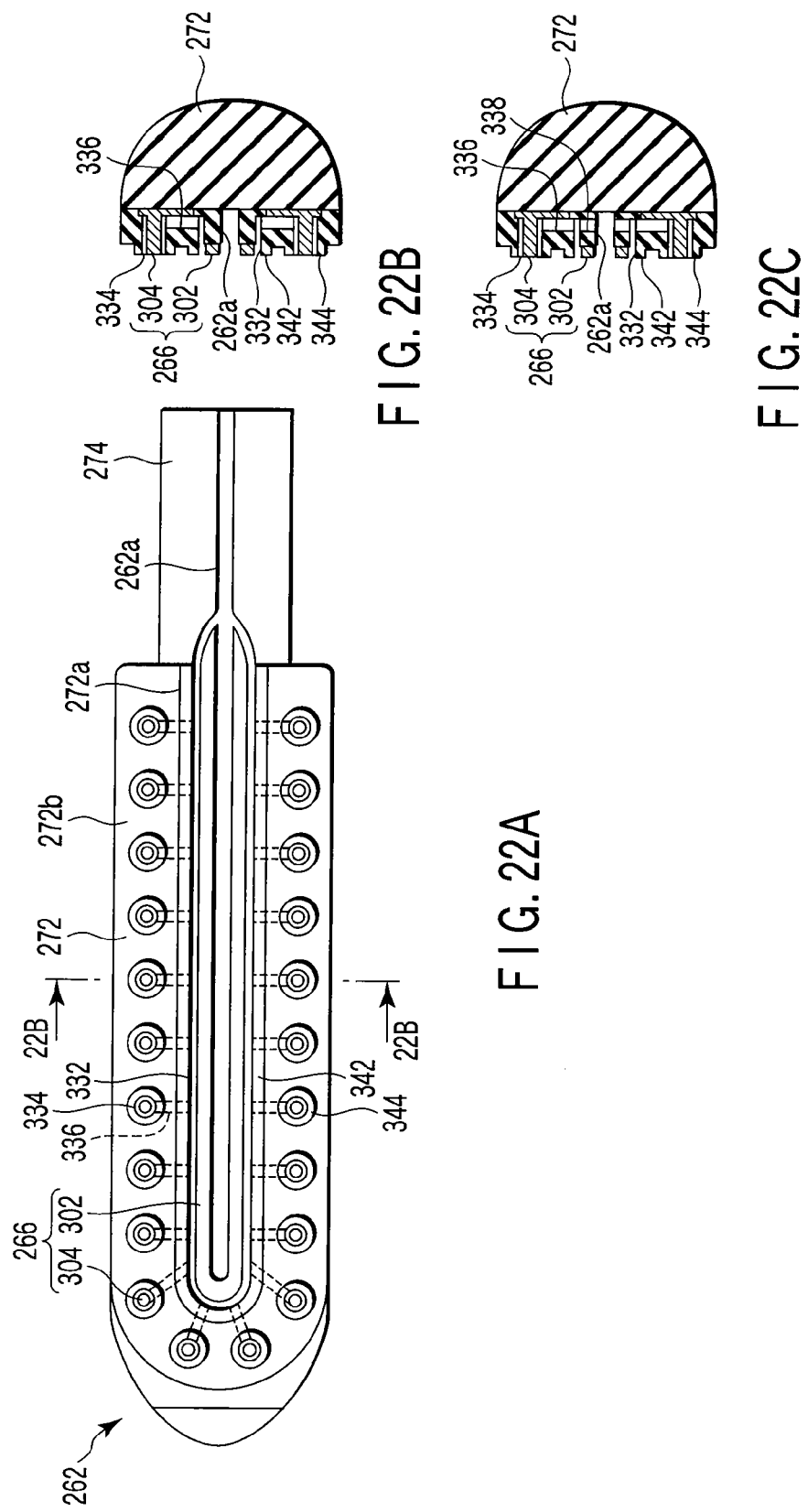

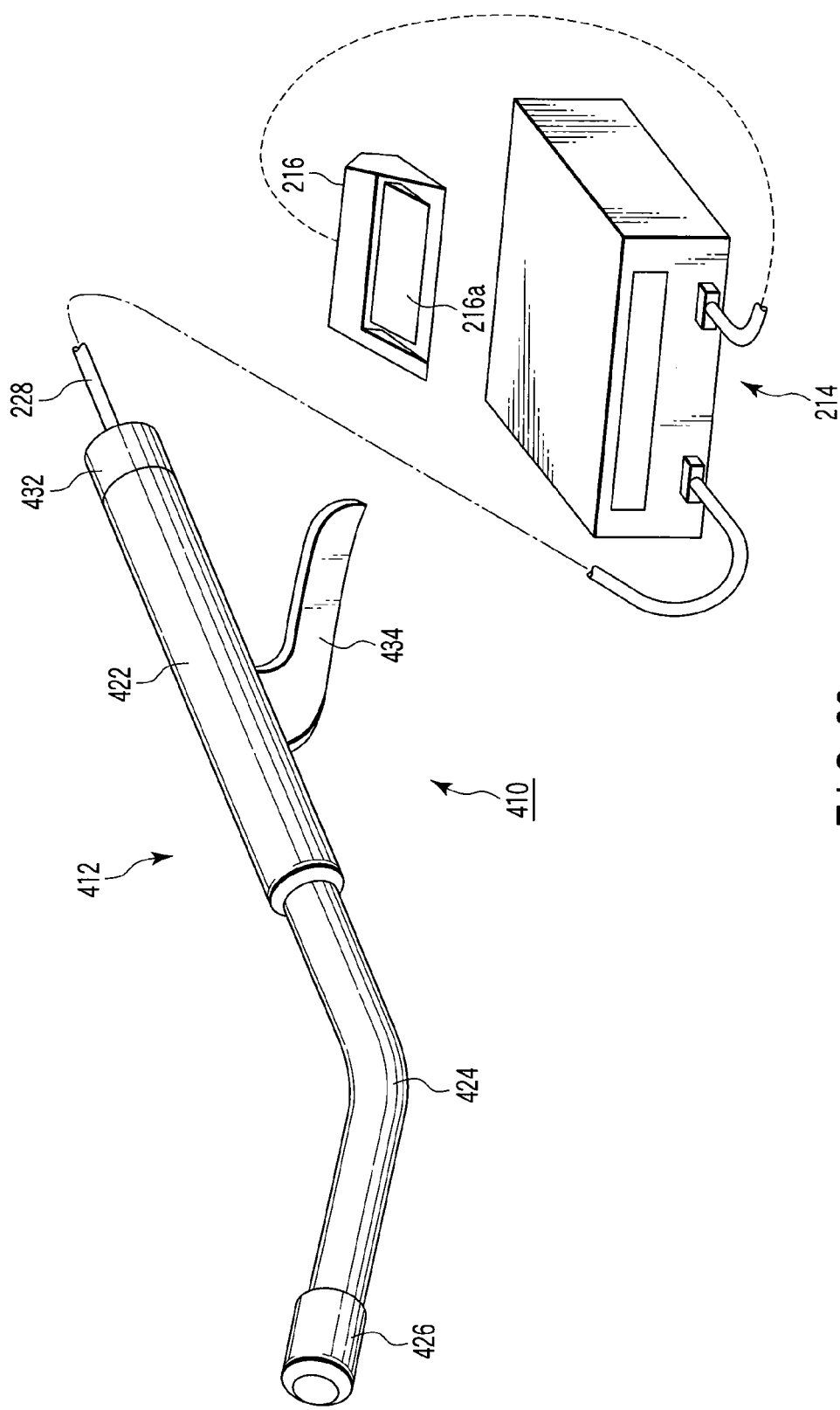
F I G. 23

TREATMENT SYSTEM, AND TREATMENT METHOD FOR LIVING TISSUE USING ENERGY

BACKGROUND OF THE INVENTION

1. Field of the Invention

The present invention relates to a treatment system for treating a living tissue by use of energy, and a treatment method for a living tissue using energy.

2. Description of the Related Art

In US Patent Application Publication No. US2005/0113828 A1, an electrosurgical instrument is disclosed in which a living tissue is held between a pair of openable/closable jaws, and a high-frequency current is applied between the pair of jaws holding the living tissue therebetween to denature the held living tissue. Here, in the electrosurgical instrument, high-frequency energy flows thorough the living tissue to immediately denature the inside of the tissue by use of Joule heat generated in the living tissue. Then, the electrosurgical instrument immediately destroys cell membranes to release, from the destroyed cell membranes, an intracellular fluid including polymer compounds typified by protein, and homogenizes (liquefies) intracellular components with extracellular components typified by collagen. Such homogenization can result in the mutual bonding of bonding faces of the living tissues and the mutual bonding of interlayers of the tissues. It is to be noted that when the high-frequency energy is applied to the living tissue, the state (impedance or phase information) of the living tissue can be detected. In general, there are characteristics that as the impedance of the held living tissue is high, the output of the high-frequency energy which can be applied to the living tissue decreases.

In Jpn. Pat. Appln. KOKAI Publication No. 2001-190561, a coagulation treatment instrument is disclosed in which a pair of openable/closable jaws are provided with a ceramic heater. In the ceramic heater, a heating element is embedded, and when a power is supplied through the heating element, the ceramic heater generates heat. Then, the heat of the ceramic heater is conducted to the living tissue held between the pair of jaws to coagulate the living tissue. At this time, if the heat is generated at a set temperature from the heating element, the heat energy can uniformly be applied to the living tissue regardless of the state of the living tissue. Therefore, the desired output can uniformly be performed, even in a state in which the high-frequency energy cannot sufficiently be output to the living tissue in the treatment using the high-frequency energy, for example, after the impedance of the living tissue rises.

BRIEF SUMMARY OF THE INVENTION

According to a first aspect of the present invention, there is provided a treatment system which exerts energy to a living tissue to treat the living tissue, including:

a pair of holding members which hold the living tissue therebetween, at least one of the holding members being configured to relatively move with respect to the other holding member and to hold the living tissue;

a high-frequency energy output section which is provided on at least one of the holding members and which exerts high-frequency energy to the living tissue to denature the living tissue and which collects the biological information of the living tissue held between the holding members;

a heat generating section which is provided on at least one of the holding members and which applies heat to the living tissue held between the holding members, the heat generating section being configured to generate the heat owing to the supply of the energy and to conduct the heat therefrom, thereby denaturing the living tissue; and a control section which controls the output of the energy to the high-frequency energy output section and the heat generating section based on the biological information collected by the high-frequency energy output section.

According to a second aspect of the present invention, there is provided a treatment system including:

a treatment instrument including a treatment section having electrodes to which a high-frequency power is to be supplied and a heat generation element, the treatment section being able to hold a living tissue;

a high-frequency driving circuit which supplies a high-frequency power to the electrodes to treat the living tissue held by the treatment section with high-frequency energy and which collects information obtained from the living tissue through the electrodes;

a heat generation element driving circuit which supplies a heat generation power to the heat generation element to treat the living tissue held by the treatment section owing to the function of heat and which collects temperature information transmitted to the living tissue through the heat generation element; and a control section which controls the high-frequency driving circuit and the heat generation element driving circuit based on the information collected by the high-frequency driving circuit and/or the heat generation element driving circuit.

According to a third aspect of the present invention, there is provided a treatment method which exerts energy to a living tissue to treat the living tissue, including:

holding the living tissue;

applying high-frequency energy to the held living tissue and obtaining the biological information of the living tissue; and applying heat to the living tissue based on the biological information of the living tissue.

According to a fourth aspect of the present invention, there is provided a treatment method which exerts energy to a living tissue to treat the living tissue, including:

heating the living tissue at a first temperature;

applying high-frequency energy to the living tissue and obtaining the biological information of the living tissue; and switching the first temperature to a second temperature which is different from and higher than the first temperature to heat the living tissue, based on the biological information of the living tissue.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic block diagram showing the treatment system according to the first embodiment;

FIG. 9 is a schematic diagram showing a treatment system according to a second embodiment of the present invention;

FIG. 10A is a schematic vertical sectional view showing a shaft of an energy treatment instrument and a state where a first holding member and a second holding member of a holding section are closed in the treatment system according to the second embodiment;

FIG. 10B is a schematic vertical sectional view showing the shaft of the energy treatment instrument and a state where a first holding member and a second holding member of a holding section are opened in the treatment system according to the second embodiment;

FIG. 16 is a schematic diagram showing a modification of the treatment system according to the second embodiment;

FIG. 19A is a schematic plan view showing a first holding member on a side close to a second holding member in a holding section of a surgical treatment instrument according to a third modification of the second embodiment;

FIG. 19B is a schematic vertical sectional view showing the first holding member cut along the 19B-19B line of FIG. 19A in the holding section of the surgical treatment instrument according to the third modification of the second embodiment;

FIG. 19C is a schematic transverse sectional view showing the first holding member cut along the 19C-19C line of FIG. 19A in the holding section of the surgical treatment instrument according to the third modification of the second embodiment;

FIG. 19D is a schematic plan view showing a first holding member on a side close to a second holding member in a holding section of a surgical treatment instrument according to a further modification of the third modification of the second embodiment;

FIG. 21A is a schematic plan view showing a first holding member on a side close to a second holding member in a holding section of a surgical treatment instrument according to a fourth modification of the second embodiment;

FIG. 21B is a schematic plan view showing the first holding member on the side close to the second holding member in the holding section of the surgical treatment instrument according to the fourth modification of the second embodiment;

FIG. 21C is a schematic plan view showing the first holding member on the side close to the second holding member in the holding section of the surgical treatment instrument according to the fourth modification of the second embodiment;

FIG. 22A is a schematic plan view showing the first holding member on the side close to the second holding member in the holding section of the surgical treatment instrument according to a fifth modification of the second embodiment;

FIG. 22B is a schematic transverse sectional view cut along the 22B-22B line of FIG. 22A and showing the first holding member in the holding section of the surgical treatment instrument according to the fifth modification of the second embodiment;

FIG. 22C is a schematic transverse sectional view cut along the 22B-22B line of FIG. 22A and showing a first holding member in a holding section of a surgical treatment instrument according to a further modification of the fifth modification of the second embodiment;

FIG. 23 is a schematic diagram showing a modification of a treatment system according to a third embodiment;

DETAILED DESCRIPTION OF THE INVENTION

The best mode for carrying out this invention will hereinafter be described with reference to the drawings.

First Embodiment

A first embodiment will be described with reference to FIGS. 1 to 5.

Figure 1:
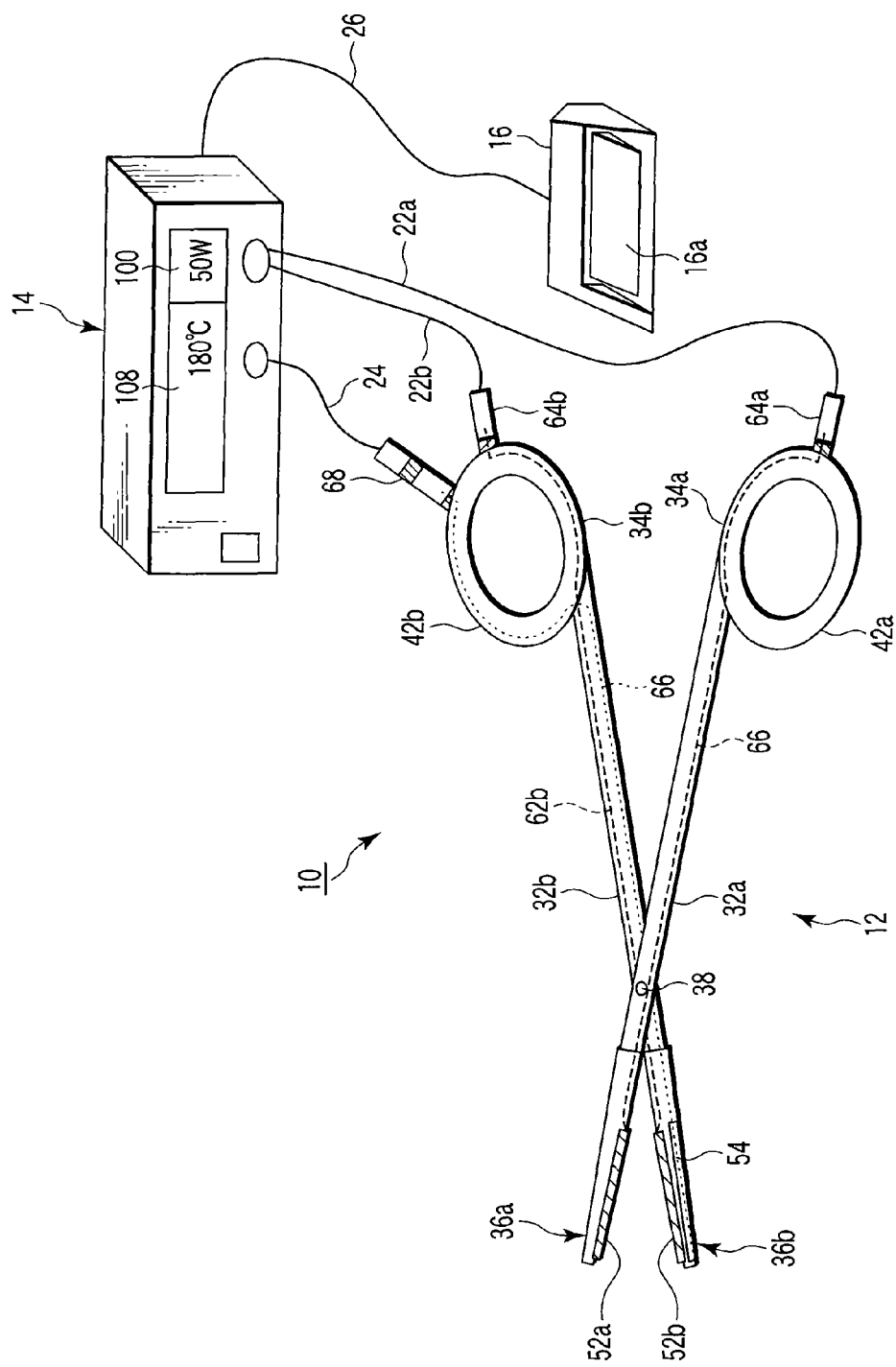
FIG. 1 is a schematic diagram showing a treatment system according to a first embodiment of the present invention.

As shown in FIG. 1, a treatment system 10 includes a surgical treatment instrument (a treatment instrument) 12, an energy source 14 and a foot switch 16. The surgical treatment instrument 12 is connected to the energy source 14 via, for example, a pair of connection cables 22a, 22b for high-frequency energy output, and one connection cable 24 for heat energy output. The foot switch 16 is connected to the energy source 14 via a connection cable 26 for the switch.

The surgical treatment instrument 12 includes a pair of scissor constituting members 32a, 32b; a pair of handle sections 34a, 34b which are provided on the proximal ends of the scissor constituting members 32a, 32b and which are to be manually held and operated by an operator; and a pair of jaws (holding members, treatment sections) 36a, 36b which are provided on the distal ends of the scissor constituting members 32a, 32b and which hold a living tissue $L_T$ to be treated to perform a treatment such as coagulation or incision.

The pair of scissor constituting members 32a, 32b are superimposed so that the members substantially intersect with each other between the distal ends of the members and the proximal ends thereof. An intersecting portion between the scissor constituting members 32a and 32b is provided with a support pin 38 which rotatably connects the scissor constituting members 32a, 32b to each other.

The pair of handle sections 34a, 34b are provided with rings 42a, 42b to be held with operator's fingers. When the operator holds the rings 42a, 42b with operator's thumb and middle finger, respectively, to perform an opening/closing operation, the jaws 36a, 36b open/close in conjunction with the operation.

The pair of jaws 36a, 36b are provided with energy release elements for applying energy to the living tissue $L_T$. One jaw 36a is provided with a first high-frequency electrode 52a as the energy release element. The other jaw 36b is provided with a second high-frequency electrode 52b and a heater member 54 as the energy release elements. Among these elements, the heater member (a heat generation element) 54 is embedded in the other jaw 36b in a state in which the member is fixed to the back surface of the second high-frequency electrode 52b.

Thus, in the pair of jaws 36a, 36b, the first and second high-frequency electrodes 52a, 52b include conductive tissue holding faces (tissue grasping faces). It is to be noted that the heater member 54 is provided with a thin film resistance and a thick film resistance as heat generation patterns. The thin film resistance is formed by a thin film formation process such as physical vapor deposition (PVD) and chemical vapor deposition (CVD). The thick film resistance is formed by a thick film formation process such as screen printing. The heat generation pattern is formed of a high melting metal such as molybdenum having a so-called positive temperature coefficient such that an electric resistance increases in proportion to a temperature.

In the pair of scissor constituting members 32a, 32b, power supply lines 62a, 62b for supplying electric signals to the electrodes 52a, 52b are arranged, respectively. The power supply lines 62a, 62b extend from the jaws 36a, 36b to the handle sections 34a, 34b, respectively. The rings 42a, 42b are provided with bipolar terminals 64a, 64b, respectively. The bipolar terminals 64a, 64b are electrically connected to the power supply lines 62a, 62b, respectively. Therefore, in a case where the energy is supplied to the electrodes 52a, 52b through the power supply lines 62a, 62b in a state in which the living tissue $L_T$ is held between the jaws 36a and 36b (between the electrodes 52a and 52b), a high-frequency current is supplied through the living tissue $L_T$ between the electrodes 52a and 52b, whereby the living tissue $L_T$ generates heat.

In the other scissor constituting member 32b of the pair of scissor constituting members 32a, 32b, a power supply line 66 for supplying a power to the heater member 54 is provided. The power supply line 66 extends from the jaw 36b to the handle section 34b. The ring 42b is provided with a heater member terminal 68 electrically connected to the power supply line 66. Therefore, when the energy is supplied to the heater member 54 through the power supply line 66, the heater member 54 generates heat, and the heat (heat energy) is conducted to the second high-frequency electrode 52b which comes in close contact with the heater member 54, and is transmitted to the living tissue $L_T$ which comes in contact with the front surface of the second high-frequency electrode 52b.

According to such a structure, the heater member 54 is provided on at least one of the pair of jaws 36a, 36b which are supported openably/closably to grasp the living tissue $L_T$ (it is also preferable to provide the heat members on both of the jaws), and the heater member functions as heat generation means capable of applying the heat energy for coagulating the living tissue $L_T$ grasped between the jaws 36a and 36b.

Therefore, the surgical treatment instrument 12 can supply the high-frequency current between these electrodes 52a and 52b to apply the high-frequency energy to the living tissue $L_T$ grasped between the jaws 36a and 36b. Moreover, the energy is applied to the heater member 54 to generate the heat therefrom, whereby the heat energy obtained by the heat generation of the heater member 54 can be transmitted to the living tissue $L_T$ through the second electrode 52b to treat the tissue.

It is to be noted that the foot switch 16 includes a pedal 16a. When the pedal 16a is pressed, the high-frequency energy and/or the heat energy is output based on an appropriately set state (a state in which an energy output amount, an energy output timing or the like is controlled). When the pressed pedal 16a is released, the output of the high-frequency energy and heat energy is forcibly stopped.

As shown in FIG. 2, a high-frequency energy driving circuit 72 and a heat generation element driving circuit 74 are arranged in the energy source 14. The high-frequency energy driving circuit 72 and the heat generation element driving circuit 74 are connected to the energy source 14 via a communication cable 82.

The high-frequency energy driving circuit 72 includes an output control section 92; a variable voltage source (SW power source) 94 which supplies a power for outputting and controlling the high-frequency energy; a power amplifier (AMP) 96 which amplifies a high-frequency power and which shapes an output waveform; a sensor 98 which monitors the high-frequency energy output (a voltage value and a current value); and an operation display panel (setting means of the output control section 92) 100. Among these components, the variable voltage source (SW power source) 94, the power amplifier 96 and the sensor 98 are successively connected in series. The sensor 98 is connected to the surgical treatment instrument 12 via the connection cables 22a, 22b for the high-frequency energy output. The output control section 92 is connected to the variable voltage source 94, the power amplifier 96 and the sensor 98. Furthermore, the output control section 92 is connected to the operation display panel 100. The operation display panel 100 displays a high-frequency energy output amount monitored by the sensor 98 through the electrodes 52a, 52b, and the output control section 92 sends control signals to the variable voltage source 94 and the electrode amplifier 96 based on a monitor signal from the sensor 98. Thus, the high-frequency output is controlled.

Therefore, while the power supplied from the variable voltage source 94 and amplified by the power amplifier 96 is controlled by the output control section 92, the power is transmitted from the sensor 98 to the electrodes 52a, 52b of the surgical treatment instrument 12 via the connection cables 22a, 22b for the high-frequency energy output.

The heat generation element driving circuit 74 includes an output control section 102 for the heat generation element driving circuit, an output section 104, a sensor 106 and an operation display panel 108. The output section 104 supplies a power (energy) for allowing the heater member 54 to generate heat. The sensor 106 monitors the value of the output to the heater member 54 (a voltage value, a current value), and sends a monitor signal to the output control section 102. The output control section 102 calculates various parameters such as a voltage, a current, a power and a resistance value based on the monitor signal from the sensor 106.

It is to be noted that the heat generation pattern of the heater member 54 has a positive temperature coefficient. Therefore, the output control section 102 can further calculate a temperature T of the heater member 54 from the calculated resistance value. The output control section 102 sends a control signal to the output section 104 based on the calculation results of the parameters. Therefore, the output control of the heater member 54 is performed.

The output control section 92 of the high-frequency energy driving circuit 72 is connected to the output control section 102 of the heat generation element driving circuit 74 via the communication cable 82 capable of bidirectionally transmitting signals. The output control section 92 of the high-frequency energy driving circuit 72 sends the ON/OFF signal of the foot switch 16 to the output control section 102 of the heat generation element driving circuit 74. The output control section 92 of the high-frequency energy driving circuit 72 sends, to the output control section 102 of the heat generation element driving circuit 74, a signal indicating the magnitude of an impedance (an impedance in a state in which the living tissue $L_T$ is held between the electrodes 52a and 52b) Z during the output of the high-frequency energy calculated based on the monitor signal (the voltage value, the current value) of the sensor 98. It is to be noted that the impedance Z is calculated by the output control section 92 based on the monitor signal from the sensor 98. Therefore, the electrodes 52a, 52b and the high-frequency energy driving circuit 72 are high-frequency energy output sections for use in exerting the high-frequency energy to the living tissue $L_T$ grasped between the jaws 36a and 36b to denature the living tissue $L_T$ and collecting the impedance information Z (biological information) of the living tissue $L_T$.

The output control section 102 of the heat generation element driving circuit 74 sends, to the output control section 92 of the high-frequency energy driving circuit 72, a signal indicating the temperature T of the heater member 54 calculated based on the monitor signal (the voltage value, the current value) of the sensor 106. The operation display panel 100 of the high-frequency energy driving circuit 72 is connected to the operation display panel 108 of the heat generation element driving circuit 74 via the output control section 92 of the high-frequency energy driving circuit 72, the communication cable 82 and the output control section 102 of the heat generation element driving circuit 74. Therefore, the settings and display contents of the operation display panels 100, 108 are associated with each other.

Figure 3A:
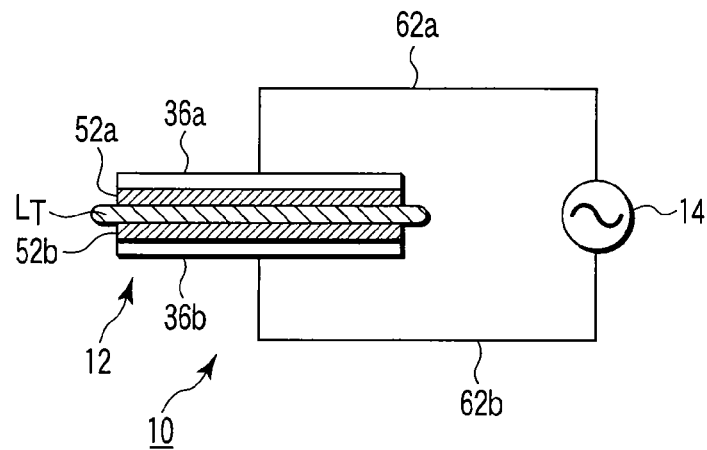
FIG. 3A is a schematic diagram showing the treatment system according to the first embodiment in a case where high-frequency energy is applied to a living tissue to treat the tissue with a bipolar surgical treatment instrument.

As described above, the surgical treatment instrument 12 of the embodiment functions as a bipolar high-frequency treatment instrument as shown in FIGS. 2 and 3A, and functions as the treatment instrument for the heat generation as shown in FIG. 2.

A method for using the treatment system 10 (an operation) will hereinafter be described.

An operator operates the operation display panels (setting means) 100, 108 before the treatment of a patient, to input and set, into the output control sections 92, 102, the output conditions (a set power Pset[W] of the high-frequency energy output, a set temperature Tset [° C.] of the heat energy output, threshold values Z1, Z2 of the impedance Z of the living tissue $L_T$, etc.) of the surgical treatment instrument 12. The threshold value Z1 is preferably set in a state in which when the drying of the living tissue $L_T$ proceeds and the value of the impedance Z rises, the high-frequency energy output lowers, and appropriate energy cannot be introduced, or a state slightly previous to this state. On such conditions, the threshold value Z1 is set to an empirically appropriate value. With regard to the threshold value Z2, on such conditions that the drying of the living tissue $L_T$ further proceeds, the threshold value Z2 is set to an empirically appropriate value. It is to be noted that the threshold values Z1, Z2 may be incorporated in a program stored in the output control section 92 in advance, and does not necessarily have to be set by the operator.

It is to be noted that with regard to a relation between the threshold values Z1 and Z2 of the impedance Z, the threshold value Z2 is larger than the threshold value Z1. The threshold value Z1 is preferably, for example, about 500 [Ω] to 1500 [Ω], and the threshold value Z2 is preferably about 2000 [Ω] to 3000 [Ω]. It is also preferable that the threshold values Z1, Z2 are set within predetermined ranges (e.g., the threshold value Z1 is in a range of 500 [Ω] to 1500 [Ω], and the threshold value Z2 is in a range of 2000 [Ω] to 3000 [Ω]) and that values out of the predetermined ranges cannot be set.

The operator holds with fingers the rings 42a, 42b of the handle sections 34a, 34b of the surgical treatment instrument 12, and operates the surgical treatment instrument 12 to peel, from a peripheral living tissue, the living tissue $L_T$ to be subjected to a treatment such as coagulation or incision. Thus, the holding of the living tissue $L_T$ as a treatment target is facilitated. Then, the living tissue $L_T$ is held and grasped between the jaws 36a and 36b.

Subsequently, the operator performs an operation of pressing the pedal 16a of the foot switch 16, while maintaining a state in which the living tissue $L_T$ is held between the jaws 36a and 36b. In consequence, the treatment is performed using the high-frequency energy applied to the living tissue $L_T$ between the electrodes 52a and 52b of the jaws 36a and 36b of the surgical treatment instrument 12, or the heat energy transmitted through the electrode 52a from the heater member 54 which has generated the heat from the energy applied to the heater member 54.

Figure 4:
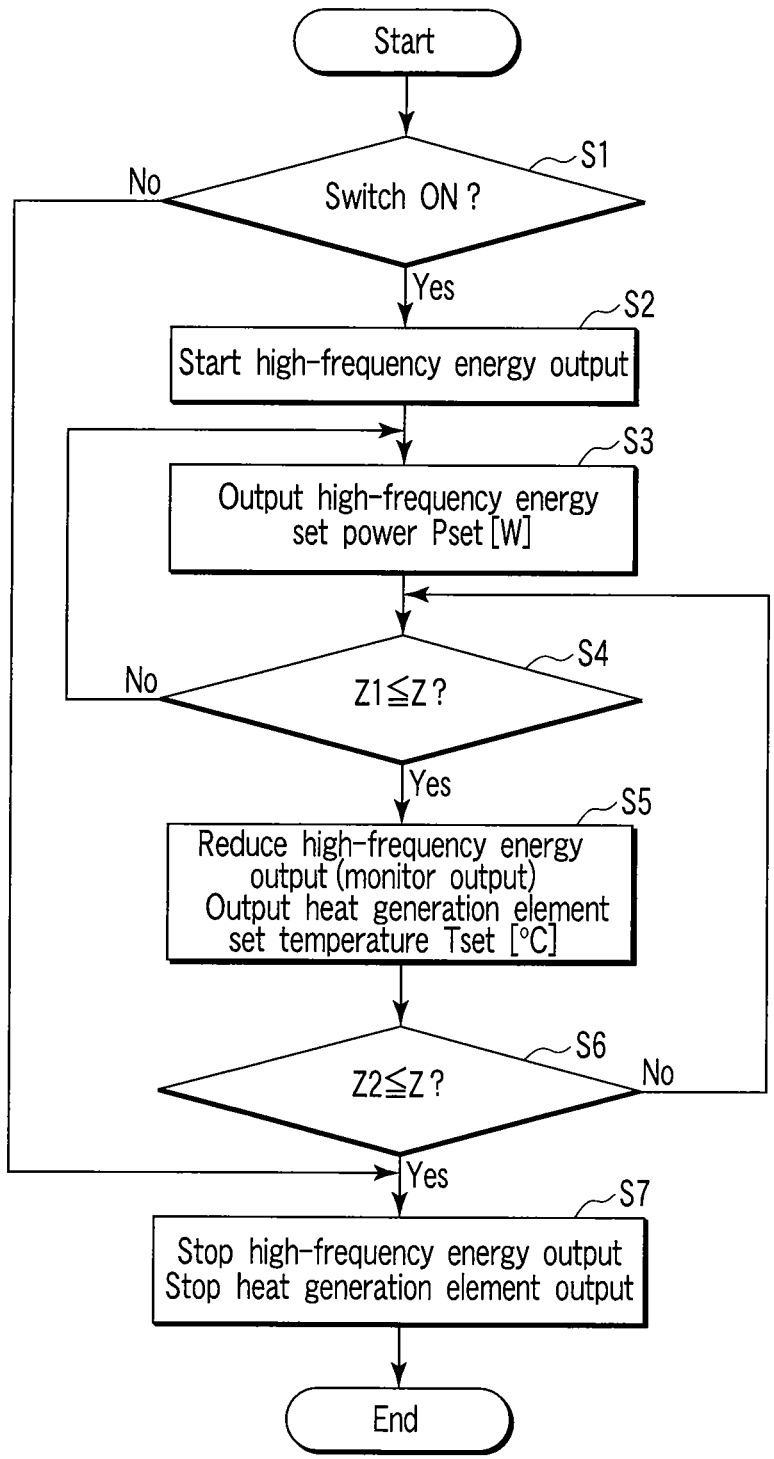
FIG. 4 is a schematic flow chart showing a case where a treatment using the high-frequency energy and a treatment using heat energy are performed with respect to the living tissue by use of the treatment system according to the first embodiment.

FIG. 4 shows one example of the control flow of the surgical treatment instrument 12 controlled by the high-frequency energy driving circuit 72 and the heat generation element driving circuit 74.

First, the output control section 92 of the high-frequency energy output circuit 72 judges whether or not the pedal 16a of the foot switch 16 has been pressed by operator's operation based on the signal from the switch 16, that is, whether or not the switch has been turned on (STEP 1).

In a case where the output control section 92 judges that the switch 16 has been turned on, the output control section outputs the high-frequency energy between the electrodes 52a and 52b of the jaws 36a and 36b of the surgical treatment instrument 12 from the variable voltage source 94 of the high-frequency energy driving circuit 72 via the power amplifier 96, the sensor 98 and the connection cables 22a, 22b for the high-frequency energy output (STEP 2). At this time, the output control section supplies the set power Pset [W] preset by the operation display panel 100, that is, a power of, for example, about 20 [W] to 80 [W] between the electrodes 52a and 52b of the jaws 36a and 36b (STEP 3).

Therefore, the first high-frequency electrode 52a supplies a high-frequency current between the first high-frequency electrode 52a and the second high-frequency electrode 52b via the living tissue $L_T$ as the treatment target. That is, the high-frequency energy is applied to the living tissue $L_T$ grasped between the electrodes 52a and 52b. Therefore, Joule heat is generated in the living tissue $L_T$ grasped between the electrodes 52a and 52b to heat the living tissue $L_T$ itself. A cell membrane in the living tissue $L_T$ held between the electrodes 52a and 52b is destroyed owing to the function of the high-frequency voltage and the function of the Joule heat to release substances from the cell membrane, and the tissue is homogenized with extracellular components including collagen. The high-frequency current is supplied through the living tissue $L_T$ between the electrodes 52a and 52b, so that further Joule heat acts on the tissue $L_T$ homogenized in this manner, and, for example, the bonding faces of the living tissue $L_T$ or the layers of the tissue are bonded to each other. Therefore, when the high-frequency current is supplied between the electrodes 52a and 52b, the living tissue $L_T$ itself generates the heat and is dehydrated, while the inside of the living tissue $L_T$ is denatured (the living tissue $L_T$ is cauterized).

Figure 5A:
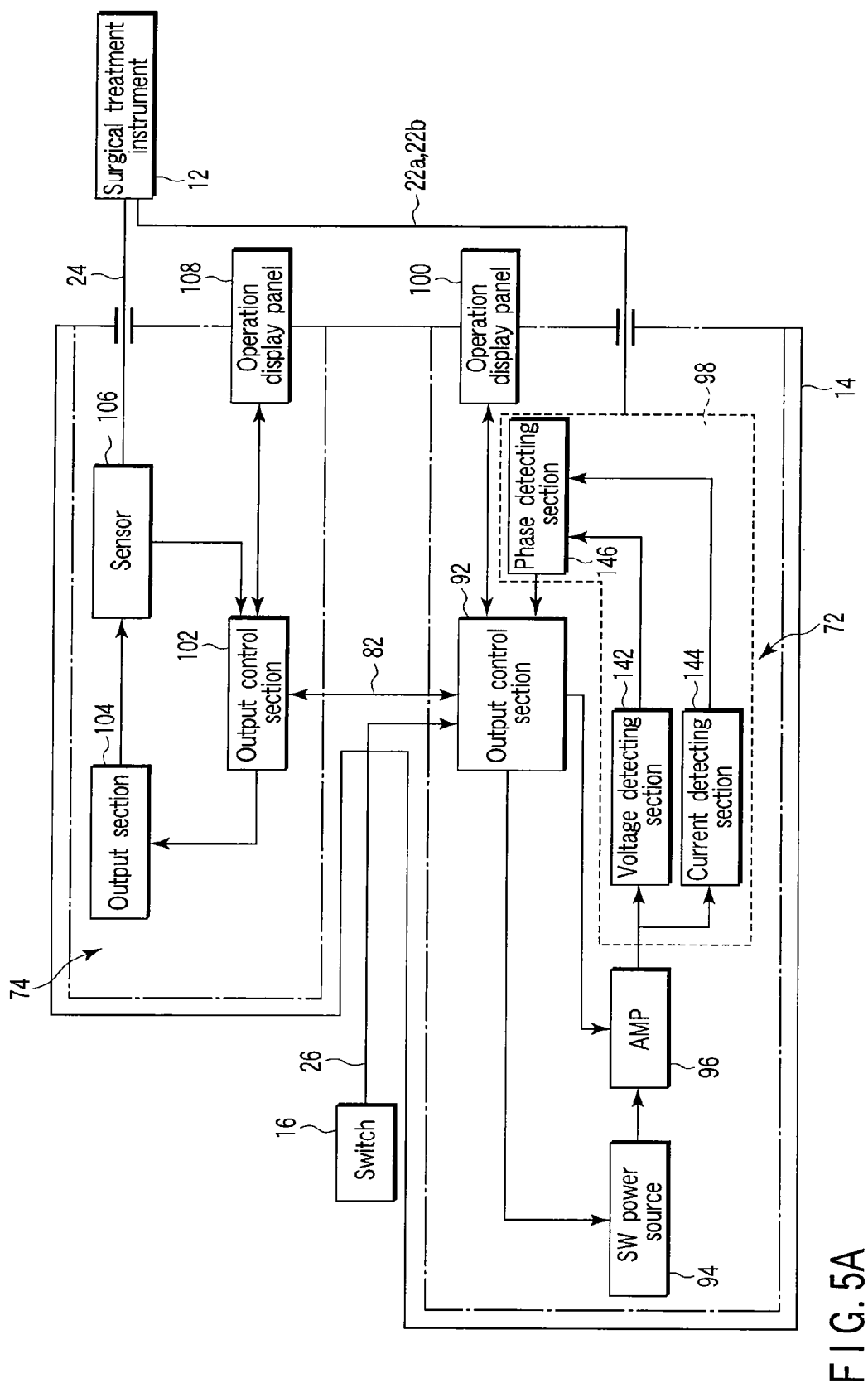
FIG. 5A is a schematic block diagram showing a treatment system according to a first modification of the first embodiment.
Figure 5:
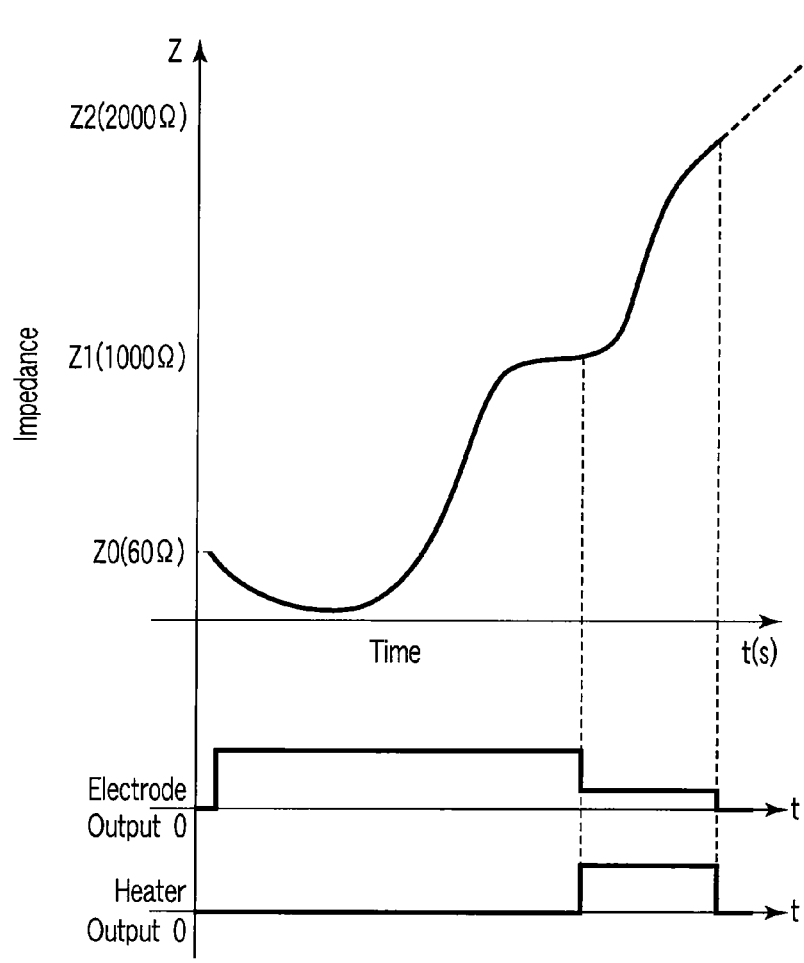
FIG. 5 is a schematic graph showing a relation between impedance and time in a case where the treatment using the high-frequency energy and the treatment using the heat energy are performed with respect to the living tissue by use of the treatment system according to the first embodiment.

At this time, the impedance Z of the living tissue $L_T$ held between the electrodes 52a and 52b is measured by the sensor (collection means for collecting the biological information) 98 through the electrodes 52a, 52b. An impedance Z0 at a time of treatment start changes in accordance with the sizes or shapes of the electrodes, but as shown in FIG. 5, the impedance is, for example, about 60 [Ω]. Subsequently, when the high-frequency current is supplied through the living tissue $L_T$ to cauterize the living tissue $L_T$, the value of the impedance Z once lowers and then rises. Such rise of the value of the impedance Z indicates that a water content is removed from the living tissue $L_T$ and that the tissue progressively dries.

Subsequently, the output control section 92 judges whether or not the value of the impedance Z during the high-frequency energy output calculated based on the signal from the sensor 98 exceeds the preset threshold value Z1 (here, about 1000 [Ω] as shown in FIG. 5) (STEP 4). As the threshold value Z1, there is selected a value or so which has empirically been known and at which the rise ratio of the value of the impedance Z becomes dull at a time when a predetermined power is input. Then, in a case where the output control section 92 judges that the value of the impedance Z is smaller than the threshold value Z1, processing is returned to STEP 3. That is, the high-frequency energy for the treatment is continuously applied to the living tissue $L_T$ held between the electrodes 52a and 52b of the jaws 36a and 36b.

On the other hand, in a case where the output control section 92 judges that the value of the impedance Z is the threshold value Z1 or more, the output control section 92 reduces the high-frequency energy output supplied to the electrodes 52a, 52b, and switches the output to monitor output (STEP 5).

Here, the monitor output is the output of a weak high-frequency current having such a level that the living tissue $L_T$ is not treated. Owing to such monitor output, the change of the impedance Z of the living tissue $L_T$ between the jaws 36a and 36b can continuously be monitored with the sensor 98 through the electrodes 52a, 52b.

Subsequently, in a case where the output control section 92 judges that the value of the impedance Z is the threshold value Z1 or more, a signal is transmitted from the output control section 92 of the high-frequency energy driving circuit 72 to the output control section 102 of the heat generation element driving circuit 74 via the communication cable 82. Then, the output control section 102 of the heat generation element driving circuit 74 supplies the power (the energy) to the heater member 54 so that the temperature of the heater member 54 is a preset temperature Tset [° C.], for example, a temperature of 100 [° C.] to 300 [° C.] (STEP 5). In consequence, the heater member 54 generates heat. The heat is conducted from the heater member 54 to the second electrode 52b, and the heat (the heat energy) conducted to the second electrode 52b coagulates the living tissue $L_T$ internally from the side of the front surface of the living tissue $L_T$ which comes in contact with the second electrode 52b. At this time, the living tissue (protein) is integrally denatured, and the water content as a factor for disturbing the mutual bonding of proteins is removed. The high-frequency energy is substantially simultaneously switched to the heat energy, and the cell membrane is destroyed by the high-frequency energy, whereby thermal conductivity improves, and hence the heat can more efficiently be conducted from the heater member 54 to the living tissue.

Subsequently, the output control section 92 judges whether the impedance Z of the living tissue $L_T$ monitored in accordance with the monitor output is the preset threshold value Z2 (here, about 2000 [Ω] as shown in FIG. 5) or more (STEP 6). In a case where it is judged that the impedance Z is smaller than the threshold value Z2, the processing is returned to STEP 4. On the other hand, in a case where it is judged that the value of the impedance Z exceeds the threshold value Z2, the output control sections 92, 102 stop the output of the high-frequency energy and heat energy (STEP 7). Then, the treatment of the living tissue $L_T$ by use of the treatment system 10 is ended.

It is to be noted that while a series of treatments to output the high-frequency energy and the heat energy in this manner are performed, the pedal 16a of the foot switch 16 is depressed. When the depressed pedal 16a is released during the treatment, the output of the high-frequency energy and heat energy is forcibly stopped.

As described above, according to this embodiment, the following effect is obtained.

The high-frequency energy is introduced into the living tissue $L_T$ held between the electrodes 52a and 52b to generate the Joule heat in the living tissue $L_T$, whereby the cell membrane is destroyed to homogenize intracellular and extracellular components, and the tissue is cauterized, whereby the impedance Z can be raised. Then, the living tissue $L_T$ into which the high-frequency energy is introduced to destroy the cell membrane and raise the thermal conductivity can be subjected to a coagulation treatment using the heat energy conducted from the heater member 54 allowed to generate the heat.

At this time, the state (the impedance Z or the temperature T) of the living tissue $L_T$ held between the jaws 36a and 36b is monitored, and a time to switch the introduction of the energy from the introduction of the high-frequency energy to the introduction of the heat energy can automatically be judged and switched in accordance with the preset threshold value Z1 of the impedance Z. In consequence, a series of operations of switching the treatment using the high-frequency energy to the treatment using the heat energy can be realized, so that the treatment can efficiently be performed.

That is, the change of the impedance Z of the high-frequency energy output is measured with the sensor 98 of the high-frequency energy driving circuit 72, and appropriate treatments (the treatment using the high-frequency energy and the treatment using the heat energy) can be performed based on the measured value. Therefore, the threshold values Z1, Z2 are measured in this manner, whereby the operator can perform the treatment in accordance with the tissue denatured state of the living tissue $L_T$ by use of the surgical treatment instrument 12, and the fluctuation of the treatment due to operator's sense can be prevented to homogenize (stabilize) the tissue.

Therefore, in a case where the high-frequency energy is combined with the heat conduction from the heat energy to treat the living tissue $L_T$ grasped between the jaws 36a and 36b in a state in which the introduction timing of the high-frequency energy and heat energy is controlled, the living tissue can efficiently and stably be denatured (the tissue can be cauterized and/or coagulated, etc.). The treatment is performed in this manner, whereby the living tissue $L_T$ can be treated in a state in which loss during the introduction of the energy is minimized, and treatment time can be reduced. Therefore, a burden imposed on the patient can largely be reduced.

The pedal 16a of the foot switch 16 is simply pressed in a state in which the living tissue $L_T$ is held between the electrodes 52a and 52b of the jaws 36a and 36b, whereby both the treatment using the high-frequency energy and the treatment using the heat energy can automatically be performed without being laboriously switched. That is, treatment conditions such as the output Pset, the temperature Tset and the threshold values Z1, Z2 of the impedance Z are set in accordance with the type and state of the living tissue $L_T$ in the display panels 100, 108, and the living tissue $L_T$ as the treatment target is grasped. Afterward, the pedal 16a of the switch 16 simply continues to be pressed, whereby the treatment can be performed without requiring any operator's sense. Subsequently, when the threshold value Z2 exceeds the set value, in a state in which the treatment of the living tissue $L_T$ is prevented from being excessively performed, the treatment can automatically be ended without requiring any artificial switching between the treatment using the high-frequency energy and the treatment using the heat energy. Therefore, the burden imposed on the operator during the treatment can largely be reduced.

It is to be noted that the threshold value Z1 is the rise value, but the timing to switch to the heat energy may be set to the lowermost point or so of the impedance at which the destruction of the cell membrane substantially ends.

Moreover, in this embodiment, the treatment has been described in which the high-frequency energy is introduced into the living tissue $L_T$, and then the heat energy is applied. However, the heat energy may be introduced simultaneously with or prior to the high-frequency energy to such an extent that the denaturation of the protein is not caused. However, it is not appropriate to supply the heat energy which causes the protein denaturation (the denaturation, coagulation or the like of the surface tissue) before supplying the treatment high-frequency energy for treating the living tissue, because the appropriate high-frequency energy is not easily introduced into the living tissue.

Furthermore, in this embodiment, it is judged in STEP 6 of FIG. 4 whether the value of the impedance Z is the threshold value Z2 or more, and the output of the high-frequency energy and heat energy is stopped. Separately, with the elapse of time after shifting to STEP 5, for example, with the elapse of 30 seconds (predetermined time t) after starting the output of the heat generation element set temperature Tset [° C.] in STEP 5, the output of the high-frequency energy and heat energy may automatically be stopped. That is, instead of judging the change of the impedance Z, it is preferable to switch the treatment from the treatment using the high-frequency energy to the treatment using the heater member 54 after the elapse of the predetermined time t or to set the state of the treatment by use of the display panels 100, 108 in accordance with the elapse of time so that the treatment is ended. It is further preferable to set both the impedance Z and the time by use of the display panels 100, 108 so that one of the impedance and the time whose treatment earlier ends is appropriately selected. The treatment may be ended, for example, at a time when the value of the impedance Z reaches the threshold value Z2 before the predetermined time t elapses, or the treatment may be ended at a time when the predetermined time t elapses before the value of the impedance Z reaches the threshold value Z2.

Figure 3B:
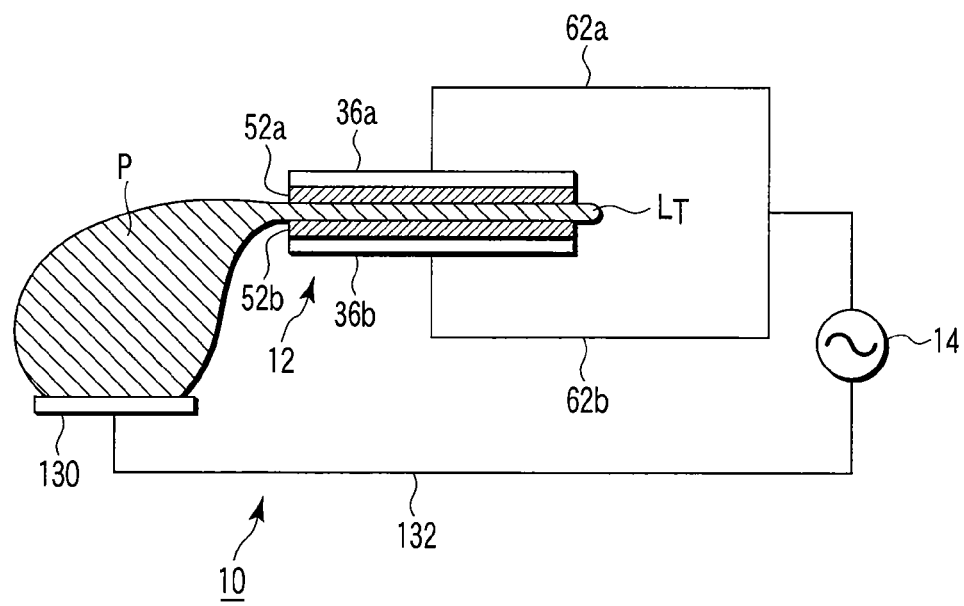
FIG. 3B is a schematic diagram showing the treatment system according to the first embodiment in a case where high-frequency energy is applied to the living tissue to treat the tissue with a monopolar surgical treatment instrument.

Here, it has been described that as shown in FIG. 3A, the bipolar surgical treatment instrument 12 having the electrodes 52a, 52b provided on the jaws 36a, 36b, respectively, and having different potentials is used in performing the high-frequency energy treatment, but as shown in FIG. 3B, a monopolar surgical treatment instrument for performing the high-frequency energy treatment may preferably be used. In this case, a return electrode plate 130 is attached to a patient P to be treated. This return electrode plate 130 is connected to an energy source 14 via an energization line 132. Furthermore, an electrode 52a provided on one jaw 36a and an electrode 52b provided on the other jaw 36b have an equal potential state in which first and second power supply lines 62a, 62b are electrically connected. In this case, the areas of a living tissue $L_T$ which come in contact with the first and second high-frequency electrodes 52a, 52b are small, respectively, so that a current density is high, but the current density of the return electrode plate 130 lowers. Therefore, the living tissue $L_T$ grasped between the jaws 36a and 36b is heated, whereas the living tissue $L_T$ which comes in contact with the return electrode plate 130 is heated less to a negligible degree. Therefore, the only portions of the living tissue $L_T$ that are grasped between the jaws 36a and 36b and that come in contact with the electrodes 52a, 52b are heated and denatured.

Moreover, although not shown, the high-frequency electrode may preferably be provided on the only one of the jaws 36a, 36b in a case where the monopolar surgical treatment instrument is used.

Furthermore, it is also preferable to set the output conditions of the surgical treatment instrument 12 (the set power Pset [W] of the high-frequency energy output, the set temperature Tset [° C.] of the heat energy output, the threshold values T1, T2 of the set temperature Tset of the living tissue $L_T$, etc.).

First Modification of First Embodiment

Next, a first modification will be described with reference to FIGS. 5A and 5B. This modification is the modification of the first embodiment, and the description of the same members as those described in the first embodiment or members producing the same function as that of the first embodiment is omitted. This hereinafter applies to second to fourth modifications.

In the above first embodiment, it has been described that the change of the impedance Z is measured to judge the state of the living tissue $L_T$, but a phase change (a phase difference $\Delta\theta$) may be judged to switch a treatment from a treatment using high-frequency energy to a treatment using a heat generation element or to end the treatment. In this case, the sensor 98 shown in FIG. 2 includes a voltage detecting section 142, a current detecting section 144 and a phase detecting section 146 as shown in FIG. 5A.

When a high-frequency voltage is generated from a variable voltage source 94 through a power amplifier 96, a high-frequency current having a predetermined frequency and a peak value based on the high-frequency voltage transmitted through the power amplifier 96 is output to a surgical treatment instrument 12 via the current detecting section 144. The voltage detecting section 142 detects the peak value of the high-frequency voltage transmitted through the power amplifier 96, and the detected peak value is output as output voltage value information to the phase detecting section 146. The current detecting section 144 detects the peak value of the high-frequency current generated based on the high-frequency voltage transmitted through the power amplifier 96, and outputs the detected peak value as output current value information to the phase detecting section 146.

The phase detecting section 146 detects the phase of the high-frequency voltage output through the power amplifier 96 based on the output voltage value information output from the voltage detecting section 142, and then outputs, to an output control section 92, the detected phase as output voltage phase information together with the output voltage value information. The phase detecting section 146 detects the phase of the high-frequency current transmitted through the power amplifier 96 based on the output current value information output from the current detecting section 144, and then outputs, to the output control section 92, the detected phase as output current phase information together with the output current value information.

The output control section 92 calculates the phase difference $\Delta\theta$ between the high-frequency voltage and the high-frequency current output through the power amplifier 96 based on the output voltage value information, the output voltage phase information, the output current value information and the output current phase information output from the phase detecting section 146.

The output control section 92 performs control to change the output state of the high-frequency current and the high-frequency voltage to an ON-state or OFF-state with respect to the variable voltage source 94 and power amplifier 96 based on an instruction signal output in accordance with the operation of a pedal 16a of a foot switch 16, and the calculated phase difference $\Delta\theta$.

Figure 5B:
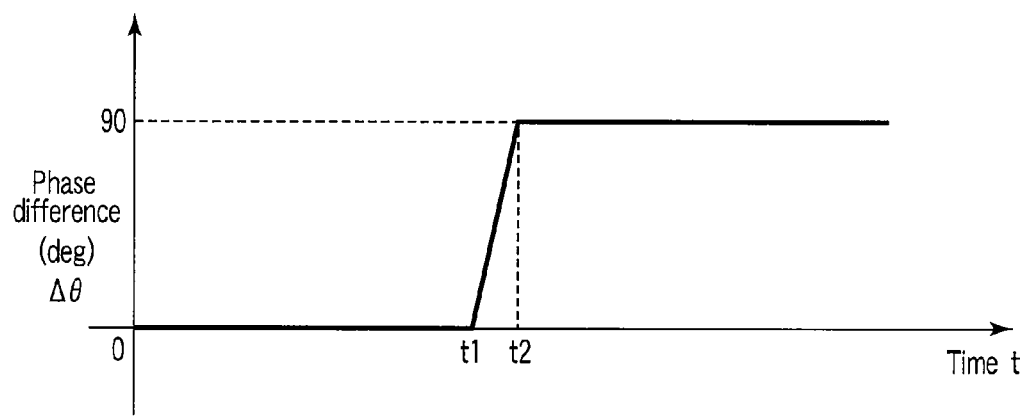
FIG. 5B is a schematic graph showing a relation between phase and time obtained from output voltage value information, output voltage phase information, output current value information and output current phase information in a case where a treatment using high-frequency energy and a treatment using heat energy are performed with respect to a living tissue by use of the treatment system according to the first modification of the first embodiment.

As shown in FIG. 5B, the phase difference $\Delta\theta$ between the high-frequency current and the high-frequency voltage output through the power amplifier 96 is 0° or substantially 0° in an initial stage in which the living tissue $L_T$ is treated. It is to be noted that the value of the phase difference $\Delta\theta$ is set to 90° or a value close to 90° in a display panel 100.

When the pedal 16a of the foot switch 16 is continuously pressed and the treatment of the living tissue $L_T$ grasped between electrodes 52a and 52b of jaws 36a and 36b proceeds, a water content is removed from the living tissue $L_T$, and the tissue $L_T$ is cauterized or coagulated. When the treatment proceeds in this manner, the phase difference $\Delta\theta$ between the high-frequency voltage and the high-frequency current output through the power amplifier 96 increases from the state of 0° or substantially 0° at, for example, appropriate time t1.

Afterward, when the pedal 16a of the foot switch 16 is further continuously pressed and the treatment of a desired portion proceeds, the value of the phase difference $\Delta\theta$ calculated by the output control section 92 has a constant value around 90° shown in FIG. 5B, for example, after time t2.

Here, it is assumed that the threshold value of the phase difference $\Delta\theta$ is set to the value close to 90° in the display panel 100. In consequence, the output control section 92 reduces the output of high-frequency energy to provide monitor output, and transmits a signal to an output control section 102 of a heat generation element driving circuit 74, whereby energy is supplied from an output section 104 to a heater member 54, thereby allowing the heater member 54 to generate heat. At this time, when predetermined time (time from the time t2 to the end of the treatment) is set in, for example, an operation display panel 108, a series of treatments end even in a state in which the pedal 16a of the foot switch 16 is continuously pressed.

It is to be noted that in this modification, the output control section 92 may not only perform the above control in a case where it is detected that the phase difference $\Delta\theta$ is the constant value around 90° but also perform the above control, for example, in a case where it is detected that the phase difference $\Delta\theta$ becomes constant at a predetermined value which is larger than 45° and which is 90° or less.

Moreover, both the change of the impedance Z and the change of the phase may be combined to switch the energy to be introduced into the living tissue $L_T$. That is, with regard to the change of the impedance Z and the change of the phase, it is also preferable that one of the impedance and the phase which reaches the threshold value earlier or later is appropriately set and used in the display panels 100, 108. Furthermore, to switch the energy to be introduced into the living tissue $L_T$, the energy may be switched from the high-frequency energy to heat energy, or the energy may be switched so that the heat energy is output together with the high-frequency energy.

It is to be noted that in the following modifications and embodiments, an example will mainly be described in which the high-frequency energy or the heat energy is switched using the changes of the threshold values Z1, Z2 of the impedance Z, but the output of the high-frequency energy or heat energy may be switched using the phase difference $\Delta\theta$. Alternatively, the changes of the impedance Z and phase difference $\Delta\theta$ may be combined to switch the output of the high-frequency energy or heat energy.

Second Modification of First Embodiment

Next, a second modification will be described with reference to FIG. 6.

An operator operates operation display panels 100, 108 in advance to set the output conditions of a surgical treatment instrument 12 (a set power Pset [W] of high-frequency energy output, a set temperature Tset [° C.] of heat energy output, threshold values Z1, Z2 of the set power Pset, etc.).

Figure 6:
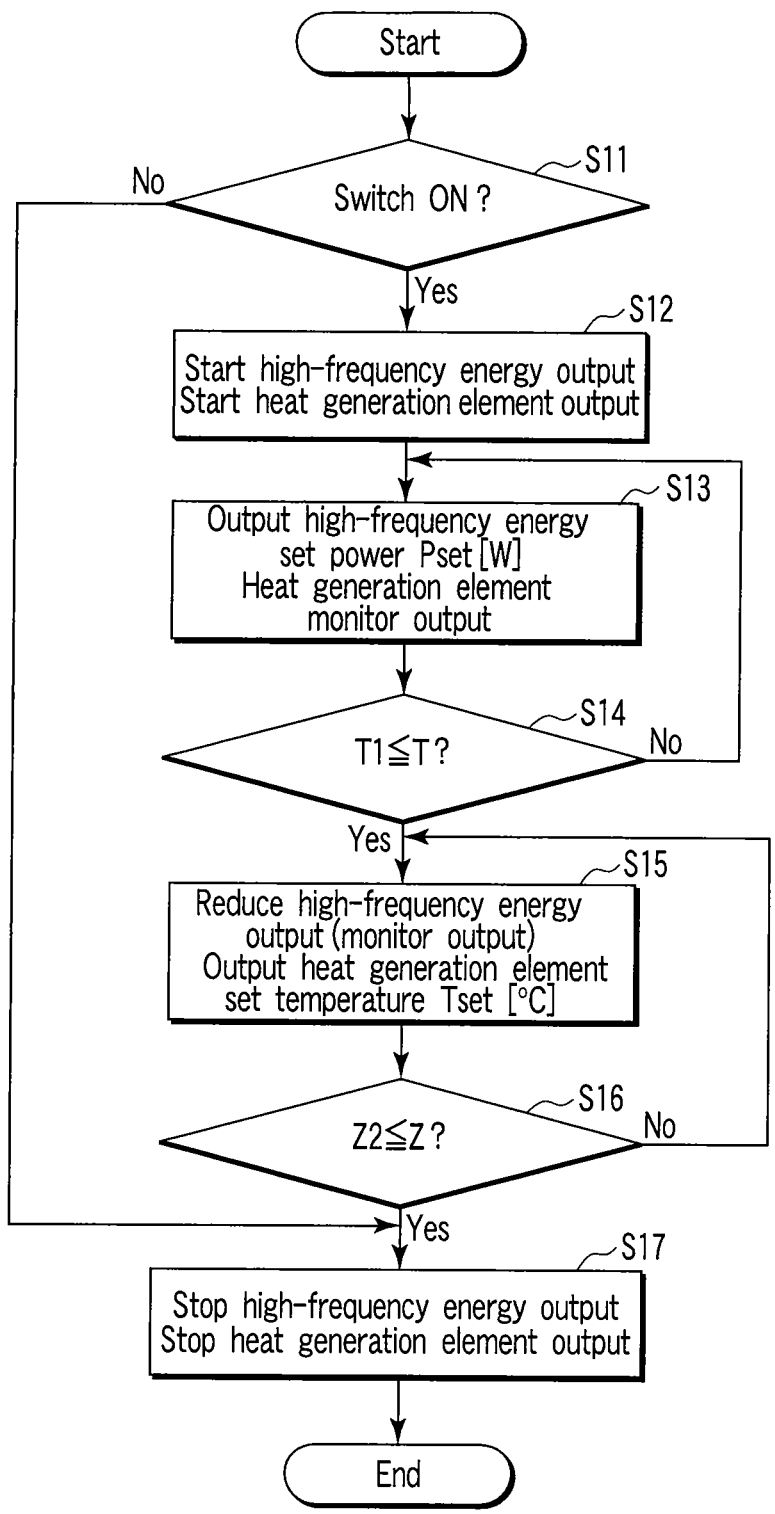
FIG. 6 is a schematic flow chart in a case where a treatment using high-frequency energy and a treatment using heat energy are performed with respect to a living tissue by use of a treatment system according to a second modification of the first embodiment.

FIG. 6 shows one example of the control flow of the surgical treatment instrument 12 controlled by a high-frequency energy driving circuit 72 and a heat generation element driving circuit 74.

First, an output control section 92 of the high-frequency energy driving circuit 72 judges whether or not a foot switch 16 has been turned on by operator's operation (STEP 11).

In a case where it is judged that the switch 16 has been turned on, high-frequency energy is output to a living tissue $L_T$ between electrodes 52a and 52b of jaws 36a and 36b of the surgical treatment instrument 12, and a heater member 54 is allowed to generate heat (STEP 12).

Then, the set power Pset [W] preset by the operation display panel 100, for example, a power of, for example, about 20 [W] to 80 [W] is supplied between the electrodes 52a and 52b of the jaws 36a and 36b, and the monitor output of the heater member 54 is started (STEP 13). The monitor output indicates that the energy is applied to such a level that the living tissue $L_T$ is not treated to allow the heater member 54 to generate the heat. A sensor 106 monitors a temperature T of the heater member 54 in accordance with such monitor output. Then, the outline of the temperature change of the living tissue $L_T$ transmitted from the living tissue $L_T$ between the jaws 36a and 36b through the electrode 52b can be monitored. That is, the heater member 54 is allowed to function as a temperature sensor, and the cauterizing of the living tissue $L_T$ grasped between the jaws 36a and 36b is started by the high-frequency energy supplied from the high-frequency energy driving circuit 72.

An output control section 102 of the heat generation element driving circuit 74 judges whether the temperature T calculated based on a signal from the sensor 106 (the temperature of the heat conducted from the living tissue $L_T$ through the electrode 52b) is a preset threshold value T1 (e.g., 100° C.) or more (STEP 14). In a case where it is judged that the temperature T is lower than the preset threshold value T1, processing is returned to STEP 13. On the other hand, in a case where it is judged that the temperature T is the preset threshold value T1 or more, the output control section 102 of the heat generation element driving circuit 74 transmits a signal to the output control section 92 of the high-frequency energy driving circuit 72 via a communication cable 82. The output control section 92 reduces the high-frequency energy output to switch the output to the monitor output. A sensor 98 can monitor the change of the impedance Z of the living tissue $L_T$ between the jaws 36a and 36b in accordance with the monitor output. Then, the output control section 102 of the heat generation element driving circuit 74 supplies the energy to the heater member 54 so that the temperature of the heater member 54 is a preset temperature Tset [° C.], for example, a temperature of 100 [° C.] to 300 [° C.] (STEP 15). Therefore, the living tissue $L_T$ grasped between the jaws 36a and 36b conducts the heat to the second electrode 52b owing to the heat conduction from the heater member 54, and the heat coagulates the living tissue $L_T$ internally from the side of the front surface of the living tissue $L_T$ which comes in close contact with the second electrode 52b.

Subsequently, the output control section 92 judges whether the impedance Z of the living tissue $L_T$ monitored in accordance with the monitor output is the preset threshold value Z2 or more (STEP 16). In a case where it is judged that the impedance Z is smaller than the threshold value Z2, the processing is returned to STEP 15. On the other hand, in a case where it is judged that the value of the impedance Z is the threshold value Z2 or more, the output control sections 92, 102 stop the output of the high-frequency energy and heat energy (STEP 17). In consequence, the treatment of the living tissue $L_T$ is completed.

Third Modification of First Embodiment

Next, a third modification will be described with reference to FIG. 7. In this modification, a heater member 54 is used as a temperature sensor.

Figure 7:
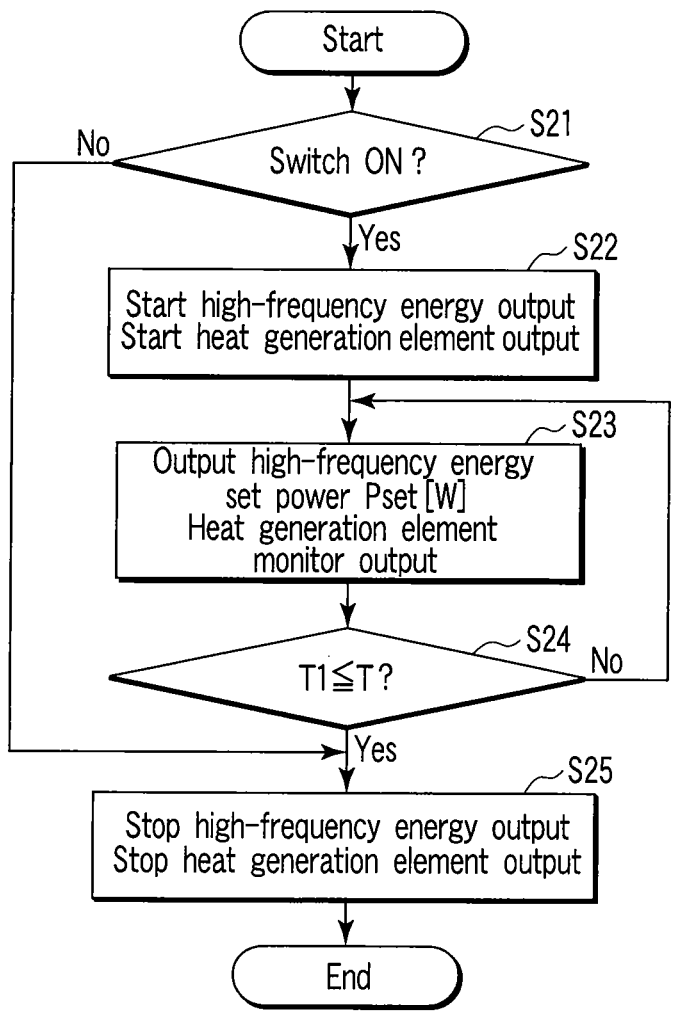
FIG. 7 is a schematic flow chart in a case where a treatment using high-frequency energy and a treatment using heat energy are performed with respect to a living tissue by use of a treatment system according to a third modification of the first embodiment.

FIG. 7 shows one example of the control flow of a surgical treatment instrument 12 controlled by a high-frequency energy output circuit 72 and a heat generation element driving circuit 74. Here, the processing of STEP 21 to STEP 24 is the same as that of the second modification shown in FIG. 6. That is, STEP 21 of FIG. 7 corresponds to STEP 11 of FIG. 6, STEP 22 corresponds to STEP 12, STEP 23 corresponds to STEP 13, and STEP 24 corresponds to STEP 14. It is judged in STEP 24 whether a temperature T of a living tissue $L_T$ is a preset threshold value T1 (e.g., T1 is about 100° C.) or more. In a case where it is judged that the temperature T is lower than the threshold value T1, processing is returned to STEP 23. In a case where it is judged that the temperature T is the threshold value T1 or more, the processing shifts to STEP 25 to complete the treatment of the living tissue $L_T$.

Fourth Modification of First Embodiment

Figure 8:
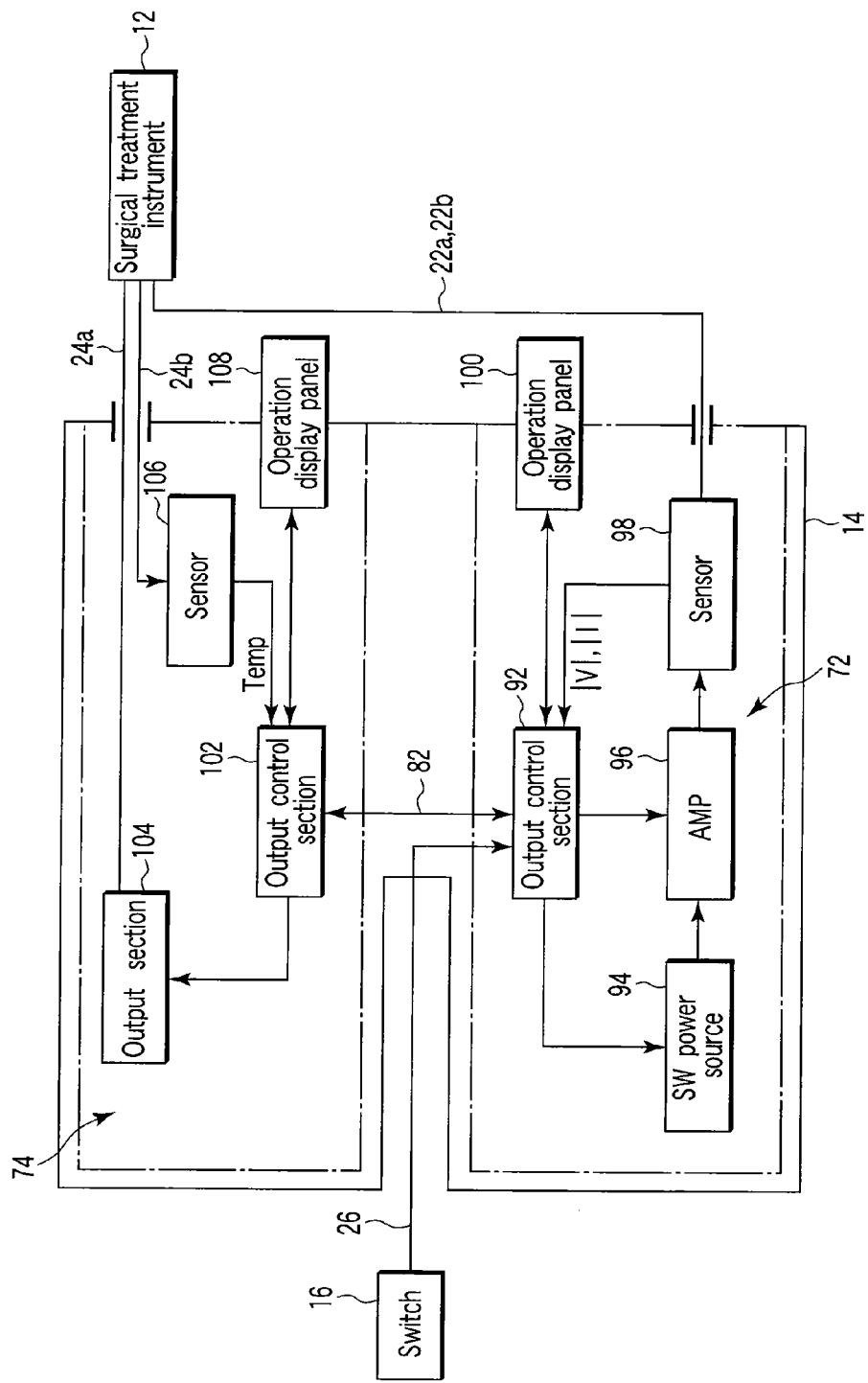
FIG. 8 is a schematic block diagram showing a treatment system according to a fourth modification of the first embodiment.

Next, a fourth modification will be described with reference to FIG. 8. This modification is an example in which unlike the heat generation element driving circuit 74 described in the first embodiment, a temperature sensor (not shown) is provided separately from a heater member 54. That is, in this modification, the heater member 54 is not used as the temperature sensor and, for example, the temperature of a living tissue $L_T$ is measured by another temperature sensor. The heater member 54 is formed of a material such as Ni—Cr or Fe—Cr. A temperature sensor such as a thermistor or a thermocouple is provided in the vicinity of the heater member 54.

The heat generation element driving circuit 74 is provided with an output section 104 which supplies a power for allowing the heater member 54 to generate heat. The output section 104 is connected to a surgical treatment instrument 12 via a connection cable 24a for heat energy output. The heat generation element driving circuit 74 is also provided with a sensor 106. The sensor 106 is connected to the temperature sensor provided separately from the heater member 54 of the surgical treatment instrument 12 via a connection cable 24b for the temperature sensor. Therefore, the sensor 106 transmits a signal indicating a temperature T of the heater member 54 to an output control section 102 based on a signal from the temperature sensor provided separately from the heater member 54. The output control section 102 sends a signal to the output section 104 based on the signal from the sensor 106. In consequence, the output control of the heater member 54 is performed.

Second Embodiment

Next, a second embodiment will be described with reference to FIGS. 9 to 15. This embodiment is the modification of the first embodiment.

Here, as the example of an energy treatment instrument (a treatment instrument), a linear surgical treatment instrument 212 for performing a treatment through, for example, an abdominal wall will be described.

As shown in FIG. 9, a treatment system 210 includes the energy treatment instrument 212, an energy source 214 and a foot switch 216.

The energy treatment instrument 212 includes a handle 222, a shaft 224 and an openable/closable holding section 226. The handle 222 is connected to the energy source 214 via a cable 228. The energy source 214 is connected to the foot switch (may be a hand switch) 216 having a pedal 216a. In consequence, the pedal 216a of the foot switch 216 is operated by an operator to turn on/off the supply of energy from the energy source 214 to the surgical treatment instrument 212.

The handle 222 is formed into such a shape that the operator easily holds the handle, and is substantially formed into an L-shape. One end of the handle 222 is provided with the shaft 224. The cable 228 extends from the proximal end of the handle 222 disposed coaxially with respect to this shaft 224.

On the other hand, the other end side of the handle 222 is a grasping section to be grasped by the operator. The handle 222 is provided with a holding section opening/closing knob 232 so that the knob 232 is arranged on the other end side of the handle. The holding section opening/closing knob 232 is connected to the proximal end of a sheath 244 (see FIGS. 10A and 10B) of the shaft 224 in the substantially middle portion of the handle 222 as described later. When the holding section opening/closing knob 232 comes close to or away from the other end of the handle 222, the sheath 244 moves along the axial direction of the sheath. The handle 222 further includes a cutter driving knob 234 for moving a cutter 254 described later in a state in which the knob 234 is arranged in parallel with the holding section opening/closing knob 232.

As shown in FIGS. 10A and 10B, the shaft 224 includes a cylindrical member 242, and the sheath 244 slidably arranged outside the cylindrical member 242. The proximal end of the cylindrical member 242 is fixed to the handle 222 (see FIG. 9). The sheath 244 is slidable along the axial direction of the cylindrical member 242.

A recessed portion 246 is formed along the axial direction of the cylindrical member 242 outside the cylindrical member 242. The recessed portion 246 is provided with a first high-frequency electrode energization line 266b connected to a first high-frequency electrode (an output section) 266 described later, and a heater member energization line 268a connected to a heater member 268. A high-frequency electrode energization line 270b connected to a second high-frequency electrode (an output section) 270 described later is inserted through the cylindrical member 242.

A driving rod 252 is arranged in the cylindrical member 242 of the shaft 224 so that the rod 252 can move along the axial direction thereof. The distal end of the driving rod 252 is provided with the thin-plate-like cutter (an auxiliary treatment instrument) 254. Therefore, when the cutter driving knob 234 is operated, the cutter 254 moves via the driving rod 252.

The distal end of the cutter 254 is provided with a blade 254a, and the distal end of the driving rod 252 is fixed to the proximal end of the cutter 254. A long groove 254b is formed between the distal end of the cutter 254 and the proximal end thereof. In this long groove 254b, a movement regulation pin 256 extending in a direction crossing the axial direction of the shaft 224 at right angles is fixed to the cylindrical member 242 of the shaft 224. Therefore, the long groove 254b of the cutter 254 moves along the movement regulation pin 256. In consequence, the cutter 254 moves straight. At this time, the cutter 254 is provided in cutter guide grooves (channels, fluid discharge grooves) 262a, 264a of a first holding member 262 and a second holding member 264 described later.

It is to be noted that engagement portions 254c which engage with the movement regulation pin 256 to control the movement of the cutter 254 are formed in at least three portions, that is, in one end and the other end of the long groove 254b of the cutter 254 and between the one end and the other end.

As shown in FIGS. 9, 10A and 10B, the holding section 226 is provided on the distal end of the shaft 224. As shown in FIGS. 10A and 10B, the holding section 226 includes the first holding member (a first jaw) 262 and the second holding member (a second jaw) 264.

The first holding member 262 and the second holding member 264 themselves preferably entirely have insulation properties, respectively. The first holding member 262 is integrally provided with a first holding member main body (hereinafter referred to mainly as the main body) 272 and a base portion 274 provided on the proximal end of the main body 272. The first holding member main body 272 and the base portion 274 are provided with the cutter guide groove 262a for guiding the cutter 254. Then, the main body 272 is provided with the first high-frequency electrode 266 and the heater member 268. That is, the first holding member 262 is provided with the first high-frequency electrode 266 and the heater member 268 as an output member and an energy release section.

As shown in FIGS. 10A to 12, the main body 272 of the first holding member 262 is provided with a recessed portion 272a and a holding face 272b including the edge of the recessed portion 272a. The first high-frequency electrode 266 is arranged in the recessed portion 272a. The front surface of the first high-frequency electrode 266 and the holding face 272b are different surfaces. The holding face 272b is arranged closer to a main body 276 of the facing second holding member 264 than the front surface of the first high-frequency electrode 266 is, and the holding face abuts on a holding face 276b of the main body 276 of the facing second holding member 264.

The first high-frequency electrode 266 is electrically connected to a first electrode connector 266a. The first electrode connector 266a is connected to the cable 228 extending from the handle 222 via the energization line 266b for the first high-frequency electrode 266. The heater member 268 is connected to the cable 228 extending from the handle 222 via the energization line 268a for the heater member 268. The main body 276 of the second holding member 264 is provided with the second high-frequency electrode 270. The second high-frequency electrode 270 is electrically connected to a second electrode connector 270a. The second electrode connector 270a is connected to the cable 228 extending from the handle 222 via the energization line 270b for the second high-frequency electrode 270.

Figure 11A:
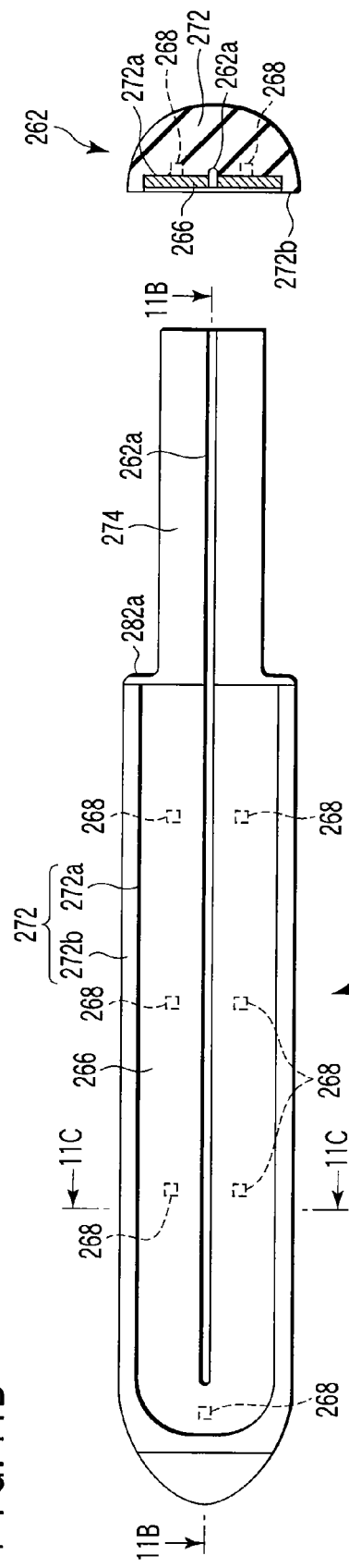
FIG. 11A is a schematic plan view showing the first holding member on a side close to the second holding member in the holding section of the energy treatment instrument of the treatment system according to the second embodiment.
Figure 11B:
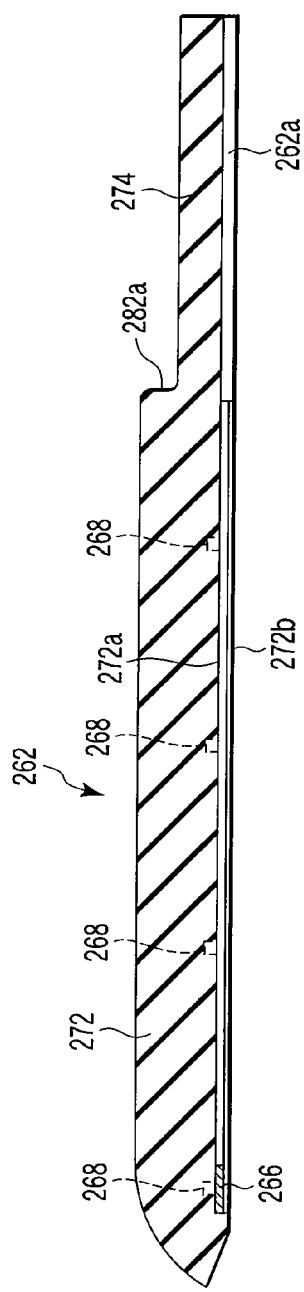
FIG. 11B is a schematic vertical sectional view showing the first holding member cut along the 11B-11B line of FIG. 11A in the holding section of the energy treatment instrument of the treatment system according to the second embodiment.
Figure 11C:
FIG. 11C is a schematic transverse sectional view showing the first holding member cut along the 11C-11C line of FIG. 11A in the holding section of the energy treatment instrument of the treatment system according to the second embodiment.
Figure 12:
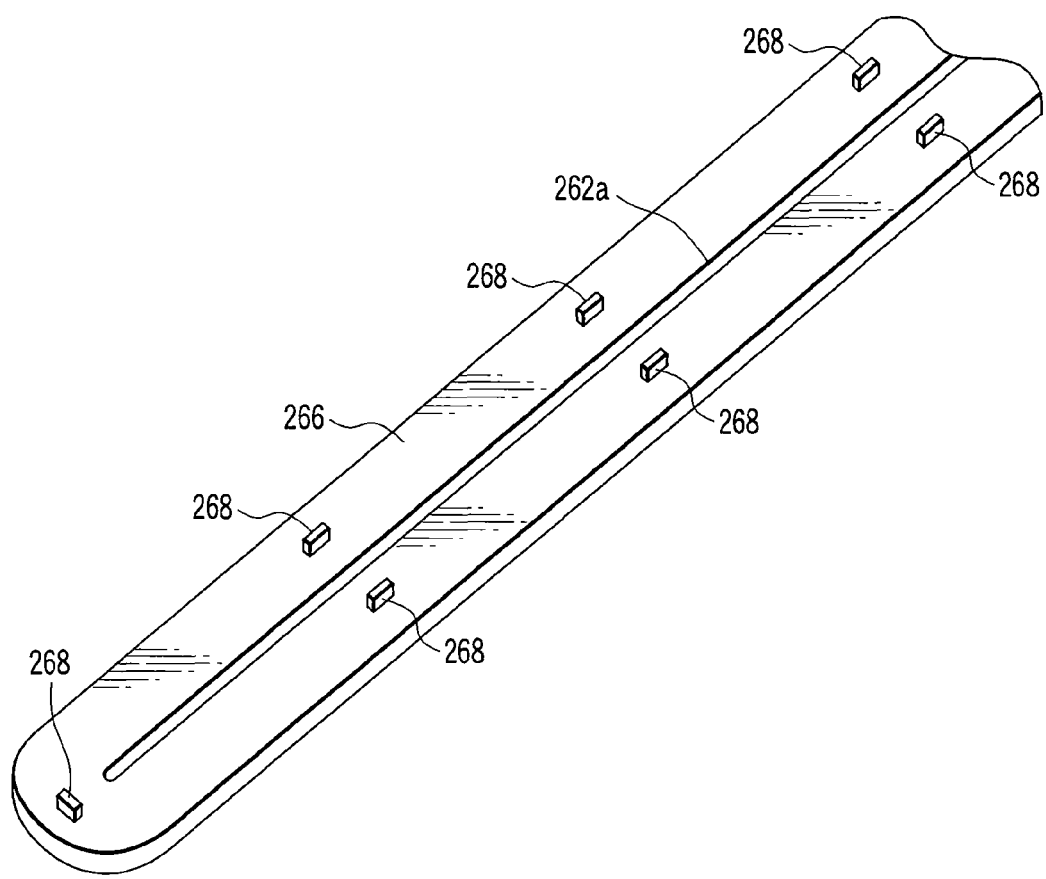
FIG. 12 is a schematic diagram showing a state in which a heater member is fixed to the back surface of a first high-frequency electrode arranged on the first holding member of the holding section of the energy treatment instrument in the treatment system according to the second embodiment.

As shown in FIGS. 11A and 12, the first high-frequency electrode 266 is continuously formed into, for example, a substantial U-shape so that the electrode 266 has two ends in the proximal end of the main body 272 of the first holding member 262. In consequence, the first high-frequency electrode 266 is provided with the cutter guide groove (conveniently denoted with symbol 262a) which guides the cutter 254 together with the first holding member 262.

The heater members 268 are provided on the back surface of the first high-frequency electrode 266 in a discrete manner. At this time, portions between the first high-frequency electrode 266 and the heater members 268 are insulated. Subsequently, when the heater member 268 generates heat, the heat is conducted to the first high-frequency electrode 266. In consequence, the living tissue $L_T$ which comes in contact with the first high-frequency electrode 266 is cauterized.

It is to be noted that the insulating main body 272 of the first holding member 262 preferably covers the outer periphery of the heater member 268, and has an insulation property. According to such a structure, when the heat generated by the heater member 268 is conducted to the first high-frequency electrode 266, the heat can be conducted in a state in which a heat loss is reduced.

The second holding member 264 integrally includes the second holding member main body 276 and a base portion 278 provided on the proximal end of the main body 276. The second holding member main body 276 and the base portion 278 are provided with the cutter guide groove 264a for guiding the cutter 254. The second main body 276 is provided with the second high-frequency electrode 270. That is, the second holding member 264 is provided with the second high-frequency electrode 270 as an output member or an energy release member.

Although not shown, the second high-frequency electrode 270 is continuously formed into, for example, a substantial U-shape (the same shape) symmetrically with the first high-frequency electrode 266 shown in FIG. 11A so that the electrode 270 has two ends in the proximal end of the main body 276 of the second holding member 264. In consequence, the second high-frequency electrode 270 is provided with the cutter guide groove (conveniently denoted with symbol 264a) which guides the cutter 254.

It is to be noted that the cutter guide grooves 262a, 264a of the first and second holding members 262, 264 are formed in a state in which the grooves 262a, 264a face each other, and the grooves 262a, 264a are formed along the axial direction of the shaft 224. Then, the two cutter guide grooves 262a, 264a can guide one cutter 254.

The cylindrical member 242 and the sheath 244 of the shaft 224 of the energy treatment instrument 212 shown in FIGS. 10A and 10B are provided with fluid discharge ports 242a, 244a via which a fluid such as vapor (a gas) or a liquid (a tissue liquid) described later is discharged. These fluid discharge ports 242a, 244a are formed in the proximal end of the shaft 224.

Here, although not shown, the outer peripheral surface of the fluid discharge port 244a of the sheath 244 is preferably provided with a connection mouthpiece. At this time, the fluid described later is discharged through the cutter guide grooves 262a, 264a, the fluid discharge port 242a of the cylindrical member 242 of the shaft 224, the fluid discharge port 244a of the sheath 244 of the shaft 224 and the connection mouthpiece. In this case, a fluid such as the vapor or the liquid discharged from the living tissue $L_T$ is sucked from the connection mouthpiece, whereby the fluid can easily be discharged from the fluid discharge ports 242a, 244a.

It is to be noted that the fluid discharge ports 242a, 244a are preferably provided in the shaft 224, but may preferably be provided in the handle 222 instead of the shaft 224.

The base portion 274 of the first holding member 262 is fixed to the distal end of the cylindrical member 242 of the shaft 224. On the other hand, the base portion 278 of the second holding member 264 is rotatably supported on the distal end of the cylindrical member 242 of the shaft 224 by a support pin 280 arranged in a direction crossing the axial direction of the shaft 224 at right angles. The second holding member 264 can rotate around the axis of the support pin 280 to open and close with respect to the first holding member 262. The second holding member 264 is urged by an elastic member 280a such as a leaf spring so that the second holding member opens with respect to the first holding member 262.

The outer surfaces of the main bodies 272, 276 of these first and second holding members 262, 264 are formed into a smoothly curved shape. Similarly, the outer surfaces of the base portions 274, 278 of these first and second holding members 262, 264 are also formed into a smoothly curved shape. In a state in which the second holding member 264 is closed with respect to the first holding member 262, the sections of the main bodies 272, 276 of the respective holding members 262, 264 are formed into a substantially circular or elliptic shape. In a state in which the second holding member 264 is closed with respect to the first holding member 262, the holding faces 272b, 276b of the main bodies 272, 276 of the first and second holding members 262, 264 face each other, and the base portions 274, 278 are formed into a cylindrical shape. In this state, the diameter of the proximal ends of the main bodies 272, 276 of the first and second holding members 262, 264 is formed to be larger than the diameter of the base portions 274, 278. Then, stepped portions 282a, 282b are formed between the main bodies 272, 276 and the base portions 274, 278, respectively.

Here, with regard to the first holding member 262 and the second holding member 264, in a state in which the second holding member 264 is closed with respect to the first holding member 262, the outer peripheral surface of the substantially circular or elliptic shape obtained by combining the base portions 274, 278 of the holding members is formed as substantially the same plane as the outer peripheral surface of the distal end of the cylindrical member 242 or formed with a diameter slightly larger than that of the outer peripheral surface. In consequence, the sheath 244 is slid with respect to the cylindrical member 242, whereby the distal end of the sheath 244 can cover the base portions 274, 278 of the first holding member 262 and the second holding member 264. In this state, as shown in FIG. 10A, the first holding member 262 and the second holding member 264 close against the urging force of the elastic member 280a. On the other hand, in a case where the sheath 244 is slid toward the proximal end of the cylindrical member 242 from a state in which the distal end of the sheath 244 covers the base portions 274, 278 of the first holding member 262 and the second holding member 264, as shown in FIG. 10B, the second holding member 264 opens with respect to the first holding member 262 owing to the urging force of the elastic member 280a.

Moreover, in this embodiment, a space between the proximal ends of the first high-frequency electrode 266 and a space between the proximal ends of the second high-frequency electrode 270 are formed to be approximately equal to the sizes of the widths of the cutter guide grooves 262a, 264a of the first holding member 262 and the second holding member 264, respectively (see FIG. 12). However, the space between the proximal ends of the first high-frequency electrode 266 and the space between the proximal ends of the second high-frequency electrode 270 may appropriately be set, respectively. That is, the first and second high-frequency electrodes 266, 270 may be provided away from the edges of the cutter guide grooves 262a, 264a of the first holding member 262 and the second holding member 264.

Figure 13:
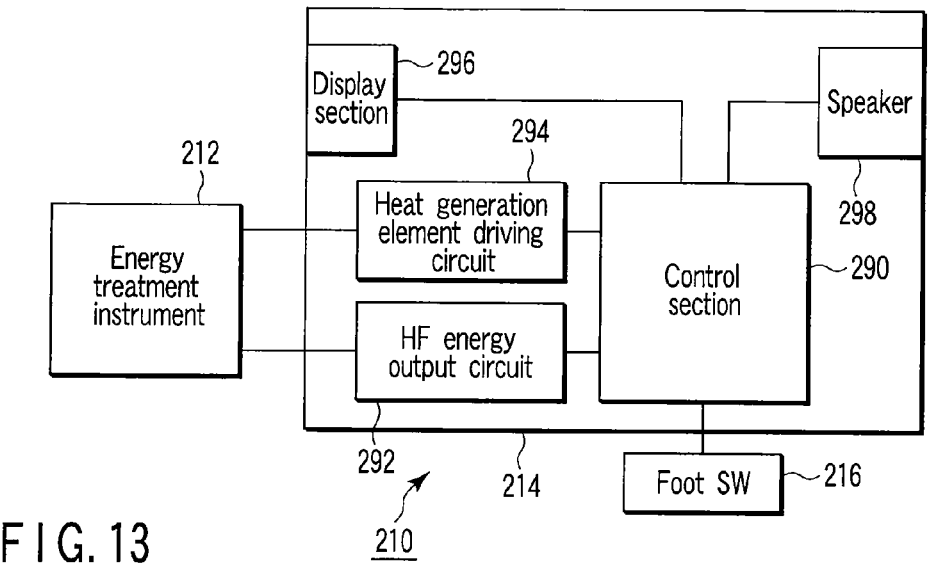
FIG. 13 is a schematic block diagram showing the treatment system according to the second embodiment.

As shown in FIG. 13, in the energy source 214, a control section 290, a high-frequency energy output circuit 292, a heat generation element driving circuit 294, a display section 296 and a speaker 298 are arranged. The control section 290 is connected to the high-frequency energy output circuit 292, the heat generation element driving circuit 294, the display section 296 and the speaker 298, and the control section 290 controls these components. Then, the high-frequency energy driving circuit 292 is connected to the heat generation element driving circuit 294 via the control section 290. The control section 290 is connected to the foot switch 216. When the foot switch 216 is turned on, the energy treatment instrument 212 performs a treatment. When the switch is turned off, the treatment stops. The display section 296 functions as setting means of the control section 290.

It is to be noted that although not shown, the high-frequency energy output circuit (a high-frequency energy output section) 292 outputs the high-frequency energy, and can detect an impedance Z as described in the first embodiment (see FIG. 2). That is, the high-frequency energy output circuit 292 has a sensor function for measuring the impedance Z of the living tissue $L_T$ between the first high-frequency electrode 266 and the second high-frequency electrode 270 of the energy treatment instrument 212.

Moreover, although not shown here (see FIG. 2), the heat generation element driving circuit 294 supplies the energy to the heater member 268 to allow the heater member 268 to generate the heat, and the circuit 294 has a sensor function for measuring a heat generation temperature T of the heater member 268.

Next, the operation of the treatment system 210 according to this embodiment will be described.

An operator operates the display section 296 of the energy source 214 in advance to set the output conditions of the treatment system 210. Specifically, a set power Pset [W] of high-frequency energy output, a set temperature Tset [° C.] of heat energy output, threshold values Z1, Z2 of the impedance Z of the living tissue $L_T$ and the like are set.

As shown in FIG. 10A, in a state in which the second holding member 264 is closed with respect to the first holding member 262, the holding section 226 and the shaft 224 of the surgical treatment instrument 212 are inserted into, for example, an abdominal cavity through an abdominal wall. The holding section 226 of the surgical treatment instrument 212 is opposed to the living tissue $L_T$ as a treatment target.

To hold the living tissue $L_T$ as the treatment target between the first holding member 262 and the second holding member 264, the holding section opening/closing knob 232 of the handle 222 is operated. At this time, with respect to the cylindrical member 242, the sheath 244 is moved to the proximal end of the shaft 224. A cylindrical portion between the base portions 274 and 278 cannot be maintained owing to the urging force of the elastic member 280a, whereby the second holding member 264 opens with respect to the first holding member 262.

The living tissue $L_T$ as the treatment target is arranged between the first high-frequency electrode 266 of the first holding member 262 and the second high-frequency electrode 270 of the second holding member 264. In this state, the grasping section opening/closing knob 232 of the handle 222 is operated. At this time, with respect to the cylindrical member 242, the sheath 244 is moved to the distal end of the shaft 224. The base portions 274, 278 are closed against the urging force of the elastic member 280a by the sheath 244 to form the cylindrical portion between the base portions. In consequence, the main body 272 of the first holding member 262 formed integrally with the base portion 274 and the main body 276 of the second holding member 264 formed integrally with the base portion 278 close. That is, the second holding member 264 closes with respect to the first holding member 262. Thus, the living tissue $L_T$ as the treatment target is grasped between the first holding member 262 and the second holding member 264.

At this time, the living tissue $L_T$ as the treatment target comes in contact with both the first high-frequency electrode 266 provided on the first holding member 262 and the second high-frequency electrode 270 provided on the second holding member 264. The peripheral tissue of the living tissue $L_T$ as the treatment target comes in close contact with both the facing contact faces of the edge of the holding face 272b of the first holding member 262 and the edge (not shown) of the holding face 276b of the second holding member 264.

Figure 14:
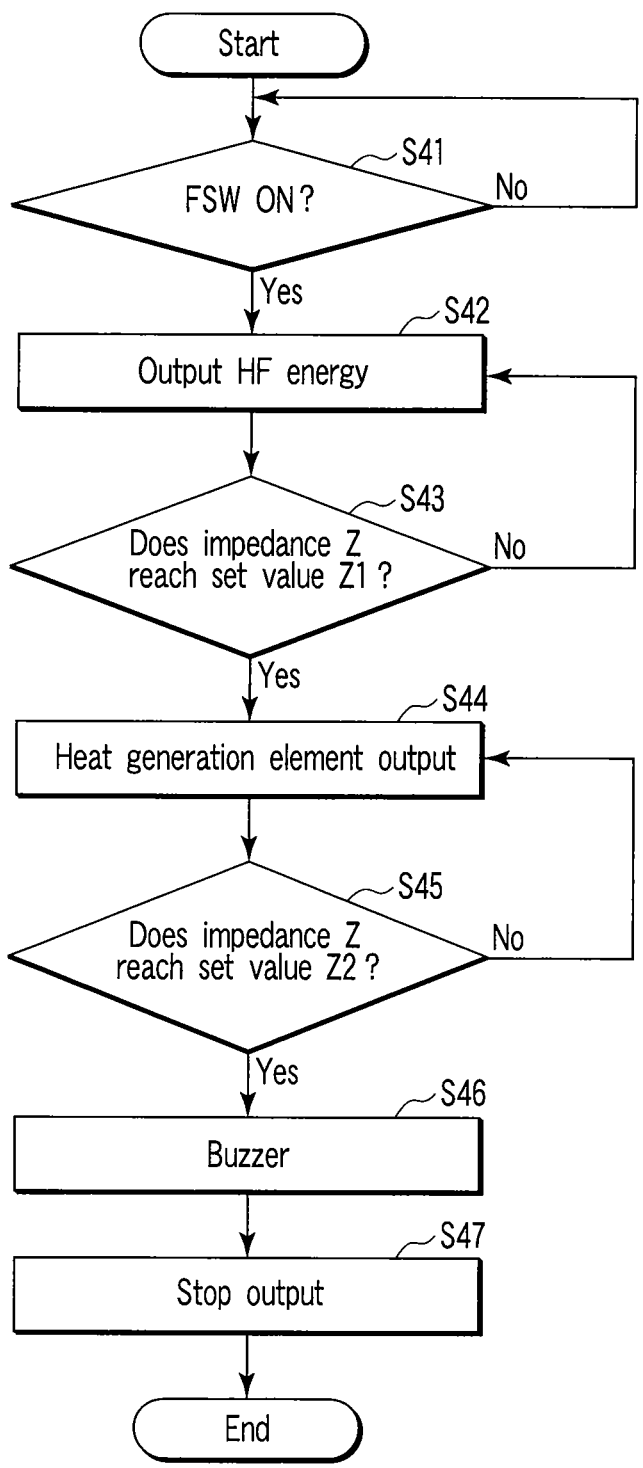
FIG. 14 is a schematic flow chart in a case where a treatment using high-frequency energy and a treatment using heat energy are performed with respect to a living tissue by use of the treatment system according to the second embodiment.

FIG. 14 shows one example of the control flow of the surgical treatment instrument 212 controlled by the high-frequency energy output circuit 292 and the heat generation element driving circuit 294.

The foot switch 216 is operated in a state in which the living tissue is grasped between the first holding member 262 and the second holding member 264. The control section 290 of the energy source 214 judges whether or not the switch 216 is turned on by operator's operation (STEP 41). When the foot switch 216 is turned on, the high-frequency energy output circuit 292 of the energy source 214 supplies the energy to the living tissue $L_T$ between the first high-frequency electrode 266 and the second high-frequency electrode 270 via the cable 228 (STEP 42). Then, the set power Pset [W] preset in the display section 296, for example, a power of about 20 [W] to 80 [W] is supplied between the electrodes 266 and 270 of the first and second holding members 262, 264.

Figure 15:
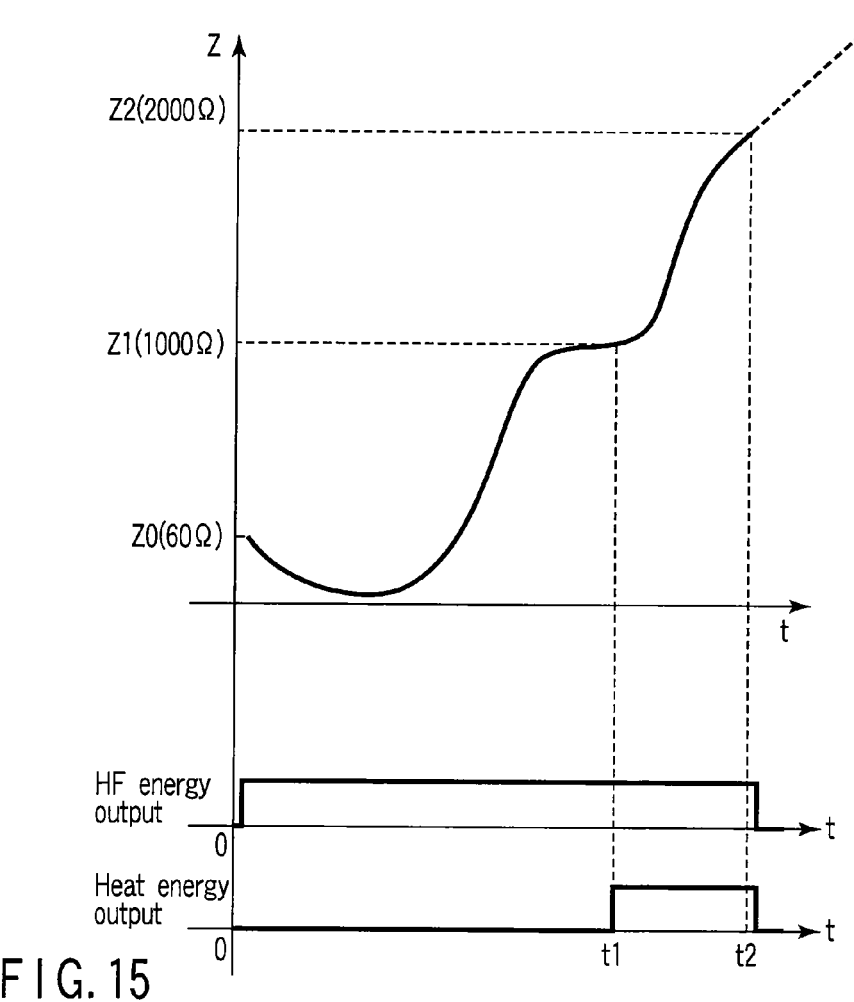
FIG. 15 is a schematic graph showing the change of the impedance of the living tissue with respect to a time when predetermined high-frequency energy is input into the living tissue, and also showing the change of the impedance of the living tissue with respect to a time when the impedance reaches a predetermined value and then predetermined heat energy is input instead of the high-frequency energy, in a case where the treatment using the high-frequency energy and the treatment using the heat energy are performed with respect to the living tissue by use of the treatment system according to the second embodiment.

In consequence, a high-frequency current flows through the living tissue $L_T$ grasped between the first holding member 262 and the second holding member 264, and the living tissue $L_T$ is allowed to generate heat to start the cauterizing of the tissue (the denaturing of the tissue). At this time, the impedance Z of the grasped living tissue $L_T$ is measured by the high-frequency energy output circuit 292. The impedance Z at a time of treatment start is, for example, about 60 [Ω] as shown in FIG. 15. Subsequently, when the high-frequency current flows through the living tissue $L_T$ to cauterize the living tissue $L_T$, the value of the impedance Z rises.

When the living tissue $L_T$ is cauterized in this manner, a fluid (e.g., a liquid (blood) and/or the gas (water vapor)) is discharged from the living tissue $L_T$. At this time, the holding faces 272b, 276b of the first and second holding members 262, 264 come in closer contact with the living tissue LT than the electrodes 266, 270. Therefore, the holding faces 272b, 276b function as a barrier portion (a dam) which inhibits the fluid from being released from the first and second holding members 262, 264. Therefore, the fluid discharged from the living tissue $L_T$ is allowed to flow into the cutter guide grooves 262a, 264a disposed internally from the electrodes 266, 270, and the fluid is sucked to flow from the first and second holding members 262, 264 to the shaft 224. While the fluid is discharged from the living tissue $L_T$, the fluid is allowed to continuously flow into the cutter guide grooves 262a, 264a. In consequence, it is prevented that thermal spread is caused by the fluid discharged from the living tissue $L_T$ in a state in which the temperature rises, and it can be prevented that a portion which is not the treatment target is influenced.

Subsequently, the control section 290 judges whether the impedance Z during the high-frequency energy output calculated based on the signal from the high-frequency energy output circuit 292 is the preset threshold value Z1 (here, about 1000 [Ω] as shown in FIG. 15) or more (STEP 43). The threshold value Z1 is in such a position that the rise ratio of the value of the impedance Z known in advance becomes dull. Then, in a case where it is judged that the impedance Z is smaller than the threshold value Z1, processing is returned to STEP 42. That is, the high-frequency energy for the treatment is continuously applied to the living tissue $L_T$ grasped between the electrodes 266 and 270 of the first and second holding members 262, 264.

In a case where it is judged that the impedance Z becomes larger than the threshold value Z1, the control section 290 transmits a signal to the heat generation element driving circuit 294. Then, the heat generation element driving circuit 294 supplies a power to the heater member 268 so that the temperature of the heater member 268 is a preset temperature Tset [° C.], for example, a temperature of 100 [° C.] to 300 [° C.] (STEP 44). In consequence, the living tissue $L_T$ grasped between the electrodes 266 and 270 of the first and second holding members 262, 264 conducts the heat to the first electrode 266 owing to the heat conducted from the heater member 268, and the heat coagulates the living tissue $L_T$ internally from the side of the front surface of the living tissue $L_T$ which comes in close contact with the first electrode 266.

Subsequently, the control section 290 judges whether the impedance Z of the living tissue $L_T$ monitored by the high-frequency energy output circuit 292 is a preset threshold value Z2 (here, about 2000 [Ω] as shown in FIG. 15) or more (STEP 45). In a case where it is judged that the impedance Z is smaller than the threshold value Z2, the processing is returned to STEP 44. On the other hand, in a case where it is judged that the impedance Z is the threshold value Z2 or more, the control section 290 issues a buzzer sound from the speaker 298 (STEP 46), and stops the output of high-frequency energy and heat energy (STEP 47). In consequence, the treatment of the living tissue $L_T$ by use of the treatment system 210 is completed.

As described above, according to this embodiment, the following effect is obtained. The description of the effect described in the first embodiment is omitted.

The fluid (a water content, vapor) generated at a time when the high-frequency energy is applied to the living tissue $L_T$ to destroy the cell membrane of the living tissue $L_T$ and/or a time when the heat energy is applied to cauterize the living tissue $L_T$ can be guided to the cutter guide grooves 262a, 264a. The fluid is guided to these cutter guide grooves 262a, 264a, whereby the fluid generated from the living tissue $L_T$ can be discharged from the shaft 224 or the handle 222 through the energy treatment instrument 212. In consequence, it can be prevented that the heat is applied to a living tissue $L_T$ which is not related to the treatment owing to the fluid generated from the treated living tissue $L_T$. That is, the fluid can be guided from the living tissue $L_T$ to these cutter guide grooves 262a, 264a to prevent the thermal spread from being caused.

It is to be noted that in the second embodiment, the structure has been described in which to prevent the thermal spread, the holding faces 272b, 276b disposed externally from the first high-frequency electrode 266 are used as the barrier portion. In addition, a structure is preferable in which the holding faces 272b, 276b of the second embodiment are provided with, for example, a cooling plate for cooling via a cooling medium or the like, whereby the living tissue $L_T$ and a fluid such as the vapor can indirectly be cooled.

Moreover, in this embodiment, the linear energy treatment instrument 212 (see FIG. 9) for treating the living tissue $L_T$ in the abdominal cavity (in the body) through the abdominal wall has been described as the example, but as shown in, for example, FIG. 16, an open type linear energy treatment instrument (a treatment instrument) 212a for taking a treatment target tissue from the body through the abdominal wall to treat the tissue may be used.

The energy treatment instrument 212a includes a handle 222 and a holding section 226. That is, unlike the energy treatment instrument 212 (see FIG. 9) for treating the tissue through the abdominal wall, a shaft 224 is omitted. On the other hand, a member having a function similar to that of the shaft 224 is arranged in the handle 222. In consequence, the energy treatment instrument 212a shown in FIG. 16 can be used in the same manner as in the energy treatment instrument 212 described above with reference to FIG. 9.

First Modification of Second Embodiment

Next, a first modification will be described with reference to FIGS. 17A and 17E. This modification is the modification of the second embodiment, and the description of the same members as those described in the second embodiment or members producing the same function as that of the second embodiment is omitted. This hereinafter applies to second to fifth modifications.

In this modification, the output configuration of energy generated from a high-frequency energy output circuit 292 and a heat generation element driving circuit 294 will be described.

Figure 17A:
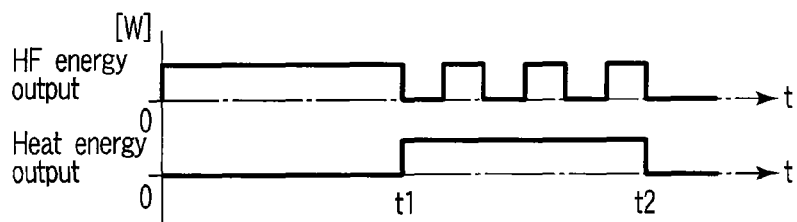
FIG. 17A is a schematic graph showing one example of an input process of high-frequency energy into a living tissue with respect to time and an input process of heat energy into the living tissue with respect to time, in a case where a treatment using the high-frequency energy and a treatment using the heat energy are performed with respect to the living tissue by use of a treatment system according to a first modification of the second embodiment.

In the example shown in FIG. 17A, unlike the example of the second embodiment shown in FIG. 15, the high-frequency energy output circuit 292 outputs energy, and an impedance Z of a living tissue $L_T$ reaches a threshold value Z1. Afterward, the high-frequency energy is output every predetermined time to measure the impedance Z of the living tissue $L_T$ every time.

On the other hand, when the impedance Z reaches the threshold value Z1, the heat generation element driving circuit 294 simultaneously outputs energy to a heater member 268, and heat (heat energy) is conducted from the heater member 268 to the living tissue $L_T$ via an electrode 266 to treat the tissue $L_T$.

Subsequently, when the impedance Z reaches a threshold value Z2, the output from the high-frequency energy output circuit 292 and heat generation element driving circuit 294 is automatically stopped to automatically end the treatment.

Figure 17B:
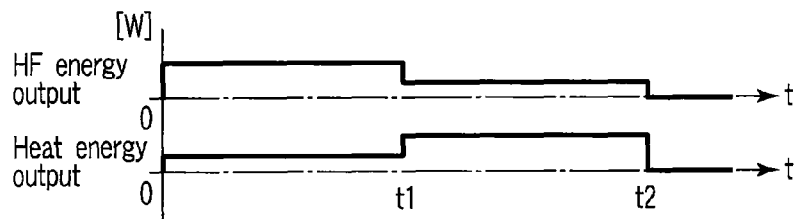
FIG. 17B is a schematic graph showing one example of the input process of the high-frequency energy into the living tissue with respect to the time and the input process of the heat energy into the living tissue with respect to the time, in a case where the treatment using the high-frequency energy and the treatment using the heat energy are performed with respect to the living tissue by use of the treatment system according to the first modification of the second embodiment.

In the example shown in FIG. 17B, the high-frequency energy output circuit 292 outputs the energy, and the impedance Z of the living tissue $L_T$ reaches the threshold value Z1. Afterward, the high-frequency energy is output as monitor output to continuously measure the change of the impedance Z.

On the other hand, the high-frequency energy output circuit 292 outputs the energy to the heater member 268, and the heat generation element driving circuit 294 simultaneously outputs the energy to the heater member 268. The output at this time is monitor output for a purpose of measuring the temperature of the living tissue $L_T$. Subsequently, when the impedance Z reaches the threshold value Z1, the heat generation element driving circuit 294 simultaneously outputs the energy for the treatment to the heater member 268, and the heater member 268 is allowed to generate the heat. Then, the heat energy is conducted from the heater member 268 to the living tissue $L_T$ through the electrode 266 to treat the tissue $L_T$. At this time, the temperature of the living tissue $L_T$ can also be measured.

Subsequently, when the impedance Z reaches the threshold value Z2, the output from the high-frequency energy output circuit 292 and heat generation element driving circuit 294 is automatically stopped to automatically end the treatment.

Figure 17C:
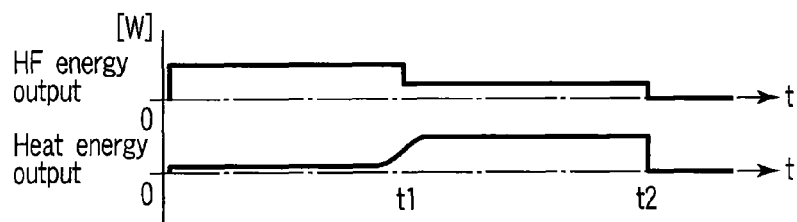
FIG. 17C is a schematic graph showing one example of the input process of the high-frequency energy into the living tissue with respect to the time and the input process of the heat energy into the living tissue with respect to the time, in a case where the treatment using the high-frequency energy and the treatment using the heat energy are performed with respect to the living tissue by use of the treatment system according to the first modification of the second embodiment.

In the example shown in FIG. 17C, the high-frequency energy output circuit 292 outputs the energy, and the impedance Z of the living tissue $L_T$ reaches the threshold value Z1. Afterward, the high-frequency energy is output as the monitor output to continuously measure the change of the impedance Z.

On the other hand, it is predicted that the impedance Z reaches the threshold value Z1. Immediately before the impedance reaches the threshold value Z1, the energy is output from the heat generation element driving circuit 294 to the heater member 268, and the heat is conducted from the heater member 268 to the living tissue $L_T$ via the electrode 266 to treat the tissue $L_T$. At this time, the amount of the energy to be supplied to the heater member 268 is gradually increased, and held in a constant state.

Subsequently, when the impedance Z reaches the threshold value Z2, the output from the high-frequency energy output circuit 292 and heat generation element driving circuit 294 is automatically stopped, and the treatment is automatically ended.

Figure 17D:
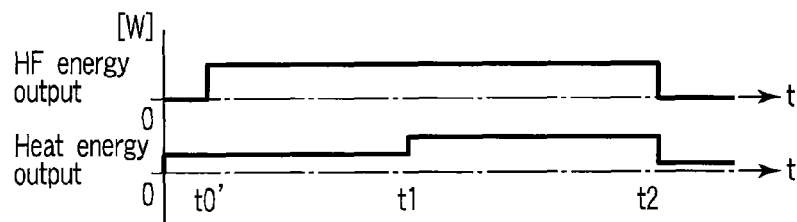
FIG. 17D is a schematic graph showing one example of the input process of the high-frequency energy into the living tissue with respect to the time and the input process of the heat energy into the living tissue with respect to the time, in a case where the treatment using the high-frequency energy and the treatment using the heat energy are performed with respect to the living tissue by use of the treatment system according to the first modification of the second embodiment.

The example shown in FIG. 17D is an example in which before the energy is output from the high-frequency energy output circuit 292, the energy is output from the heat generation element driving circuit 294 to the heater member 268 to keep the living tissue $L_T$ as the treatment target at such a temperature (T0) that protein denaturation is not caused. The temperature of the living tissue $L_T$ as the treatment target is preliminarily kept in this manner, whereby the impedance Z can be lowered and stabilized. Afterward, the above-mentioned appropriate treatment is performed, so that the treatment of the living tissue $L_T$ can be stabilized.

Figure 17E:
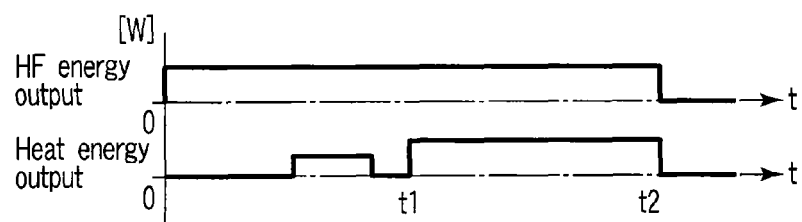
FIG. 17E is a schematic graph showing one example of the input process of the high-frequency energy into the living tissue with respect to the time and the input process of the heat energy into the living tissue with respect to the time, in a case where the treatment using the high-frequency energy and the treatment using the heat energy are performed with respect to the living tissue by use of the treatment system according to the first modification of the second embodiment.

The example shown in FIG. 17E is an example in which the energy is discontinuously output from the heat generation element driving circuit 294 to the heater member 268. The energy is once preliminarily applied to the heater member 268 to output the energy from the member, before the impedance Z reaches the threshold value Z1. Afterward, when the impedance Z reaches the threshold value Z1 and then the heat generation element driving circuit 294 applies the energy to the heater member 268, the temperature of the heater member 268 can immediately be raised to a desired temperature.

Second Modification of Second Embodiment

Next, a second modification will be described with reference to FIG. 18. In this modification, another preferable configuration of a heater member 268 provided on a first holding member 262 will be described.

Figure 18:
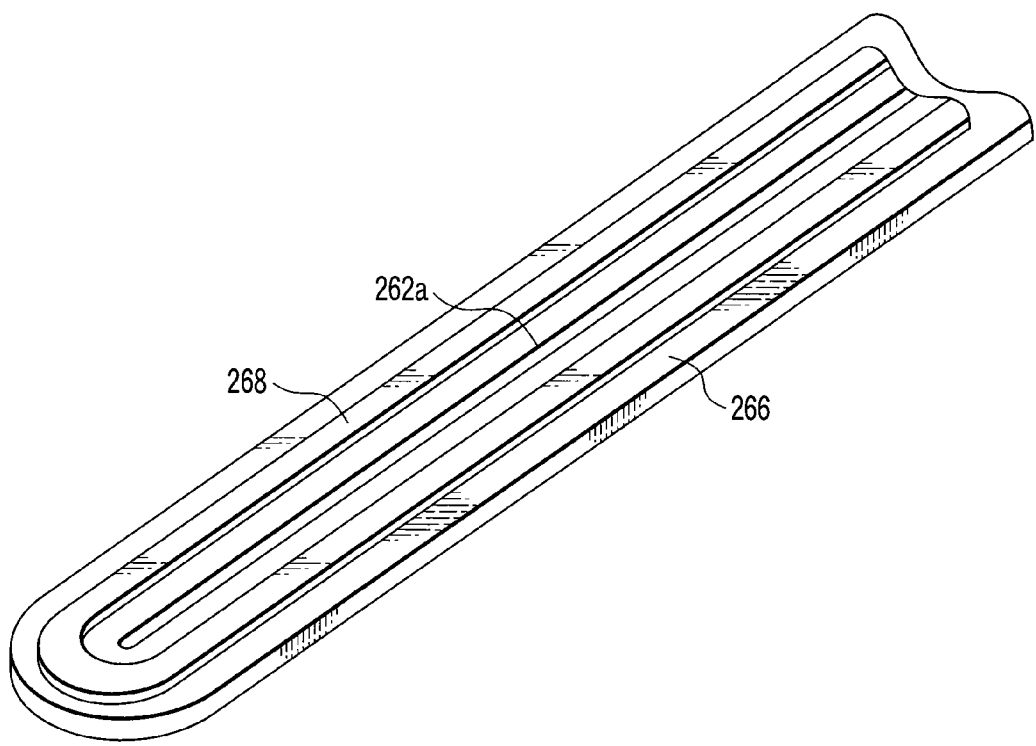
FIG. 18 is a schematic diagram showing a state in which a heater member is fixed to the back surface of a first high-frequency electrode provided on a first holding member of a holding section of an energy treatment instrument in a treatment system according to a second modification of the second embodiment.

As shown in FIG. 18, the back surface of a first high-frequency electrode 266 arranged on a main body 272 of the first holding member 262 is provided with a heat generation resistor of a screen printed thick film, a heat generation resistor of a thin film formed by a physical vapor deposition (PVD) process or a nichrome line. In consequence, for example, a U-shaped heater member 268 which does not have any cut is fixed to the back surface of the U-shaped first high-frequency electrode 266.

In consequence, when energy is applied to the heater member 268 and heat is generated from the heater member 268, the heat is conducted from the heater member 268 to the first high-frequency electrode 266.

The heater member 268 described in this modification is not limited to the heat generation resistor of the thick or thin film or the nichrome line, and various heating elements may be used.

Third Modification of Second Embodiment

Next, a third modification will be described with reference to FIGS. 19A to 20C. In this modification, the configuration of a first holding member 262 will be described. In this modification, the configuration of a first high-frequency electrode 266 arranged on a main body 272 of the first holding member 262 will mainly be described, and a treatment using a cutter 254 will also be described.

As shown in FIGS. 19A to 19C, the main body 272 of the first holding member 262 is provided with the first high-frequency electrode 266. As shown in FIG. 19A, the first high-frequency electrode 266 includes a continuous electrode (a sealing member, a first bonding member) 302 formed continuously without any cut, and a plurality of discrete electrodes (maintaining members, second bonding members) 304 arranged outside this continuous electrode 302 in a discrete manner.

The continuous electrode 302 is continuously formed into, for example, a substantial U-shape so that the continuous electrode 302 has two ends in the proximal end of the main body 272 of the first holding member 262. A space between the proximal ends of the continuous electrode 302 is approximately the width of a cutter guide groove 262a (see FIGS. 19A and 19C), but the space between the proximal ends of the continuous electrode 302 can appropriately be set. That is, the continuous electrode 302 may be provided away from the edge of the cutter guide groove 262a of the first holding member 262.

A plurality of discrete electrodes 304 having the same shape are arranged at substantially equal intervals along a substantially U-shaped virtual track. The discrete electrodes 304 are formed into, for example, a circular shape. The discrete electrodes 304 are arranged so that a substantially predetermined space is made between the electrodes 304, and the respective discrete electrodes 304 are arranged as much as an appropriate distance away from the continuous electrode 302. The discrete electrodes 304 are positioned so that when a treatment is performed, the living tissue $L_T$ between the discrete electrode 304 and a discrete electrode (not shown) of the second holding member 264 is allowed to denature owing to the heat, but the denaturation of the living tissue $L_T$ between the discrete electrodes 304 of the first holding member 262 due to the heat and the denaturation of the living tissue between the discrete electrodes 304 and the continuous electrode 302 due to the heat are prevented as much as possible.

It is to be noted that the heater members 268 are preferably fixed to both of the continuous electrode 302 and the discrete electrodes 304 of the first holding member 262. Therefore, the non-uniformity of the heat conduction from the heater members 268 to the continuous electrode 302 and the discrete electrodes 304 can be prevented as much as possible, and the heat can be applied to the living tissue $L_T$ as uniformly as possible.

The main body 272 and the base portion 274 of the first holding member 262 are provided with the cutter guide groove 262a for guiding the cutter 254 therethrough. A main body 276 and a base portion 278 of the second holding member 264 are provided with a cutter guide groove 264a for guiding the cutter 254 therethrough. These cutter guide grooves 262a, 264a are formed along the axial direction of a shaft 224. Therefore, the cutter 254 can move along the cutter guide grooves 262a, 264a in the first holding member 262 and the second holding member 264.

As described in the second embodiment and the second modification of the second embodiment, the heater member 268 is arranged discretely and/or continuously on the back surface of the continuous electrode 302 and/or the discrete electrode 304.

Moreover, the second holding member 264 is also provided with the second high-frequency electrode 270 symmetrically with the first holding member 262. The detailed description of this respect is omitted.

It is to be noted that although not shown, the continuous electrode of the second high-frequency electrode 270 is conveniently denoted with reference numeral 306, and the discrete electrodes are denoted with reference numeral 308 in the following description of a function.

Next, the function of the treatment system 210 according to this modification will be described.

As shown in FIG. 10A, in a state in which the second holding member 264 is closed with respect to the first holding member 262, for example, the holding section 226 and the shaft 224 of the energy treatment instrument 212 are inserted into, for example, an abdominal cavity through an abdominal wall. Then, the living tissue $L_T$ as the treatment target is held between the first holding member 262 and the second holding member 264.

At this time, the living tissue $L_T$ as the treatment target comes in contact with both of the first high-frequency electrode 266 provided on the first holding member 262 and the second high-frequency electrode 270 provided on the second holding member 264. The peripheral tissue of the living tissue $L_T$ as the treatment target comes in close contact with both of the holding face 272b of the main body 272 of the first holding member 262 and the holding face 276b of the main body 276 of the second holding member 264.

When the pedal 216a of the foot switch 216 is operated in this state, energy is supplied to the first high-frequency electrode 266 and the second high-frequency electrode 270.

The first high-frequency electrode 266 supplies a high-frequency current between the electrode and the second high-frequency electrode 270 via the living tissue $L_T$ as the treatment target. In consequence, the living tissue $L_T$ between the first high-frequency electrode 266 and the second high-frequency electrode 270 is heated. In this case, the living tissue $L_T$ is continuously (a substantially U-shaped state) denatured by the continuous electrodes 302, 306 of the first and second high-frequency electrodes 266, 270. Furthermore, the living tissue $L_T$ between these discrete electrodes 304 and 308 is discretely denatured by the discrete electrodes 304, 308 of the first and second high-frequency electrodes 266, 270.

When the pressed pedal 216a of the foot switch 216 is maintained and the impedance Z reaches the threshold value Z1, the amount of the high-frequency energy to be supplied is reduced to switch to the monitor output, and the energy is supplied to the heater member 268 to allow the heater member 268 to generate the heat. Therefore, the heat energy of the heater member 268 is conducted from the heater member to the continuous electrode 302 and the discrete electrodes 304. Then, the living tissue $L_T$ receives the heat from the front surfaces of the continuous electrode 302 and the discrete electrodes 304, and is cauterized. Subsequently, when the impedance Z reaches the threshold value Z2, the supply of the high-frequency energy and heat energy is stopped. That is, when the pedal 216a of the foot switch 216 is continuously pressed and the impedance Z reaches the threshold value Z2, the treatment automatically ends.

Figure 20A:
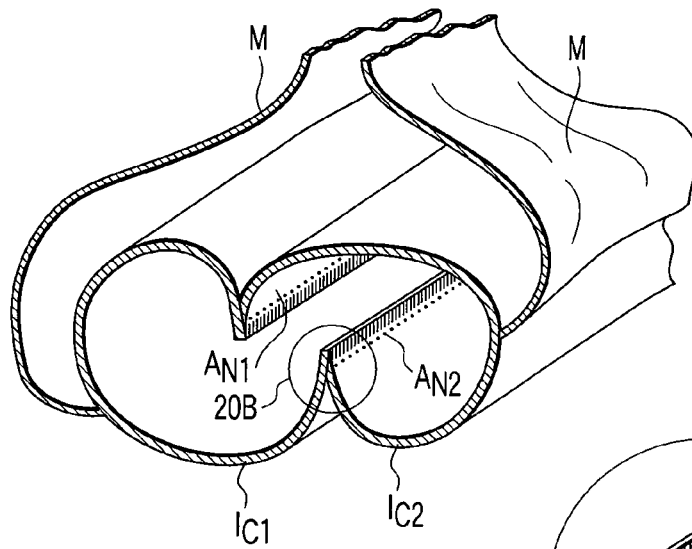
FIG. 20A is a schematic perspective view showing a state in which two intestinal canals of a small intestine are anastomosed, and a schematic diagram cut along the 20A-20A line of FIG. 20C described later.
Figure 20B:
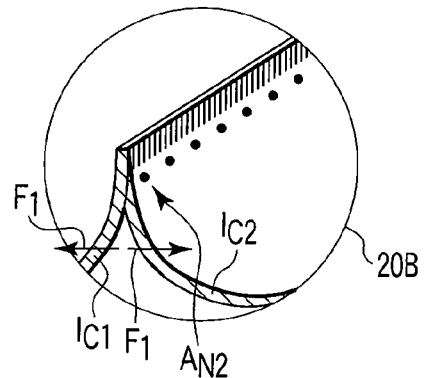
FIG. 20B is a schematic diagram showing an enlarged part denoted with symbol 20B of FIG. 20A.
Figure 20C:
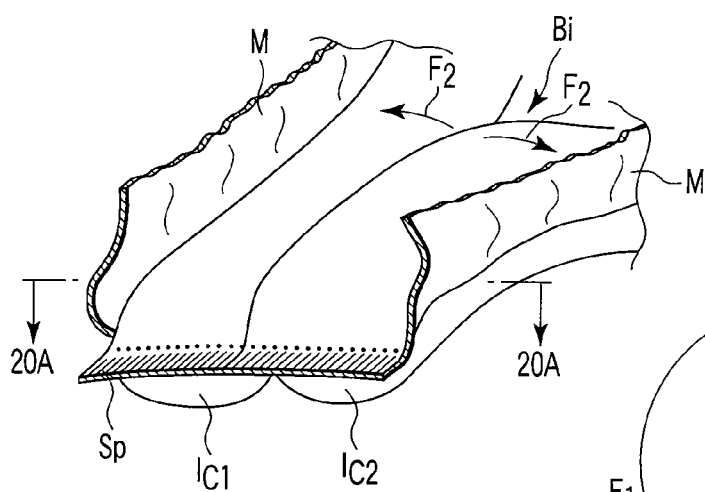
FIG. 20C is a schematic diagram showing a state in which two intestinal canals of the small intestine are anastomosed, and then the ends of the intestinal canals are closed.

Here, there will be described a case where, for example, intestinal canals $I_{C1}$, $I_{C2}$ of a small intestine are anastomosed with each other by use of the treatment system 210 having such a function as shown in FIGS. 20A to 20C.

The holding faces 272b, 276b of the first and second holding members 262, 264 hold a pair of arranged intestinal canals $I_{C1}$, $I_{C2}$ between the wall surfaces of both the intestinal canals $I_{C1}$, $I_{C2}$. When the pedal 216a of the foot switch 216 is pressed in this state, the energy is supplied to the first and second high-frequency electrodes 266, 270, respectively. Then, the intestinal canals $I_{C1}$, $I_{C2}$ held between the continuous electrode 302 of the first holding member 262 and the continuous electrode 306 of the second holding member 264 are heated and denatured. In consequence, the wall surfaces of the intestinal canals $I_{C1}$, $I_{C2}$ are continuously denatured.

Moreover, simultaneously with the denaturation of the living tissue by the continuous electrodes 302, 306, the intestinal canals $I_{C1}$, $I_{C2}$ between the discrete electrodes 304 of the first holding member 262 and the discrete electrodes 308 of the second holding member 264 are denatured. In consequence, the wall surfaces of the intestinal canals $I_{C1}$, $I_{C2}$ are discretely denatured.

Afterward, when the impedance Z reaches the threshold value Z1, the amount of the high-frequency energy to be supplied is reduced to switch to the monitor output, and the energy is supplied to the heater member 268 to generate the heat from the heater member 268. In consequence, the heat is conducted from the heater member 268 to the continuous electrode 302 and the discrete electrodes 304 owing to the heat energy generated from the heater member 268, and the heat is conducted to the intestinal canals $I_{C1}$, $I_{C2}$ to bond the wall surfaces to each other. Subsequently, when the impedance Z reaches the threshold value Z2, the supply of the energy automatically stops, thereby ending the treatment.

Thus, the living tissues of the intestinal canals $I_{C1}$, $I_{C2}$ are discretely denatured and bonded to each other.

Then, the supply of the energy to the first and second high-frequency electrodes 266, 270 and the heater member 268 is stopped. Afterward, while the intestinal canals $I_{C1}$, $I_{C2}$ are grasped, the cutter driving knob 234 shown in FIG. 9 is operated to move forwards the cutter 254 along the cutter guide grooves 262a, 264a from the state shown in FIGS. 10A and 10B. When the cutter 254 moves forwards, a portion denatured and bonded by the continuous electrodes 302, 306 is cut. Then, the cutter 254 cuts the inner portion of the substantially U-shaped denatured portion is cut to the vicinity of the distal end of the portion with the continuous electrodes 302, 306. Therefore, a portion between the substantially U-shaped sealed portions of the wall surfaces of the intestinal canals $I_{C1}$, $I_{C2}$ is cut to connect the wall surfaces of the intestinal canals $I_{C1}$, $I_{C2}$ to each other. That is, the wall surfaces of the intestinal canals $I_{C1}$, $I_{C2}$ are anastomosed with each other.

The holding section opening/closing knob 232 of the handle 222 is operated in this state to open the first and second holding members 262, 264. At this time, a first anastomosed portion $A_{N1}$ on a mesenterium M side and a second anastomosed portion $A_{N2}$ on a side opposite to a side provided with the mesenterium M are formed. As shown in, for example, FIG. 20B, the continuously bonded outer portion of the second anastomosed portion $A_{N2}$ is discretely denatured.

Furthermore, in a state in which the first and second holding members 262, 264 are closed to hold the ends of the intestinal canals $I_{C1}$, $I_{C2}$, the pedal 16a of the foot switch 16 is pressed to apply the high-frequency energy and the heat energy. In consequence, as shown in FIG. 20C, the ends of the intestinal canals $I_{C1}$, $I_{C2}$ are denatured and sealed by the high-frequency electrodes 266, 270 and the heater member 268. That is, the ends of the intestinal canals $I_{C1}$, $I_{C2}$ are provided with a seal portion $S_P$. At this time, the section cut along the 20A-20A line of FIG. 20C schematically has the state shown in FIG. 20A. In consequence, the intestinal canals $I_{C1}$, $I_{C2}$ having the ends thereof sealed with the seal portion $S_P$ are anastomosed with each other.

It is to be noted that the extra portion of the seal portion $S_P$ is cut with, for example, the cutter 254. At this time, the continuously bonded peripheral portion of the sealed end (the seal portion $S_P$) of the intestinal canals $I_{C1}$, $I_{C2}$ is discretely denatured in the same manner as in FIG. 20B. That is, the living tissue between the portions of the intestinal canals $I_{C1}$, $I_{C2}$ denatured and bonded by the discrete electrodes 304, 308 is not denatured. Therefore, the periphery (the vicinity) of the portion of the living tissue bonded by the discrete electrodes 304, 308 comes in contact with (comes in close contact with) the living tissue of the intestinal canals $I_{C1}$, $I_{C2}$ which are not denatured.

Therefore, at the first anastomosed portion $A_{N1}$ on the mesenterium M side, a force is exerted in a direction in which the intestinal canals $I_{C1}$, $I_{C2}$ come in close contact with each other. Then, the portion where the living tissue has been denatured by the discrete electrodes 304, 308 exerts such a force that the living tissues more firmly come in close contact with each other. Furthermore, at the second anastomosed portion $A_{N2}$ on the side opposite to the side provided with the mesenterium M, a force $F_1$ is exerted in a direction in which the intestinal canals $I_{C1}$, $I_{C2}$ open, but the portion in which the living tissue has been denatured by the discrete electrodes 304, 308 exerts such a force that the living tissues come in close contact with each other. Therefore, the mutual network of the living tissues of the intestinal canals $I_{C1}$, $I_{C2}$ which are not denatured is generated, and the tissue regenerative force of the living tissue is exerted, whereby the living tissues of the intestinal canals $I_{C1}$, $I_{C2}$ are regenerated earlier.

As described above, according to this modification, the following effect is obtained.

The continuous electrodes 302, 306 and the discrete electrodes 304, 308 are arranged on the holding faces 272b, 276b of the first and second holding members 262, 264, respectively. Then, the living tissue (e.g., the intestinal canals $I_{C1}$, $I_{C2}$) between the continuous electrode 302 of the first holding member 262 and the continuous electrode 306 of the second holding member 264 can be heated, denatured and continuously bonded. Therefore, for example, tubular living tissues can be brought into close contact with each other or sealed. Furthermore, the living tissue (e.g., the intestinal canals $I_{C1}$, $I_{C2}$) between the discrete electrodes 304 of the first holding member 262 and the discrete electrodes 308 of the second holding member 264 can be heated, denatured and continuously bonded to each other. That is, the living tissues can discretely be bonded to each other.

At this time, as shown in, for example, FIG. 20B, a portion in which the living tissues are continuously denatured and bonded to each other is positioned close to a portion in which the living tissues are discretely denatured and bonded to each other. Then, a portion between the living tissues around the portion in which the living tissues are discretely denatured and bonded to each other is not denatured. In consequence, it is possible to maintain a state where the living tissues which are not denatured around the discretely denatured and bonded portion are brought into (close) contact with each other. That is, the discrete electrodes 304, 308 perform a great role in maintaining the close contact state of the living tissues to which the force $F_1$ having, for example, such a direction that the tissues come away from each other is applied.

In a case where, for example, two intestinal canals $I_{C1}$, $I_{C2}$ are anastomosed with each other, the force $F_1$ acts in a direction in which the intestinal canals $I_{C1}$, $I_{C2}$ come away from each other on the side opposite to the side provided with the mesenterium M shown in FIGS. 20A and 20C. However, the intestinal canals $I_{C1}$, $I_{C2}$ are discretely bonded to each other by the discrete electrodes 304, so that the intestinal canals $I_{C1}$, $I_{C2}$ can discretely be bonded to each other. Therefore, the mutual close contact state of the intestinal canals $I_{C1}$, $I_{C2}$ can be maintained.

Therefore, the portion between the living tissues bonded to each other by the discrete electrodes 304, 308 performs a function of maintaining a state in which the living tissues are drawn to each other and brought into close contact with each other. That is, the portion between the living tissues bonded to each other by the discrete electrodes 304, 308 performs a function of maintaining the conglutination of the living tissues. Therefore, the mutual network of the living tissues brought into close contact (conglutinated) with each other is generated, and the tissue regenerative force of the living tissue is more easily exerted, whereby the living tissue can be regenerated earlier.

It is to be noted that in this modification, it has been described that the discrete electrodes 304 of the first holding member 262 are arranged at substantially equal intervals, and have a substantially equal area, but the space between the adjacent discrete electrodes 304 preferably varies, and the area of the discrete electrode 304 preferably varies. When the tissues are discretely treated by the discrete electrodes 304, the portions which come in contact with the discrete electrodes 304 are denatured. However, the discrete electrodes 304 may variously be modified as long as it is possible to maintain a state in which a part of the living tissue between the discrete electrodes 304 disposed adjacent to each other is not denatured and the living tissues are brought into contact with each other. Needless to say, this also applies to the discrete electrodes 308 of the second holding member 264. Moreover, the heater set temperature of the discrete electrode, the heater set temperature of the continuous electrode, output time and output timing may variously be combined so that a difference is given between them.

It is to be noted that in this modification, a case where the cutter 254 is provided has been described, but the cutter 254 does not have to be provided, depending on the treatment target. In a case where the cutter 254 is not provided, the above cutter guide grooves 262a, 264a can function as a fluid discharge groove (a channel) which guides a fluid such as vapor or a liquid generated from the living tissue to the handle 222 of the energy treatment instrument 212.

Next, the modification of the discrete electrodes 304 is shown in FIG. 19D. With regard to the discrete electrodes 304 of the first holding member 262 shown in FIG. 19A, an example has been described in which the discrete electrodes are arranged at equal intervals along the substantially U-shaped virtual track disposed outside the substantially U-shaped continuous electrode 302. In addition, as shown in FIG. 19D, the discrete electrodes 304 are preferably arranged in zigzag vertex positions. That is, the discrete electrodes 304 are preferably arranged in two rows. In this case, the arrangement of the discrete electrodes 304 and a distance between the electrodes are appropriately determined in accordance with the magnitude of the output of the continuous electrode 302, the area of the discrete electrode 304 itself with respect to the living tissue and the like.

It is to be noted that the discrete electrodes 304 may be arranged at random, and various other changes are allowed. Moreover, the shape of the discrete electrode 304 may variously be changed to a rectangular shape, an elliptic shape, a rhombic shape, a polygonal shape or the like.

As described above, according to this modification, the following effect is obtained.

The continuous electrodes 302, 306 and the discrete electrodes 304, 308 are arranged on the holding faces 272b, 276b of the first and second holding members 262, 264, respectively. Then, the living tissues (e.g., the intestinal canals $I_{C1}$, $I_{C2}$) between the continuous electrode 302 of the first holding member 262 and the continuous electrode 302 of the second holding member 264 can be heated, denatured and continuously bonded. Therefore, for example, tubular living tissues can be brought into close contact with each other and sealed. Furthermore, the living tissues (e.g., the intestinal canals $I_{C1}$, $I_{C2}$) between the discrete electrodes 304 of the first holding member 262 and the discrete electrodes 308 of the second holding member 264 can be heated and denatured to bond the living tissues to each other. That is, the living tissues can discretely be bonded to each other.

At this time, as shown in, for example, FIG. 20B, a portion in which the living tissues are continuously denatured and bonded to each other is positioned close to a portion in which the tissues are discretely denatured and bonded to each other. Then, a portion between the living tissues around the discretely denatured and bonded portion is not denatured. Therefore, the living tissues which are not denatured around the discretely denatured and bonded portion can be brought into (close) contact with each other. That is, the discrete electrodes 304, 308 perform a great role in maintaining, for example, a state where the living tissues to which the forces $F_1$ having a detaching direction are applied are brought into close contact with each other.

In a case where, for example, two intestinal canals $I_{C1}$, $I_{C2}$ are anastomosed with each other, the forces $F_1$ act in a direction in which the intestinal canals $I_{C1}$, $I_{C2}$ come away from each other on the side opposite to the side provided with the mesenterium M as shown in FIGS. 20A and 20C. However, the intestinal canals $I_{C1}$, $I_{C2}$ are discretely bonded to each other by the discrete electrodes 304, so that the intestinal canals $I_{C1}$, $I_{C2}$ can discretely be bonded to each other. Therefore, the intestinal canals $I_{C1}$, $I_{C2}$ can be maintained in a state in which the canals are brought into close contact with each other.

Therefore, the portion of the living tissues bonded to each other by the discrete electrodes 304, 308 performs a function of maintaining the state in which the living tissues are drawn to each other and brought into close contact with each other. That is, the portion of the living tissues bonded to each other by the discrete electrodes 304, 308 performs a function of maintaining the conglutination of the tissues. In consequence, the mutual network of the living tissues brought into contact (conglutinated) with each other is generated, the tissue regenerative force of the living tissue is more easily exerted, and the living tissue can be regenerated earlier.

It is to be noted that in this modification, it has been described that the discrete electrodes 304 of the first holding member 262 are arranged at substantially equal intervals, and have a substantially equal area, but it is preferable that the space between the adjacent discrete electrodes 304 or the area of the discrete electrode 304 varies. In a case where the tissues are discretely treated by the discrete electrodes 304, the portions which come in contact with the discrete electrodes 304 are denatured, but the discrete electrodes 304 may variously be modified as long as it is possible to maintain a state in which a part of the living tissue between the discrete electrodes 304 disposed adjacent to each other is not denatured and the living tissues are brought into contact with each other.

Fourth Modification of Second Embodiment

Next, a fourth modification will be described with reference to FIG. 21A. In this modification, the configuration of a first high-frequency electrode 266 provided on a main body 272 of a first holding member 262 will be described.

As shown in FIG. 21A, outside a substantially U-shaped continuous electrode 302, a plurality of branched electrodes (a maintaining member, a second bonding member) 312 branched from the continuous electrode 302 are integrally formed. These branched electrodes 312 extend in a direction crossing the axial direction of the continuous electrode 302 at right angles. That is, in this modification, the branched electrodes 312 are arranged instead of the discrete electrodes 304 described in the third modification.

The respective branched electrodes 312 are formed with a substantially equal length and a substantially equal width. That is, the respective branched electrodes 312 extend as much as a substantially equal area from the continuous electrode 302. A space between the branched electrodes 312 is a substantially equal space.

It is to be noted that the branched electrodes 312 denature a living tissue $L_T$ which comes in contact with the branched electrodes 312, but the electrodes 312 emit output to such an extent that the denaturation of the living tissue $L_T$ between the adjacent branched electrodes 312 is prevented. Such output depends on energy input from a high-frequency energy output circuit 292 or a heat generation element driving circuit 294 to the branched electrodes 312, additionally the space between the branched electrodes 312, the width of the branched electrode 312 itself and the like.

The function and effect of a treatment system 210 according to this modification are similar to those described in the second embodiment and the third modification of the second embodiment, and hence the description thereof is omitted.

It is to be noted that the length and width (thickness) of each branched electrode 312, further the space between the branched electrodes 312 and the number of the branched electrodes 312 are appropriately set. In FIG. 21A, it is depicted that the thickness of the continuous electrode 302 is larger than that of the branched electrode 312, but the thickness may be equal, and the thickness of the branched electrode 312 may be larger.

With regard to the branched electrodes 312, for example, modifications shown in FIGS. 21B and 21C are allowed. The modification of the branched electrodes 312 will be described with reference to FIG. 21B.

As shown in FIG. 21B, branched electrodes (a maintaining member, a second bonding member) 314 on the most distal end (a side away from a base portion 274) of a main body 272 of a first holding member 262 are deformed with respect to the branched electrodes 312 on the most distal end of the main body 272 of the first holding member 262 shown in FIG. 21A. That is, the branched electrodes 314 shown in FIG. 21B are formed to be long as compared with the branched electrodes 312 on the most distal end of the main body 272 of the first holding member 262 shown in FIG. 21A.

Moreover, the branched electrodes 312 on the most distal end shown in FIG. 21A extend only in one direction (straight). On the other hand, the extending angle of each of the branched electrodes 314 shown in FIG. 21B halfway changes (the electrode is halfway bent). This is because a bonding force to bond intestinal canals $I_{C1}$, $I_{C2}$ to each other is increased to prevent the release of the anastomosing of the canals, in a case where when the intestinal canals $I_{C1}$, $I_{C2}$ are anastomosed as shown in, for example, FIG. 20C, forces $F_2$ act so that the anastomosing of the intestinal canals $I_{C1}$, $I_{C2}$ is released from the distal end of a portion denatured by a continuous electrode 302, that is, a portion $B_i$ where the intestinal canals $I_{C1}$, $I_{C2}$ are branched.

The respective branched electrodes 314 shown in FIG. 21B extend in at least two directions. Each of these branched electrodes 314 includes a first portion 314a formed integrally with the continuous electrode 302 and extended in a direction crossing a substantially U-shaped virtual track of the continuous electrode 302 at right angles, and a second portion 314b formed integrally with the first portion 314a and extended further from the first portion 314a. The second portion 314b of these portions extend in parallel with the branched electrodes 312. Then, in such a constitution, the branched electrode 314 has the first portion 314a and the second portion 314b, whereby a bonding area corresponding to the forces $F_2$ generated in the branched portion $B_i$ can be increased. That is, owing to the first portion 314a and the second portion 314b, the intestinal canals $I_{C1}$, $I_{C2}$ bonded to each other do not easily peel.

Therefore, a resistance to the forces $F_2$ applied to the intestinal canals $I_{C1}$, $I_{C2}$ can be increased, so that a state in which the anastomosing of the intestinal canals $I_{C1}$, $I_{C2}$ is not easily released can be obtained.

Next, a further modification of the branched electrodes 312 will be described with reference to FIG. 21C.

As shown in FIG. 21C, branched electrodes (a maintaining member, a second bonding member) 316 of a first holding member 262 are deformed with respect to the branched electrodes 312 of the first holding member 262 shown in FIG. 21A. The branched electrodes 316 are arranged in an oblique direction, instead of a direction crossing the axial direction of a continuous electrode 302 (a substantially U-shaped virtual track) of the continuous electrode 302. In this modification, the branched electrodes 316 extend toward, for example, a proximal end.

Figure 20D:
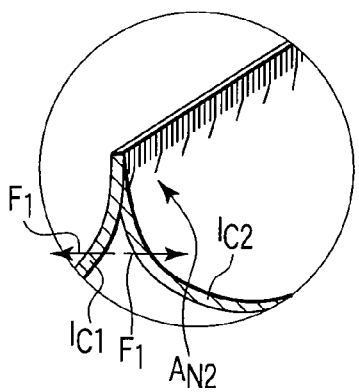
FIG. 20D is a schematic diagram as a modification of FIG. 20B showing the enlarged part denoted with the symbol 20B of FIG. 20A.

Therefore, as shown in FIG. 20D, in intestinal canals $I_{C1}$, $I_{C2}$, there are a portion bonded by the continuous electrode 302 and portions bonded by the branched electrodes 316 with an appropriate angle with respect to the longitudinal direction of the portion bonded by the continuous electrode 302. These branched electrodes 316 are formed to be long as compared with the branched electrodes 312 shown in FIG. 21A. Moreover, the portions bonded by the branched electrodes 316 are disposed obliquely with respect to the direction of forces $F_1$ applied to the intestinal canals $I_{C1}$, $I_{C2}$. Therefore, with regard to the branched electrodes 316, a bonding area corresponding to the forces $F_1$ having a direction to release anastomosing increases, so that a state in which the anastomosing of the intestinal canals $I_{C1}$, $I_{C2}$ is not easily released can be obtained. Therefore, the branched electrodes 316 having an appropriate angle with respect to the longitudinal direction of the portion connected to the continuous electrode 302 can have an increased bonding force to bond the intestinal canals $I_{C1}$, $I_{C2}$ to each other.

It is to be noted that as shown in FIG. 21C, branched electrodes (a maintaining member, a second bonding member) 318 on the most distal end of the first holding member 262 are deformed with respect to the branched electrodes 312, 314 on the most distal end of the first holding member 262 shown in FIGS. 21A and 21B. That is, these branched electrodes 318 of this modification are formed to be long as compared with the branched electrodes 312, 314 on the most distal end of the first holding member 262 shown in FIGS. 21A and 21B.

Furthermore, the branched electrodes 318 shown in FIG. 21C are circularly extended. Therefore, the branched electrodes 318 are extended in a direction different from that of the branched electrodes 316. In such branched electrodes 318 provided on the distal end of the first holding member 262, a resistance is increased against a time when forces $F_2$ are generated in a portion $B_i$ as shown in FIG. 21C, in a case where the intestinal canals $I_{C1}$, $I_{C2}$ are anastomosed are anastomosed. In consequence, the intestinal canals $I_{C1}$, $I_{C2}$ do not easily peel from each other.

This is because the bonding force to bond the intestinal canals $I_{C1}$, $I_{C2}$ to each other is increased to prevent the release of the anastomosing, in a case where, for example, when the intestinal canals $I_{C1}$, $I_{C2}$ are anastomosed, the forces $F_2$ act so that the anastomosing of the intestinal canals $I_{C1}$, $I_{C2}$ with each other is released from the distal end of a portion denatured by the continuous electrode 302, that is, the portion $B_i$ where the intestinal canals $I_{C1}$, $I_{C2}$ are branched from each other.

It is to be noted that in this modification, the branched electrodes 314 each having the first portion 314a and the second portion 314b and the branched electrodes 318 have been described as the branched electrodes disposed on the most distal end of the main body 272 of the first holding member 262 in a case where the area of the bonding portion corresponding to the forces $F_2$ is increased. However, the shapes of the branched electrodes disposed on the most distal end of the main body 272 of the first holding member 262 are not limited to these branched electrodes 314, 318, as long as the area of the bonding portion corresponding to the forces $F_2$ increases.

Fifth Modification of Second Embodiment

Next, a fifth modification will be described with reference to FIGS. 22A to 22C. In this modification, the configuration of a first high-frequency electrode 266 provided on a main body 272 of a first holding member 262 will be described.

As shown in FIG. 22A, the first high-frequency electrode 266 (a continuous electrode 302 and discrete electrodes 304) is arranged at substantially the same position as that in the third modification shown in FIG. 19A. Moreover, a heater member 268 is also arranged at substantially the same position as that in the third modification shown in FIG. 19A.

As shown in FIGS. 22A and 22B, the main body 272 is provided with a first fluid discharge groove (a fluid discharge groove for the continuous electrode) 332 as the channel of a fluid such as vapor or a high-temperature liquid outside the continuous electrode 302. The main body 272 is provided with second fluid discharge grooves (fluid discharge grooves for the discrete electrodes) 334 as the channels of a fluid such as the vapor or the high-temperature liquid in the outer peripheries of the discrete electrodes 304. These first and second fluid discharge grooves 332, 334 are connected to each other via communication paths 336. The communication paths 336 are formed as conduits. That is, the respective communication paths 336 are formed in the main body 272. Then, the respective communication paths 336 are connected to a cutter guide groove 262a in a base portion 274. That is, the first and second fluid discharge grooves 332, 334 are connected to the cutter guide groove 262a in the base portion 274.

In the main body 272 of the first holding member 262, a barrier portion (a dam) 342 for the continuous electrode 302 is formed outside the first fluid discharge groove 332 so that a fluid such as the vapor or the high-temperature liquid discharged owing to the function (including the function of the heater member 268) of the continuous electrode 302 flows into the first fluid discharge groove 332. In the main body 272, barrier portions 344 for the discrete electrodes 304 are formed in the outer peripheries of the second fluid discharge grooves 334 so that a fluid such as the vapor or the high-temperature liquid discharged owing to the function (including the function of the heater member 268) of the discrete electrodes 304 flows into the second fluid discharge grooves 334. As shown in FIG. 22B, these barrier portions 342, 344 are protruded from the plane a holding face 272b of the main body.

It is to be noted that similarly in a second holding member 264, a fluid discharge groove (conveniently denoted with reference numeral 352) is formed outside a continuous electrode 306, and a barrier portion (conveniently denoted with reference numeral 362) is formed outside the fluid discharge groove 352. Moreover, fluid discharge grooves (conveniently denoted with reference numeral 354) are formed in the outer peripheries of discrete electrodes 308 of the second holding member 264, and barrier portions (conveniently denoted with reference numeral 364) are formed in the outer peripheries of the fluid discharge grooves 354. Then, the fluid discharge groove 352 outside the continuous electrode 306 is connected to the fluid discharge grooves 354 in the outer peripheries of the discrete electrodes 308 via a communication path (conveniently denoted with reference numeral 356).

Next, the function of a treatment system 210 according to this modification will be described.

As described in the second embodiment, a living tissue $L_T$ as a treatment target is held between the first holding member 262 and the second holding member 264. At this time, the barrier portions 342, 344 of the main body 272 of the first holding member 262 and the barrier portions 362, 364 of a main body 276 of the second holding member 264 come in close contact with the living tissue $L_T$, and the living tissue $L_T$ comes in contact with the first high-frequency electrode 266 and a second high-frequency electrode 270.

In this state, a pedal 216a of a foot switch 216 is operated. Energy is supplied from an energy source 214 to the first high-frequency electrode 266 and the second high-frequency electrode 270, respectively. Then, the living tissue $L_T$ between the first high-frequency electrode 266 and the second high-frequency electrode 270 is heated by high-frequency energy and heat energy. At this time, a fluid such as vapor or a liquid is discharged from, for example, the heated portion of the living tissue $L_T$.

Here, the first fluid discharge groove 332 of the main body 272 of the first holding member 262 is arranged outside the continuous electrode 302, and the second fluid discharge grooves 334 are arranged in the outer peripheries of the discrete electrodes 304.

In consequence, the fluid discharged owing to the function of the continuous electrode 302 flows into the cutter guide groove 262$_a$, and also flows into the first fluid discharge groove 332. Then, the fluid is prevented from being discharged from the grooves by the barrier portion 342. Therefore, the fluid discharged from the living tissue $L_T$ is kept internally from the barrier portion 342, and is prevented from being released from the barrier portion. That is, the barrier portion 342 performs the function of a dam which prevents the fluid discharged from the living tissue $L_T$ from leaking from the barrier portion 342.

The fluid discharged owing to the function of the discrete electrodes 304 flows into the second fluid discharge grooves 334. Then, the fluid is prevented from flowing outwards by the barrier portions 344. In consequence, the fluid discharged from the living tissue $L_T$ is kept internally from the barrier portions 344, and is prevented from being released from the portions. That is, the barrier portions 344 perform the function of a dam which prevents the fluid discharged from the living tissue $L_T$ from leaking from the barrier portions 344.

The fluid which has flowed into the second fluid discharge grooves 334 flows into the first fluid discharge groove 332 through the communication paths 336. Then, this fluid joins the fluid which has flowed into the first fluid discharge groove 332 to flow toward the base portion 274 of the first holding member 262. Then, the fluid flows into the cutter guide groove 262a connected to the first fluid discharge groove 332 in, for example, the base portion 274. The first fluid discharge groove 332 communicates with the inside of a cylindrical member 242 of a shaft 224 (not shown).

Then, the fluid is discharged from a surgical treatment instrument 12 via a fluid discharge port 244a of a sheath 244 through a fluid discharge port 242a of the cylindrical member 242 of the shaft 224.

As described above, according to this modification, the following effect is obtained. The description of an effect similar to that described in the fourth modification of the second embodiment is omitted.

When a high-frequency current is applied to the living tissue $L_T$ as the treatment target held by a holding section 226 of the surgical treatment instrument 212, the barrier portions 342, 344, 362 and 364 are brought into close contact with the living tissue. In consequence, even when the fluid discharged from the living tissue $L_T$ as the treatment target flows toward the barrier portions 342, 344 of the first holding member 262, the fluid can be introduced into the first and second fluid discharge grooves 332, 334, 352 and 354 and the communication paths 336, 356 of the first and second high-frequency electrodes 266, 270.

In consequence, another peripheral tissue can be prevented from being influenced by the fluid discharged from the portions treated by the high-frequency energy and heat energy during the treatment of the living tissue $L_T$. That is, a position to be influenced during the treatment of the living tissue $L_T$ can be limited to the living tissue $L_T$ in which the high-frequency current is supplied between the first high-frequency electrode 266 and the second high-frequency electrode 270.

Therefore, according to this modification, a fluid such as the vapor or liquid (a high-temperature body fluid) generated from the living tissue $L_T$ is discharged from the surgical treatment instrument 212 on the side of, for example, the proximal end of the shaft 224 or a handle 222, whereby a living tissue around the living tissue $L_T$ as the treatment target can be inhibited from being influenced by a fluid such as the vapor or liquid (the body fluid).

Thus, when the thermal influence on the living tissue $L_T$ is suppressed, it is important to guide a fluid such as the vapor or liquid to a position which does not come in contact with the tissue. In a case where a tissue which is larger than the holding section 226 to such an extent that the periphery of the holding section 226 is covered is subjected to the treatment, it can be prevented that the outside of the holding section 226 is thermally influenced. In a case where even a small open portion (space) from which a fluid such as the vapor or liquid leaks is formed in the holding section 226, the fluid is discharged from the portion, and thermally influences the living tissue $L_T$ around the holding section 226.

Moreover, even when the peripheries of the high-frequency electrodes (energy release portions) 266, 270 are covered with the barrier portions 342, 344, 362 and 364 to eliminate such an open portion, an open portion might be formed owing to a fluid pressure such as the vapor pressure generated from the living tissue $L_T$, and the fluid might be discharged. Therefore, it is useful means to provide channels (the first and second fluid discharge grooves 332, 334, 352 and 354 and the communication paths 336, 356) which suppress the discharge of the unnecessary fluid due to the rise of the fluid pressure and which guide and discharge the fluid in a predetermined direction.

Next, a modification of the communication paths 336 shown in FIGS. 22A and 22B will be described with reference to FIG. 22C.

As shown in FIG. 22C, a communication path 336 (hereinafter referred to as a first communication path) is formed as a conduit in the same manner as in the fifth modification.

The first communication path 336 is provided with a tubular second communication path 338 also connected to a cutter guide groove 262a of a main body 272.

Thus, a fluid generated from a living tissue $L_T$ is passed through the first and second tubular communication paths 336, 338, whereby, for example, a fluid which might have a high temperature can be prevented as much as possible from being brought into contact with the living tissue $L_T$.

Third Embodiment

Next, a third embodiment will be described with reference to FIGS. 23 to 24C. This embodiment is a modification of the first and second embodiments including various modifications.

Here, as one example of an energy treatment instrument, a circular type bipolar energy treatment instrument (a treatment instrument) 412 for performing a treatment, for example, through or outside an abdominal wall will be described.

As shown in FIG. 23, a treatment system 410 includes the energy treatment instrument 412, an energy source 214 and a foot switch 216. The surgical treatment instrument 412 includes a handle 422, a shaft 424 and an openable/closable holding section 426. The handle 422 is connected to the energy source 214 via a cable 228.

The handle 422 is provided with a holding section opening/closing knob 432 and a cutter driving lever 434. The holding section opening/closing knob 432 is rotatable with respect to the handle 422. When the holding section opening/closing knob 432 is rotated, for example, clockwise with respect to the handle 422, a detachable side holding section (a detachable side grasping section) 444 of the holding section 426 described later comes away from a main body side holding section (a main body side grasping section) 442 (see FIG. 24A). When the knob 432 is rotated counterclockwise, the detachable side holding section 444 comes close to the main body side holding section 442 (see FIG. 24B).

The shaft 424 is formed into a cylindrical shape. The shaft 424 is appropriately curved in consideration of an insertion property into a living tissue $L_T$. Needless to say, it is also preferable that the shaft 424 is formed to be straight.

Figure 24A:
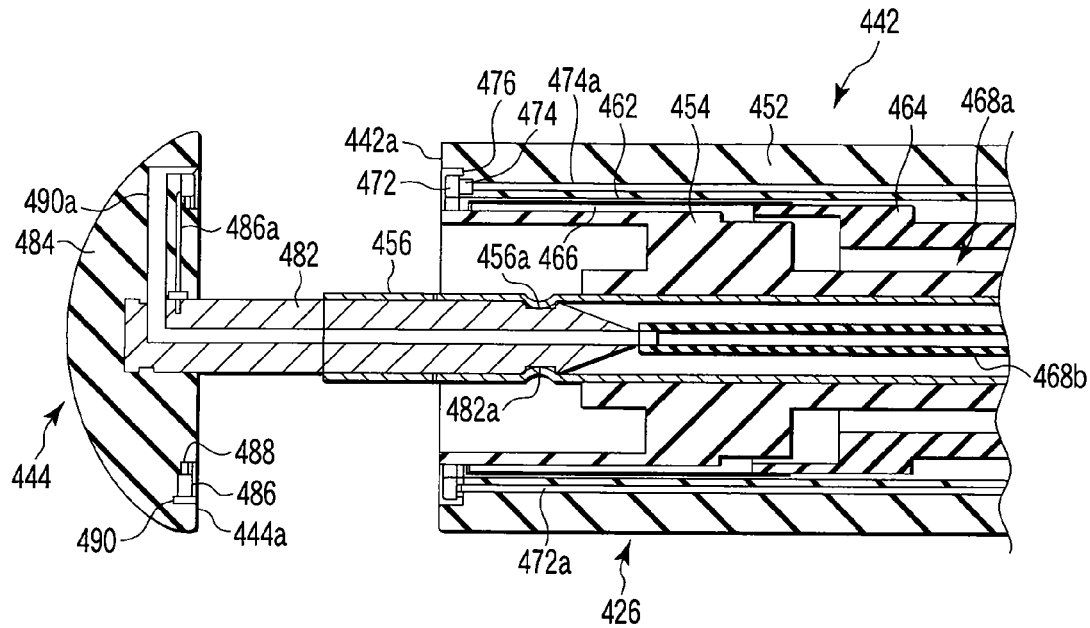
FIG. 24A is a schematic vertical sectional view showing a state in which a main body side holding section and a detachable side holding section of an energy treatment instrument according to the third embodiment are engaged, and the detachable side holding section is disposed away from the main body side holding section.
Figure 24B:
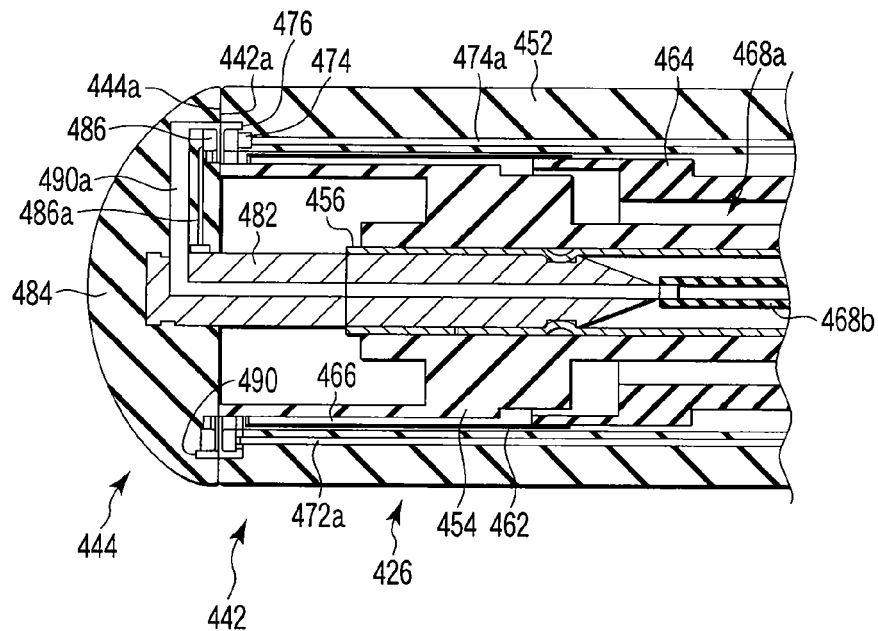
FIG. 24B is a schematic vertical sectional view showing a state in which the main body side holding section and the detachable side holding section of the energy treatment instrument according to the third embodiment are engaged, and the detachable side holding section is engaged with the main body side holding section.

The distal end of the shaft 424 is provided with the holding section 426. As shown in FIGS. 24A and 24B, the holding section 426 includes the main body side holding section (a first holding member, a first jaw) 442 formed on the distal end of the shaft 424, and the detachable side holding section (a second holding member, a second jaw) 444 detachably attached to the main body side holding section 442. In a state in which the detachable side holding section 444 closes with respect to the main body side holding section 442, holding faces 442a, 444a of the main body side holding section 442 and the detachable side holding section 444 come in contact with each other.

The main body side holding section 442 includes a cylindrical member 452, a frame 454 and a pipe 456 for energization. These cylindrical member 452 and frame 454 have an insulation property. The cylindrical member 452 is connected to the distal end of the shaft 424. The frame 454 is arranged so that the frame is fixed to the cylindrical member 452.

The central axis of the frame 454 is opened. This opened central axis of the frame 454 is provided with the pipe 456 for energization so that the pipe 456 is movable in a predetermined range along the central axis of the frame 454. When the holding section opening/closing knob 432 is rotated, this pipe 456 for energization is movable in the predetermined range owing to, for example, the function of a ball screw (not shown) as shown in FIGS. 24A and 24B. This pipe 456 for energization is provided with a protrusion 456a protruding inwardly in a diametric direction so that the protrusion 456a can disengageably be engaged with a connecting portion 482a of an energization shaft 482 of the detachable side holding section 444 described later.

As shown in FIGS. 24A and 24B, a cutter guide groove (a space) 466 is formed between the cylindrical member 452 and the frame 454. A cylindrical cutter 462 is arranged in this cutter guide groove 466. The proximal end of the cutter 462 is connected to the distal end of a pusher 464 for the cutter 462 provided on the inner side of the shaft 424. The cutter 462 is fixed to the outer peripheral surface of the pusher 464 for the cutter 462. Although not shown, the proximal end of the pusher 464 for the cutter 462 is connected to the cutter driving lever 434 of the handle 422. Therefore, when the cutter driving lever 434 of the handle 422 is operated, the cutter 462 moves via the pusher 464 for the cutter 462.

A first fluid passage (a fluid passage) 468a is formed between the pusher 464 for the cutter 462 and the frame 454. Then, the shaft 424 or the handle 422 is provided with a fluid discharge port (not shown) through which the fluid passed through the first fluid passage 468a is discharged.

Figure 24C:
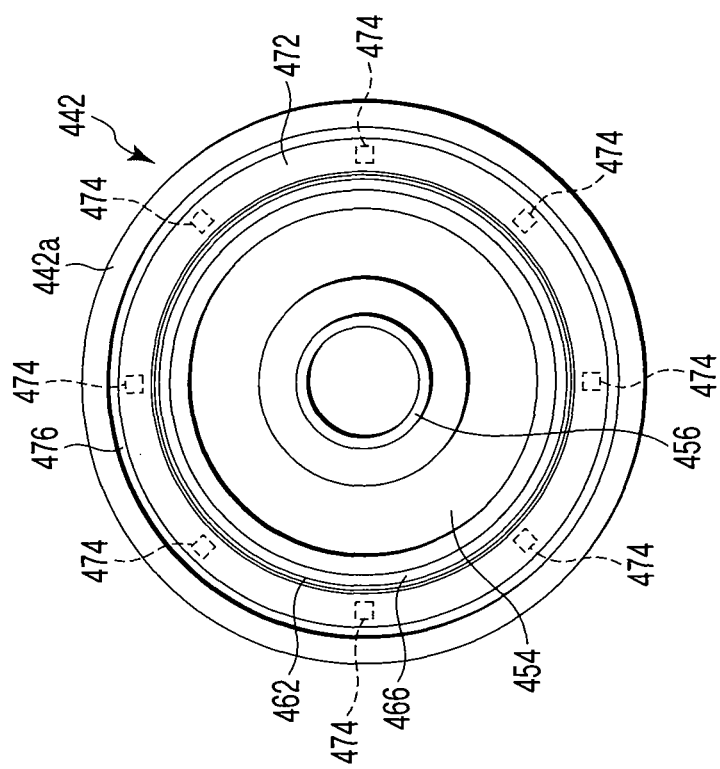
FIG. 24C is a schematic diagram showing the front surface of the main body side holding section of the energy treatment instrument according to the third embodiment.

As shown in FIGS. 24A to 24C, the distal end of the cylindrical member 452 is provided with a first high-frequency electrode 472 and a heater member 474 as an output member and an energy release section.

The first high-frequency electrode 472 is arranged outside the cutter guide groove 466 in which the cutter 462 is arranged. The first high-frequency electrode 472 is formed into an annular shape in the same manner as in the cutter guide groove 466. The first high-frequency electrode 472 is fixed to the distal end of a first energization line 472a. The first energization line 472a is connected to the cable 228 via the main body side holding section 442, the shaft 424 and the handle 422.

As shown in FIGS. 24A to 24C, the heater members 474 are fixed to the back surface of the first high-frequency electrode 472 at appropriate intervals. The heater member 474 is fixed to the distal end of an energization line 474a for the heater. The energization line 474a for the heater is connected to the cable 228 via the main body side holding section 442, the shaft 424 and the handle 422.

An annular vapor discharge groove 476 is formed outside the first high-frequency electrode 472. The vapor discharge groove 476 is connected to the first fluid passage 468a. Outside the vapor discharge groove 476, the holding face (a tissue contact face) 442a is formed at a position higher than the front surface of the first high-frequency electrode 472. That is, the holding face 442a of the main body side holding section 442 is disposed closer to a head section 484 of the detachable side holding section 444 described later than the front surface of the first high-frequency electrode 472 is. Therefore, the holding face 442a performs the function of a barrier portion (a dam) which prevents a fluid such as vapor from being discharged from the vapor discharge groove 476.

On the other hand, the detachable side holding section 444 includes the shaft 482 for energization having the connecting portion 482a and the head section 484. The shaft 482 for energization has a circular section, and has one end tapered and the other end fixed to the head section 484. The connecting portion 482a is formed into a concave-groove-like shape which is engageable with the protrusion 456a of the pipe 456 for energization. The outer surface of the energization shaft 482 other than the connecting portion 482a is insulated by coating or the like.

The head section 484 is provided with a second high-frequency electrode 486 so that the electrode 486 faces the first high-frequency electrode 472 of the main body side holding section 442. The second high-frequency electrode 486 is fixed to one end of a second energization line 486a. The other end of the second energization line 486a is electrically connected to the shaft 482 for energization.

On the inner side of the second high-frequency electrode 486 provided on the head section 484, an annular cutter receiving portion 488 is formed to receive the blade of the cutter 462. On the other hand, an annular fluid discharge groove 490 is formed outside the second high-frequency electrode 486. Outside the fluid discharge groove 490, the holding face (a tissue contact face) 444a is formed at a position higher than the front surface of the second high-frequency electrode 486. That is, the holding face 444a of the detachable side holding section 444 is disposed closer to the main body side holding section 442 than the front surface of the second high-frequency electrode 486 is. Therefore, the holding face 444a performs a barrier portion (a dam) which prevents a fluid such as the vapor from being discharged from the fluid discharge groove 490.

Furthermore, the fluid discharge groove 490 is connected to a fluid discharge path 490a of the head section 484 and the shaft 482 for energization. The fluid discharge path 490a communicates with a second fluid passage (a fluid passage) 468b of the pipe 456 for energization. The shaft 204 or the handle 202 is provided with a fluid discharge port (not shown) from which the fluid passed through the second fluid passage 468b is discharged.

It is to be noted that the pipe 456 for energization is connected to the cable 228 via the shaft 424 and the handle 422. In consequence, when the connecting portion 482a of the energization shaft 482 of the detachable side holding section 444 is engaged with the protrusion 456a of the pipe 456 for energization, the second high-frequency electrode 486 is electrically connected to the pipe 456 for energization.

Next, the function of the treatment system 410 according to this embodiment will be described.

An operator operates a display section 296 (see FIG. 13) of the energy source 214 in advance to set the output conditions of the treatment system 210. Specifically, a set power Pset [W] of high-frequency energy output, a set temperature Tset [° C.] of heat energy output, threshold values Z1, Z2 of an impedance Z of the living tissue $L_T$ and the like are set.

As shown in FIG. 24B, the holding section 426 and the shaft 424 of the surgical treatment instrument 412 are inserted into an abdominal cavity through, for example, an abdominal wall in a state in which the main body side holding section 442 is closed with respect to the detachable side holding section 444. The main body side holding section 442 and the detachable side holding section 444 of the surgical treatment instrument 412 are opposed to the living tissue $L_T$ to be treated.

To grasp the living tissue $L_T$ to be treated between the main body side holding section 442 and the detachable side holding section 444, the holding section opening/closing knob 432 of the handle 422 is operated. At this time, the knob 432 is rotated, for example, clockwise with respect to the handle 422. Then, as shown in FIG. 24A, the pipe 456 for energization is moved to the distal end with respect to the frame 454 of the shaft 424. Therefore, the main body side holding section 442 and the detachable side holding section 444 open, whereby the detachable side holding section 444 can come away from the main body side holding section 442.

Then, the living tissue $L_T$ to be treated is arranged between the first high-frequency electrode 472 of the main body side holding section 442 and the second high-frequency electrode 486 of the detachable side holding section 444. The energization shaft 482 of the detachable side holding section 444 is inserted into the energization pipe 456 of the main body side holding section 442. In this state, the grasping section opening/closing knob 432 of the handle 422 is rotated, for example, counterclockwise. In consequence, the detachable side holding section 444 closes with respect to the main body side holding section 442. Thus, the living tissue $L_T$ as the treatment target is held between the main body side holding section 442 and the detachable side holding section 444.

In this state, the pedal 216a of the foot switch 216 is operated, and the energy is supplied from the energy source 214 to the first high-frequency electrode 472 and the second high-frequency electrode 486 via the cable 228. Therefore, the living tissue $L_T$ between the main body side holding section 442 and the detachable side holding section 444 is heated by Joule heat. At this time, the impedance Z of the grasped living tissue $L_T$ is measured by a high-frequency energy output circuit 292. The impedance Z at the time of treatment start is, for example, about 60 [Ω] as shown in FIG. 15. Subsequently, when the high-frequency current flows through the living tissue $L_T$ and the living tissue $L_T$ is cauterized, the value of the impedance Z once lowers and then rises.

Thus, when the living tissue $L_T$ is cauterized, the fluid (a liquid (blood) and/or a gas (water vapor)) is discharged from the living tissue $L_T$. At this time, the fluid discharged from the living tissue $L_T$ is allowed to flow into the cutter guide groove 466 and the vapor discharge groove 476 of the main body side holding section 442 and to flow into the fluid discharge groove 490 of the detachable side holding section 444. Then, the fluid which has flowed into the cutter guide groove 466 and the vapor discharge groove 476 of the main body side holding section 442 is, for example, sucked and discharged from the cutter guide groove 466 to the shaft 424 through the first fluid passage 468a. The fluid allowed to flow into the fluid discharge groove 490 of the detachable side holding section 444 is, for example, sucked and discharged from the fluid discharge path 490a of the head section 484 and energization shaft 482 to the shaft 424 through the second fluid passage 468b of the energization pipe 456.

Then, while the fluid is discharged from the living tissue $L_T$, the fluid continues to flow into the groove. Therefore, the occurrence of thermal spread is prevented by the fluid discharged at a raised temperature from the living tissue $L_T$, and the influence on a portion which is not the treatment target can be prevented.

Subsequently, a control section 290 judges whether the impedance Z during the high-frequency energy output calculated based on a signal from the high-frequency energy output circuit 292 is the preset threshold value Z1 (here, about 1000 [Ω] as shown in FIG. 15) or more. The threshold value Z1 is disposed in a position where the rise ratio of the beforehand known value of the impedance Z lowers. Then, in a case where it is judged that the impedance Z is smaller than the threshold value Z1, the high-frequency energy for the treatment is continuously applied to the living tissue $L_T$ grasped between the electrodes 472 and 486 of the main body side holding section 442 and the detachable side holding section 444.

In a case where it is judged that the impedance Z is larger than the threshold value Z1, the control section 290 transmits a signal to a heat generation element driving circuit 294. Then, the heat generation element driving circuit 294 supplies a power to the heater member 474 so that the temperature of the heater member 474 is a preset temperature Tset [° C.], for example, a temperature of 100 [° C.] to 300 [° C.]. In consequence, the living tissue $L_T$ grasped between the electrodes 472 and 486 of the main body side holding section 442 and the detachable side holding section 444 conducts heat to the first high-frequency electrode 472 owing to heat conduction from the heater member 474, and the heat coagulates the living tissue $L_T$ internally from the side of the front surface of the living tissue $L_T$ which comes in close contact with the first high-frequency electrode 472.

Subsequently, the control section 290 judges whether the impedance Z of the living tissue $L_T$ monitored by the high-frequency energy output circuit 292 is a preset threshold value Z2 or more. In a case where it is judged that the impedance Z is smaller than the threshold value Z2, the energy continues to be applied to the heater member 474. On the other hand, in a case where it is judged that the impedance Z is the threshold value Z2 or more, the control section 290 issues a buzzer sound from a speaker 298, and stops the output of high-frequency energy and heat energy. In consequence, the treatment of the living tissue $L_T$ by use of the treatment system 410 is completed.

In this case, the living tissue $L_T$ is continuously (in a substantially annular state) denatured by the first and second high-frequency electrodes 472, 486.

Subsequently, when the cutter driving lever 434 of the handle 422 is operated, the cutter 462 protrudes from the cutter guide groove 466 of the main body side holding section 442, and moves toward the cutter receiving portion 488 of the detachable side holding section 444. The distal end of the cutter 462 has a blade, so that the treated living tissue $L_T$ is cut into a circular shape or the like.

As described above, according to this embodiment, the following effect is obtained.

The first high-frequency electrode 472 and the heater member 474 are arranged on the main body side holding section 442, and the second high-frequency electrode 486 is arranged on the detachable side holding section 444. In consequence, the living tissue $L_T$ between the main body side holding section 442 and the detachable side holding section 444 can be heated, denatured and bonded by the high-frequency energy and the heat energy. Therefore, the living tissues $L_T$ are sealed into a substantially annular shape.

Moreover, in this embodiment, the bipolar surgical treatment instrument 412 has been described, but it is also preferable to use a monopolar high-frequency treatment as described in the first embodiment with reference to FIG. 3B.

First Modification of Third Embodiment

Next, a first modification will be described with reference to FIG. 25.

Figure 25:
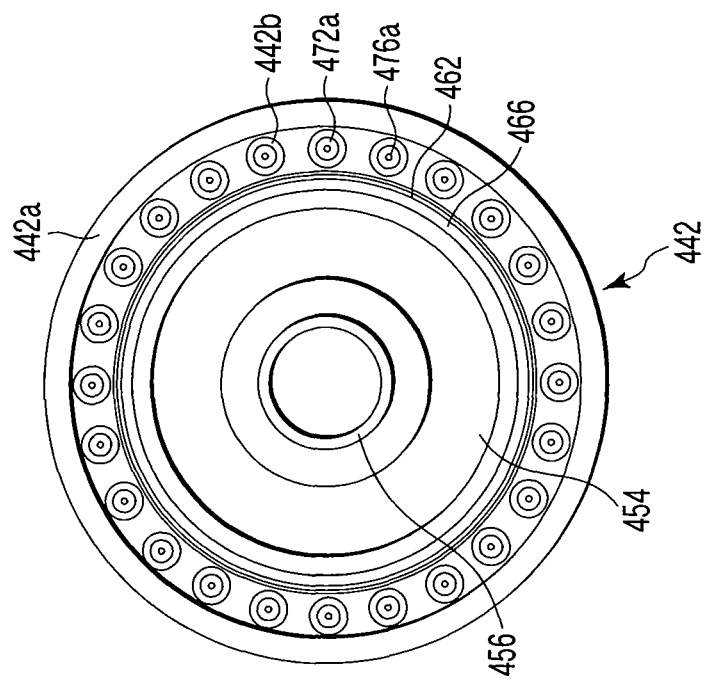
FIG. 25 is a schematic diagram showing the front surface of the main body side holding section of the energy treatment instrument according to a modification of the third embodiment.

On a main body side holding section 442 of a surgical treatment instrument 412 shown in FIG. 25, unlike the first high-frequency electrode 472 of the third embodiment, a plurality of discrete electrodes 472a for outputting high-frequency energy are arranged. The discrete electrodes 472a are arranged at predetermined intervals along a circumference. Although not shown, a heater member 474 is arranged on the back surfaces of the plurality of discrete electrodes 472a.

In each discrete electrode 472a, instead of a vapor discharge groove 476, a fluid discharge hole 476a is formed in the center of the discrete electrode 472a. Furthermore, barrier portions 442b having the same plane as holding faces 442a are arranged in the outer peripheries of the respective discrete electrodes 472a.

Therefore, the fluid discharged from the living tissue $L_T$ owing to the function (including the function of the heater member 474) of the respective discrete electrodes 472a is prevented from being released outwards by the barrier portions 442b. Then, the fluid discharged from the living tissue $L_T$ flows into the fluid discharge holes 476a disposed in the centers of the discrete electrodes 472a. In this case, the fluid which has flowed into the fluid discharge holes 476a is, for example, sucked and discharged from a cutter guide groove 466 to a shaft 424 through a first fluid passage 468a.

On the other hand, a second high-frequency electrode of a detachable side holding section 444 is not shown, but as described in the third embodiment, a continuous electrode formed into an annular shape may be arranged, or the second high-frequency electrode may be arranged similarly to (symmetrically with respect to) the discrete electrodes 472a of the main body side holding section 442 according to this modification.

It is to be noted that in the third embodiment including this modification, the use of the high-frequency electrodes 472, 472a shown in FIGS. 24C and 25 has been described, but the shapes and arrangement of the electrodes can variously be modified as in, for example, the configuration described in the second embodiment including various modifications. In consequence, for example, it is also preferable to arrange discrete electrodes or branched electrodes outside the high-frequency electrode 472 shown in FIG. 24C.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system configured to exert energy to a living tissue to treat the living tissue, comprising:
    a pair of holding portions configured to hold the living tissue therebetween, at least one of the holding portions is configured to move relatively with respect to the other holding portion to hold the living tissue;
    a high-frequency energy output section configured to output high-frequency energy to the living tissue to elevate a temperature of the living tissue to reach a first temperature in a state of dehydration;
    a heat generation section configured to output heat energy to the living tissue;
    a switch; and
    a control section configured such that if the switch is turned on and is maintained in a turned on state, the control section controls the high-frequency energy output section to output high-frequency energy to cause the temperature of the living tissue to reach the first temperature and controls the high-frequency energy output section to keep outputting the high-frequency energy at least until the temperature reaches a second temperature higher than the first temperature and controls the heat generation section to start outputting heat energy, later than the start of the high-frequency energy output section, to also assist in heating the living tissue to the second temperature, wherein the control section is further configured to control the heat generation section to stop outputting the heat energy after the second temperature has been reached and after the second temperature has been maintained for a predetermined time span.

2. The treatment system according to claim 1, wherein
the high-frequency energy output section includes an electrode which is provided on the at least one of the holding portions, and
the heat generation section includes a heater member which is at a back surface of the high-frequency energy output section-, and heat energy is conducted from the heater member to the living tissue via the high-frequency energy output section.

3. The treatment system according to claim 1, wherein the control section includes a setting portion configured to set a time to switchably supply energy to the high-frequency energy output section and the heat generation section.

4. The treatment system according to claim 1, wherein the control section is configured to control the heat generation section so as to keep the second temperature is in a range of 100° C. to 300° C.

5. The treatment system according to claim 1, comprising a first detector configured to detect biological information indicating a state of dehydration of the living tissue,
wherein the control section is configured to control the high-frequency energy output section to be supplied with power to exert the high-frequency energy at a power of 20 W to 80 W, based on the biological information detected by the first detector.

6. The treatment system according to claim 1, comprising a sensor which is configured to detect temperature information of the living tissue or biological information of the living tissue,
wherein the control section is configured to stop the output of the heat generation section based on the temperature information or the biological information after maintaining the second temperature for the predetermined time span.

7. A treatment system configured to exert energy to a living tissue to treat the living tissue; comprising:
a pair of holding portions configured to hold the living tissue therebetween, at least one of the holding portions is configured to move relatively with respect to the other holding portion to hold the living tissue;
a high-frequency energy output section provided on the at least one of the holding portions and configured to output high-frequency energy to the living tissue held by the holding portions, to dehydrate the living tissue;
a heat generation section configured to produce and output heat energy to the living tissue held by the holding portions, to dehydrate the living tissue;
a high-frequency energy output circuit connected to the high-frequency energy output section and configured to detect biological information indicating a state of dehydration of the living tissue;
a heat generation element driving circuit electrically connected to the heat generation section and configured to switch between a state of supplying the heat energy to the heat generation section and a state of not supplying the heat energy to the heat generation section;
a setting portion configured to preliminarily set a first threshold value and a second threshold value which is compared to the biological information, the second threshold value is higher than the first threshold value,
a switch; and
a control section being configured such that if the switch is turned on and is maintained in a turned on state, the control section controls the high-frequency energy output section to supply the high-frequency energy to the living tissue until the biological information reaches the first threshold value, and the control section is configured to start the supplying of the heat energy from the heat generation section after the biological information reaches the first threshold value, and the control section is also configured to keep the supplying of the high-frequency energy until the biological information reaches the second threshold value and the supplying of heat energy until the biological information exceeds the second threshold value, wherein the control section is configured to stop the supplying of the heat energy after the biological information reaches the second threshold value, and after the second threshold value has been maintained for a predetermined time span.

8. The treatment system according to claim 7, wherein the setting portion is configured to set a time to switch between energy output of the high-frequency energy output section and energy outputs of the high-frequency energy output section and the heat generation section.

9. The treatment system according to claim 7, comprising a first detector configured to detect the biological information indicating a state of dehydration of the living tissue,
wherein the control section is configured to control the heat generation section to be supplied with power to exert the heat energy at a temperature setting so as to keep in a range of 100° C. to 300° C., based on the biological information detected by the first detector.

10. The treatment system according to claim 7, comprising a first detector configured to detect the biological information indicating a state of dehydration of the living tissue,
wherein the control section is configured to control the high-frequency energy output section to be supplied with power to provide the high-frequency energy at a power of 20 W to 80 W, based on the biological information detected by the first detector.

11. The treatment system according to claim 7, wherein
the high-frequency energy output section includes an electrode which is provided on the at least one of the holding portions,
the heat generation section includes a heater member which is at a back surface of the high-frequency energy output section, and
heat energy is conducted from the heater member to the living tissue via the high-frequency energy output section.

12. The treatment system according to claim 7, wherein the heat generation section includes a heater member with a film resistance.

* * * * *